United States Patent
Georgiou et al.

(10) Patent No.: US 11,958,904 B2
(45) Date of Patent: Apr. 16, 2024

(54) ENGINEERED ANTIBODY FC VARIANTS FOR ENHANCED SERUM HALF LIFE

(71) Applicant: Research Development Foundation, Carson City, NV (US)

(72) Inventors: George Georgiou, Austin, TX (US); Chang-Han Lee, Austin, TX (US); Tae Hyun Kang, Austin, TX (US)

(73) Assignee: Research Development Foundation, Carson City, NV (US)

( * ) Notice: Subject to any disclaimer, the term of this patent is extended or adjusted under 35 U.S.C. 154(b) by 468 days.

(21) Appl. No.: 17/346,648

(22) Filed: Jun. 14, 2021

(65) Prior Publication Data

US 2021/0347891 A1 Nov. 11, 2021

Related U.S. Application Data

(62) Division of application No. 16/101,421, filed on Aug. 11, 2018, now Pat. No. 11,059,892.

(60) Provisional application No. 62/544,622, filed on Aug. 11, 2017.

(51) Int. Cl.
| | | |
|---|---|---|
| C07H 21/02 | (2006.01) | |
| C07H 21/04 | (2006.01) | |
| C07K 16/00 | (2006.01) | |
| C07K 16/28 | (2006.01) | |
| C07K 16/32 | (2006.01) | |
| C12N 5/00 | (2006.01) | |
| A61K 39/00 | (2006.01) | |

(52) U.S. Cl.
CPC ............ *C07K 16/283* (2013.01); *C07K 16/00* (2013.01); *C07K 16/32* (2013.01); *A61K 2039/505* (2013.01); *C07K 2317/41* (2013.01); *C07K 2317/52* (2013.01); *C07K 2317/524* (2013.01); *C07K 2317/526* (2013.01); *C07K 2317/72* (2013.01); *C07K 2317/732* (2013.01); *C07K 2317/75* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 7,094,571 B2 | 8/2006 | Harvey et al. |
| 7,419,783 B2 | 9/2008 | Georgiou et al. |
| 7,611,866 B2 | 11/2009 | Georgiou et al. |
| 8,367,805 B2 | 2/2013 | Chamberlain et al. |
| 8,546,543 B2 | 10/2013 | Lazar |
| 8,546,643 B2 | 10/2013 | Lazar |
| 8,618,252 B2 | 12/2013 | Farrington et al. |
| 2003/0219870 A1 | 11/2003 | Georgiou et al. |
| 2005/0054832 A1 | 3/2005 | Lazar et al. |
| 2006/0134709 A1 | 6/2006 | Stavenhagen et al. |
| 2006/0173170 A1 | 8/2006 | Chamberlain et al. |
| 2006/0275282 A1 | 12/2006 | Moore et al. |
| 2010/0330076 A1 | 12/2010 | Georgiou et al. |
| 2012/0128663 A1 | 5/2012 | Lazar |
| 2013/0131319 A1 | 5/2013 | Igawa et al. |
| 2013/0209457 A1 | 8/2013 | Lazar et al. |
| 2014/0363428 A1 | 12/2014 | Igawa et al. |
| 2014/0377280 A1 | 12/2014 | Ravetch et al. |
| 2015/0050269 A1 | 2/2015 | Igawa et al. |
| 2015/0344913 A1 | 12/2015 | Ohto et al. |
| 2019/0185557 A1 | 5/2019 | Igawa et al. |

FOREIGN PATENT DOCUMENTS

| | | |
|---|---|---|
| EP | 2762493 | 8/2014 |
| EP | 2857419 | 4/2015 |
| WO | WO 2008/137475 | 11/2008 |
| WO | WO 2013/046704 | 4/2013 |
| WO | WO 2013/047748 | 3/2015 |
| WO | WO 2016/071376 | 5/2016 |
| WO | WO 2019/028316 | 2/2019 |

OTHER PUBLICATIONS

Borrok et al., "pH-dependent binding engineering reveals an FcRn affinity threshold that governs IgG recycling", *J Biol Chem.*, 290(7):4282-4290, 2015.
Borrok et al., "Revisiting the role of glycosylation in the structure of human IgG Fc.", *ACS Chem. Biol.*, 7(9):1596-1602, 2012.
Borvak et al., "Functional expression of the MHC class I-related receptor, FcRn, in endothelial cells of mice", *Int. Immunol.*, 10(9):1289-1298, 1998.
Challa et al., "FcRn: from molecular interactions to regulation of IgG pharmacokinetics and functions", *Curr Top Microbiol Immunol.*, 382:249-272, 2014.
Chames et al., "Direct selection of a human antibody fragment directed against the tumor T-cell epitope HLA-A1—MAGE-A1 from a nonimmunized phage-Fab library", *Proc. Natl. Acad. Sci. USA*, 97:7969-7974, 2000.
Cooper et al., "The contribution of cell surface FcRn in monoclonal antibody serum uptake from the intestine in suckling rat pups", *Front. Pharmacol.* 5, 225, 2014.
Dall'Acqua et al., "Increasing the affinity of a human IgG1 for the neonatal Fc receptor: biological consequences", *J Immunol.*, 169(9):5171-5180, 2002.
Datta-Mannan et al., "FcRn affinity-pharmacokinetic relationship of five human IgG4 antibodies engineered for improved in vitro FcRn binding properties in cynomolgus monkeys", *Drug Metab. Dispos.* 40, 1545-1555, 2012.
Datta-Mannan et al., "Humanized IgG1 variants with differential binding properties to the neonatal Fc receptor: relationship to pharmacokinetics in mice and primates", *Drug Metab. Dispos.* 35:86-94, 2007.
Deng et al., "Pharmacokinetics of humanized monoclonal anti-tumor necrosis factor-α antibody and its neonatal Fc receptor variants in mice and cynomolgus monkeys", *Drug Metab. Dispos.* 38, 600-605, 2010.

(Continued)

*Primary Examiner* — Chun W Dahle
(74) *Attorney, Agent, or Firm* — Parker Highlander PLLC

(57) ABSTRACT

In some aspects, mutant or variant Fc domains are provided that exhibit increased binding to FcRn and increased half-life after administration in vivo. The Fc domain may be comprised in a glycosylated or aglycosylated antibody. Methods for using the mutant or variant Fc domains or polypeptides comprising the mutant or variant Fc domains are also provided.

41 Claims, 29 Drawing Sheets

Specification includes a Sequence Listing.

(56) References Cited

OTHER PUBLICATIONS

Desai et al., "Characterization of human anti-high molecular weight-melanoma-associated antigen single-chain Fv fragments isolated from a phage display antibody library", *Cancer Res.*, 58:2417-2425, 1998.
Dickinson et al., "Bidirectional FcRn-dependent IgG transport in a polarized human intestinal epithelial cell line", *J. Clin. Investig.* 104, 903-911, 1999.
Elvin et al., "Therapeutic antibodies: market considerations, disease targets and bioprocessing", *Int. J. Pharm.*, 440:83-98, 2013.
Extended European Search Report issued in European application No. 18844094.5, dated Apr. 21, 2021.
Firan et al., "The MHC class I-related receptor, FcRn, plays an essential role in the maternofetal transfer of γ-globulin in humans", *Int. Immunol.* 13, 993-1002, 2001.
Gan et al., "Analyses of the recycling receptor, FcRn, in live cells reveal novel pathways for lysosomal delivery", *Traffic.*, 10(5):600-14, 2009.
Ghetie and Ward, "Abnormally short serum half-lives of IgG in β2-microglobulin-deficient mice", *Eur. J. Immunol.*, 26:690-696, 1996.
Ghetie and Ward, "Multiple roles for the major histocompatibility complex class I—related receptor FcRn", *Annu. Rev. Immunol.*, 18:739-766, 2000.
Griffiths and Duncan, "Strategies for selection of antibodies by phage display", *Curr. Opin. Biotechnol.*, 9:102-108, 1998.
Harvey et al., "Anchored periplasmic expression, a versatile technology for the isolation of high-affinity antibodies from *Escherichia coli*-expressed libraries", *Proc. Natl. Acad. Sci. USA*, 101:9193-9198, 2004.
Harvey et al., "Engineering of recombinant antibody fragments to methamphetamine by anchored periplasmic expression", *J. Immunol. Methods.* 308:43-52, 2006.
Haymann et al., "Characterization and localization of the neonatal Fc receptor in adult human kidney", *J. Am. Soc. Nephrol.* 11, 632-639, 2000.
Hinton et al., "An engineered human IgG1 antibody with longer serum half-life", *J. Immunol.* 176, 346-356, 2006.
Hinton et al., "Engineered human IgG antibodies with longer serum half-lives in primates", *J. Biol. Chem.* 279, 6213-6216, 2004.
Hoogenboom and Winter, "By-passing immunisation: human antibodies from synthetic repertoires of germline VH gene segments rearranged in vitro", *J. Mol. Biol.*, 227:381-388, 1992.
Hoogenboom et al., "Antibody phage display technology and its applications", *Immunotechnology*, 4:1-20, 1998.
Ingegnoli et al., "Rheumatoid factors: clinical applications", *Disease Markers*, 35(6), 727-734, 2013.
International Search Report and Written Opinion issued in corresponding PCT Application No. PCT/US2018/046398, dated Nov. 6, 2018.
Israel et al., "Expression of the neonatal Fc receptor, FcRn, on human intestinal epithelial cells", *Immunology* 92, 69-74, 1997.
Israel et al., "Increased clearance of IgG in mice that lack β2-microglobulin: possible protective role of FcRn", *Immunology.* 89(4):573-578, 1996.
Jayeway et al., "Structure of the Antibody Molecule and Immunoglobulin Genes", Immunology Third Edition, Garland Publishing Inc, 3:1-13:11, 1997.
Jefferis, "Glycosylation of natural and recombinant antibody molecules", *Adv. Exp. Med. Biol.*, 564:143-148, 2005.
Jung et al., "Aglycosylated IgG variants expressed in bacteria that selectively bind FcγRI potentiate tumor cell killing by monocyte-dendritic cells", *Proc. Natl. Acad. Sci. USA*, 107:604-609, 2010.

Jung et al., "Effective phagocytosis of low Her2 tumor cell lines with engineered, aglycosylated IgG displaying high FcγRIIa affinity and selectivity", *ACS Chem. Biol.*, 8:368-375, 2013.
Kim et al., "Mapping the site on human IgG for binding of the MHC class I-related receptor, FcRn", *Eur J Immunol.*, 29(9):2819-2825, 1999.
Kjaer et al., "Glycerol diversifies phage repertoire selections and lowers non-specific phage absorption", *FEBS Lett.*, 431:448-452, 1998.
Ko et al., "Enhanced neonatal Fc receptor function improves protection against primate SHIV infection", *Nature.* 514, 642-645, 2014.
Lee et al., "IgG Fc domains that bind C1q but not effector Fcγ receptors delineate the importance of complement-mediated effector functions", *Nat Immunol.*, 18(8), 889-898, 2017.
Lee et al., "An engineered human Fc domain that behaves like a pH-toggle switch for ultra-long circulation persistence," *Nature Communications*, 10(1):5031, pp. 1-11, 2019.
Maeda et al., "Identification of human IgG1 variant with enhanced FcRn binding and without increased binding to rheumatoid factor autoantibody", *mAbs*, 9(5):844-853, 2017.
Martin et al., "Crystal structure at 2.8 Å of an FcRn/heterodimeric Fc complex: mechanism of pH-dependent binding", *Mol Cell.*, 7(4):867-877, 2001.
Newkirk, "Rheumatoid factors: host resistance or autoimmunity?", *Clinical Immunology*, 104(1), 1-13, 2002.
Ober et al., "Exocytosis of IgG as mediated by the receptor, FcRn: an analysis at the single-molecule level", *Proc. Natl. Acad. Sci. USA*, 101:11076-11081, 2004.
Ober et al., "Visualizing the site and dynamics of IgG salvage by the MHC class I-related receptor, FcRn", *J. Immunol.*, 172:2021-2029, 2004.
Robbie et al., "A novel investigational Fc modified humanized monoclonal antibody, Motavizumab-YTE, has an extended half-life in healthy adults: a randomized study", *Antimicrob. Agents Chemother.* 57, 6147-6153, 2013.
Roopenian and Akilesh, "FcRn: the neonatal Fc receptor comes of age", *Nat Rev Immunol.*, 7(9):715-725, 2007.
Roopenian et al., "The MHC class I-like IgG receptor controls perinatal IgG transport, IgG homeostasis, and fate of IgG-Fc-coupled drugs", *J Immunol.* 170(7):3528-3533, 2003.
Rudikoff et al., "Single amino acid substitution altering antigen-binding specificity", Proc. Natl. Acad. Sci., 79:1979-1983, Mar. 1982.
U.S. Appl. No. 62/540,692, entitled "Interleukin-21 muteins and methods of treatment," by Khaled M.K.Z. Ali et al., filed Aug. 3, 2017.
Walters et al., "Conformational destabilization of immunoglobulin G increases the low pH binding affinity with the neonatal Fc receptor", *J Biol Chem.*, 291(4):1817-25. 2016.
Wang et al., "Monoclonal antibodies with identical Fc sequences can bind to FcRn differentially with pharmacokinetic consequences", *Drug Metab. Dispos.* 39, 1469-1477, 2011.
Ward et al., "Targeting FcRn for the modulation of antibody dynamics", *Mol Immunol.*, 67(2):131-141, 2015.
Yeung et al., "A therapeutic anti—VEGF antibody with increased potency independent of pharmacokinetic half-life", *Cancer Res.* 70, 3269-3277, 2010.
Yeung et al., "Engineering human IgG1 affinity to human neonatal Fc receptor: impact of affinity improvement on pharmacokinetics in primates", *J. Immunol.* 182, 7663-7671, 2009.
Yu et al., "Engineering hydrophobic protein-carbohydrate interactions to fine-tune monoclonal antibodies", *J. Am. Chem. Soc.*, 135(26):9723-9732, 2013.
Zalevsky et al., "Enhanced antibody half-life improves in vivo activity", *Nat. Biotechnol.* 28, 157-159, 2010.
Zheng et al., "Translational pharmacokinetics and pharmacodynamics of an FcRn-variant anti-CD4 monoclonal antibody from preclinical model to phase I study", *Clin. Pharmacol. Ther.* 89, 283-290, 2011.

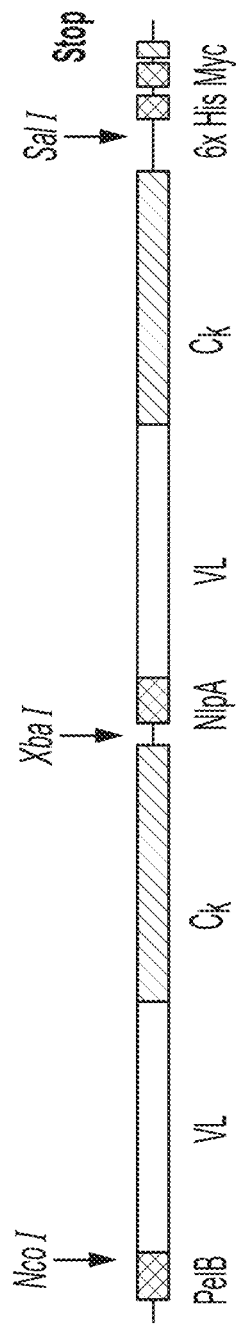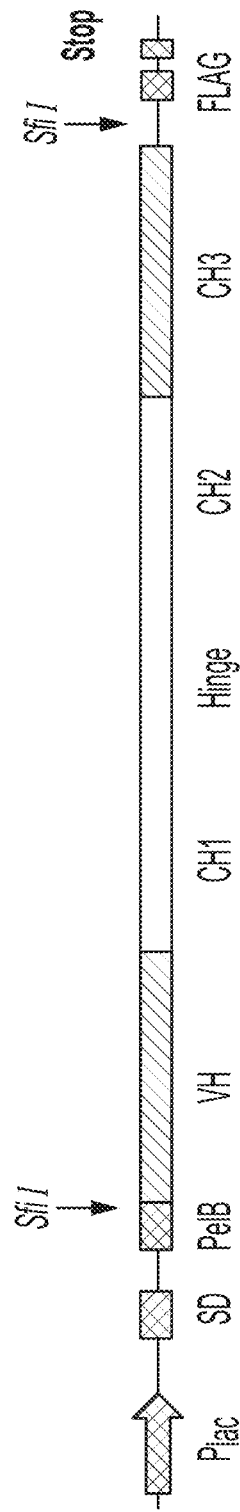

B   Sort   Resort
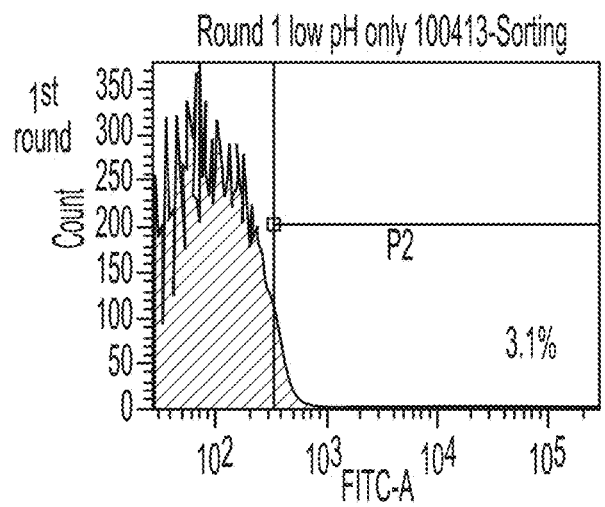
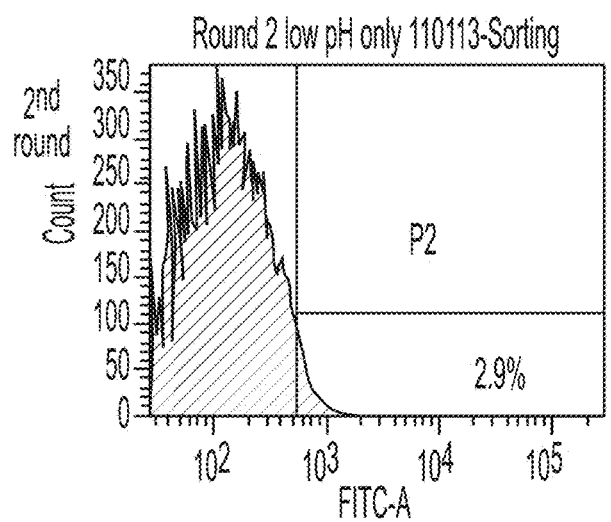
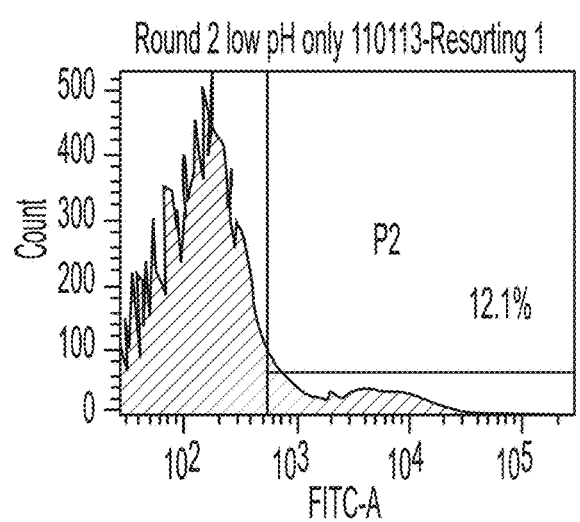
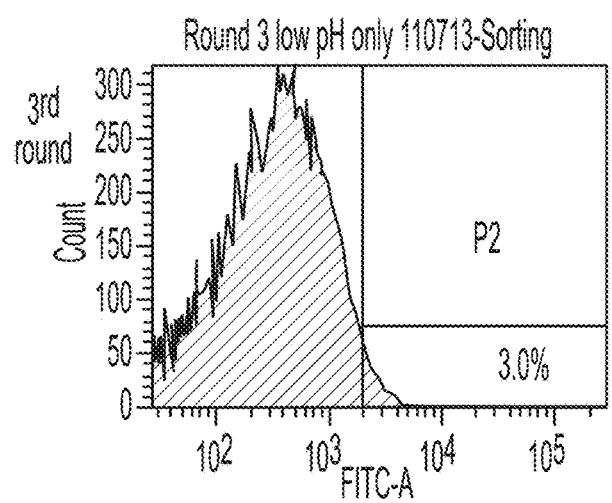
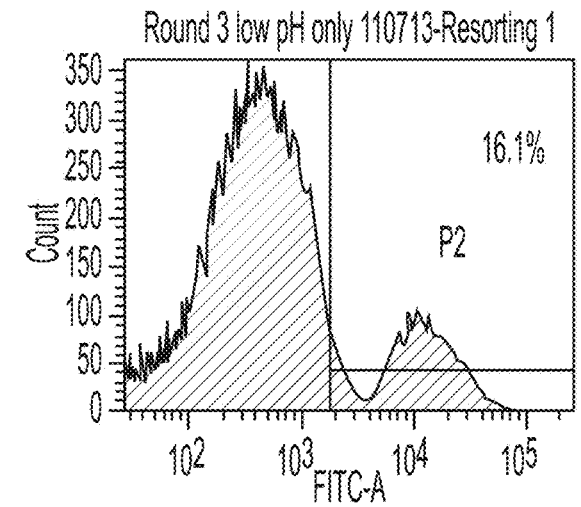
FIG. 3B

Low density

Medium density

FIG. 16C
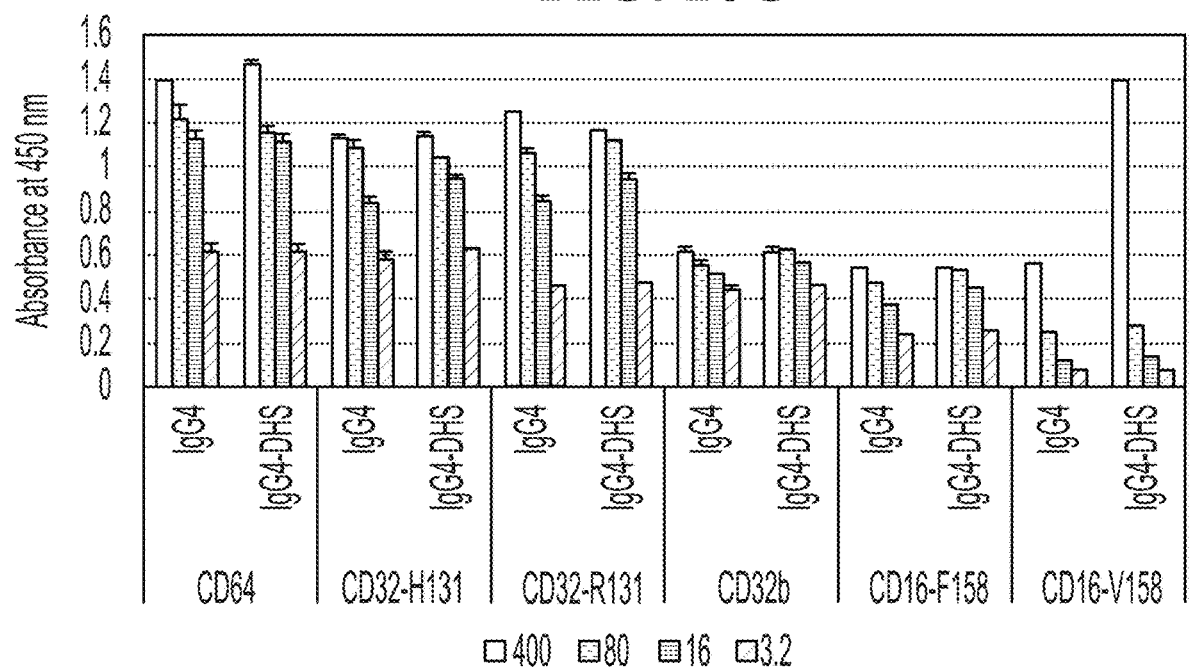
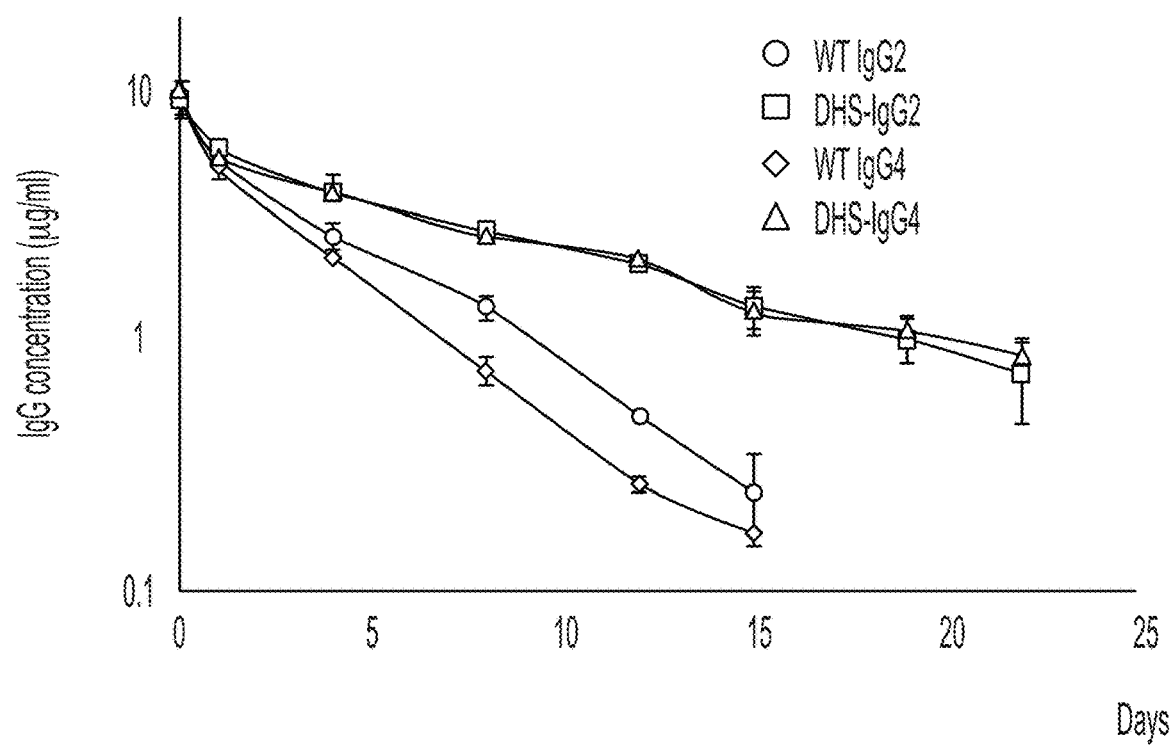
FIG. 17

SEQUENCE LISTING

```
<160> NUMBER OF SEQ ID NOS: 23

<210> SEQ ID NO 1
<211> LENGTH: 232
<212> TYPE: PRT
<213> ORGANISM: Homo sapiens

<400> SEQUENCE: 1

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125
```

```
Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Lys
225                 230
```

<210> SEQ ID NO 2
<211> LENGTH: 228
<212> TYPE: PRT
<213> ORGANISM: Homo sapiens

<400> SEQUENCE: 2

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
50              55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
            130                 135                 140

Ser Leu Thr Cys Leu Val Lys Gly Phe Tyr Pro Ser Asp Ile Ser Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
210                 215                 220

Ser Pro Gly Lys
225
```

<210> SEQ ID NO 3
<211> LENGTH: 279
<212> TYPE: PRT
<213> ORGANISM: Homo sapiens -continued

<400> SEQUENCE: 3

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn His Phe Thr Gln Lys Ser
            260                 265                 270

Leu Ser Leu Ser Pro Gly Lys
        275

<210> SEQ ID NO 4
<211> LENGTH: 229
<212> TYPE: PRT
<213> ORGANISM: Homo sapiens

<400> SEQUENCE: 4

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

```
Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys
225
```

<210> SEQ ID NO 5
<211> LENGTH: 232
<212> TYPE: PRT
<213> ORGANISM: Artificial Sequence
<220> FEATURE:
<223> OTHER INFORMATION: Synthetic peptide

<400> SEQUENCE: 5

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Glu Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Asp His His
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205
```

Ser Cys Ser Val Met His Glu Ala Leu His Ser His Tyr Thr Gln Lys
    210                 215                 220

Ser Leu Ser Leu Ser Pro Gly Lys
225                 230

<210> SEQ ID NO 6
<211> LENGTH: 232
<212> TYPE: PRT
<213> ORGANISM: Artificial Sequence
<220> FEATURE:
<223> OTHER INFORMATION: Synthetic peptide

<400> SEQUENCE: 6

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Glu Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Asp His His
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Tyr His Tyr Thr Gln Lys
    210                 215                 220

Ser Leu Ser Leu Ser Pro Gly Lys
225                 230

<210> SEQ ID NO 7
<211> LENGTH: 232
<212> TYPE: PRT
<213> ORGANISM: Artificial Sequence
<220> FEATURE:
<223> OTHER INFORMATION: Synthetic peptide

<400> SEQUENCE: 7

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

```
Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Asp His His
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Ser His Tyr Thr Gln Lys
210                 215                 220

Ser Leu Ser Leu Ser Pro Gly Lys
225                 230

<210> SEQ ID NO 8
<211> LENGTH: 232
<212> TYPE: PRT
<213> ORGANISM: Artificial Sequence
<220> FEATURE:
<223> OTHER INFORMATION: Synthetic peptide

<400> SEQUENCE: 8

Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Asp His His
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160
```

-continued

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Tyr Thr Gln Lys
    210                 215                 220

Ser Leu Ser Leu Ser Pro Gly Lys
225                 230
```

<210> SEQ ID NO 9
<211> LENGTH: 228
<212> TYPE: PRT
<213> ORGANISM: Artificial Sequence
<220> FEATURE:
<223> OTHER INFORMATION: Synthetic peptide

<400> SEQUENCE: 9

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Asp His His Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ser Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Ser His Tyr Thr Gln Lys Ser Leu Ser Leu
    210                 215                 220

Ser Pro Gly Lys
225
```

<210> SEQ ID NO 10
<211> LENGTH: 279
<212> TYPE: PRT
<213> ORGANISM: Artificial Sequence
<220> FEATURE:
<223> OTHER INFORMATION: Synthetic peptide -continued

```
<400> SEQUENCE: 10

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
                100                 105                 110

Gly Val Glu Val His Asn Ala Lys Thr Lys Pro Arg Glu Glu Gln Tyr
            115                 120                 125

Asn Ser Thr Phe Arg Val Val Ser Val Leu Thr Val Asp His His Asp
        130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Ser His Phe Thr Gln Lys Ser
            260                 265                 270

Leu Ser Leu Ser Pro Gly Lys
        275

<210> SEQ ID NO 11
<211> LENGTH: 229
<212> TYPE: PRT
<213> ORGANISM: Artificial Sequence
<220> FEATURE:
<223> OTHER INFORMATION: Synthetic peptide

<400> SEQUENCE: 11

Glu Ser Lys Tyr Gly Pro Pro Cys Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60
```

```
            Glu Val His Asn Ala Lys Thr Lys Pro Arg Glu Gln Phe Asn Ser
            65                  70                  75                  80

Thr Tyr Arg Val Val Ser Val Leu Thr Val Asp His His Asp Trp Leu
                            85                  90                  95

Asn Gly Lys Glu Tyr Lys Cys Lys Val Ser Asn Lys Gly Leu Pro Ser
                        100                 105                 110

Ser Ile Glu Lys Thr Ile Ser Lys Ala Lys Gly Gln Pro Arg Glu Pro
                    115                 120                 125

Gln Val Tyr Thr Leu Pro Pro Ser Gln Glu Glu Met Thr Lys Asn Gln
                130                 135                 140

Val Ser Leu Thr Cys Leu Val Lys Gly Phe Tyr Pro Ser Asp Ile Ala
            145                 150                 155                 160

Val Glu Trp Glu Ser Asn Gly Gln Pro Glu Asn Asn Tyr Lys Thr Thr
                            165                 170                 175

Pro Pro Val Leu Asp Ser Asp Gly Ser Phe Phe Leu Tyr Ser Arg Leu
                        180                 185                 190

Thr Val Asp Lys Ser Arg Trp Gln Glu Gly Asn Val Phe Ser Cys Ser
                    195                 200                 205

Val Met His Glu Ala Leu His Ser His Tyr Thr Gln Lys Ser Leu Ser
                210                 215                 220

Leu Ser Leu Gly Lys
            225

<210> SEQ ID NO 12
<211> LENGTH: 40
<212> TYPE: DNA
<213> ORGANISM: Artificial Sequence
<220> FEATURE:
<223> OTHER INFORMATION: Synthetic primer

<400> SEQUENCE: 12
gttattactc gcggcccagc cggccatggc ggaggttcaa                          40

<210> SEQ ID NO 13
<211> LENGTH: 27
<212> TYPE: DNA
<213> ORGANISM: Artificial Sequence
<220> FEATURE:
<223> OTHER INFORMATION: Synthetic primer

<400> SEQUENCE: 13
cttgggtttt gggggggaaga ggaagac                                       27

<210> SEQ ID NO 14
<211> LENGTH: 72
<212> TYPE: DNA
<213> ORGANISM: Artificial Sequence
<220> FEATURE:
<223> OTHER INFORMATION: Synthetic primer

<400> SEQUENCE: 14
gtcttcctct tccccccaaa acccaagvrk vmbcdcvwbv whvrkvrkac ccctgaggtc    60
acatgcgtgg tg                                                        72

<210> SEQ ID NO 15
<211> LENGTH: 72
<212> TYPE: DNA
<213> ORGANISM: Artificial Sequence
<220> FEATURE:
<223> OTHER INFORMATION: Synthetic primer
```

<400> SEQUENCE: 15
gaccttgcac ttgtactcct tgccattghg ccamybghgg tgvwsvwsgg tgaggacgct    60
gaccacacgg ta    72

<210> SEQ ID NO 16
<211> LENGTH: 27
<212> TYPE: DNA
<213> ORGANISM: Artificial Sequence
<220> FEATURE:
<223> OTHER INFORMATION: Synthetic primer

<400> SEQUENCE: 16
aatggcaagg agtacaagtg caaggtc    27

<210> SEQ ID NO 17
<211> LENGTH: 75
<212> TYPE: DNA
<213> ORGANISM: Artificial Sequence
<220> FEATURE:
<223> OTHER INFORMATION: Synthetic primer

<400> SEQUENCE: 17
cggggacagg gagaggctct tmybcgtgtv gtgmybgtgg hgagcmybat gcatcacgga    60
gcatgagaag acgtt    75

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18
aagagcctct ccctgtcccc g    21

<210> SEQ ID NO 19
<211> LENGTH: 40
<212> TYPE: DNA
<213> ORGANISM: Artificial Sequence
<220> FEATURE:
<223> OTHER INFORMATION: Synthetic primer

<400> SEQUENCE: 19
gcggccgcga attcggcccc cgaggcccct ttacccgggg    40

<210> SEQ ID NO 20
<211> LENGTH: 54
<212> TYPE: DNA
<213> ORGANISM: Artificial Sequence
<220> FEATURE:
<223> OTHER INFORMATION: Synthetic primer

<400> SEQUENCE: 20
gtcgacaaga aagttgagcc caaatcttgc gacaaaactc acacatgccc accg    54

<210> SEQ ID NO 21
<211> LENGTH: 38
<212> TYPE: DNA
<213> ORGANISM: Artificial Sequence
<220> FEATURE:
<223> OTHER INFORMATION: Synthetic primer

<400> SEQUENCE: 21
ctcgagcggc cgctcattta cccggggaca gggagagg    38

```
<210> SEQ ID NO 22
<211> LENGTH: 16
<212> TYPE: DNA
<213> ORGANISM: Artificial Sequence
<220> FEATURE:
<223> OTHER INFORMATION: Synthetic primer

<400> SEQUENCE: 22
tgagcggccg ctcgag                                                      16

<210> SEQ ID NO 23
<211> LENGTH: 30
<212> TYPE: DNA
<213> ORGANISM: Artificial Sequence
<220> FEATURE:
<223> OTHER INFORMATION: Synthetic primer

<400> SEQUENCE: 23
gcaagatttg ggctcaactt tcttgtcgac                                       30
```

ENGINEERED ANTIBODY FC VARIANTS FOR ENHANCED SERUM HALF LIFE

This application is a divisional of U.S. application Ser. No. 16/101,421, filed Aug. 11, 2018, which claims the benefit of U.S. Provisional Patent Application No. 62/544,622, filed Aug. 11, 2017, the entirety of each of which is incorporated herein by reference.

The sequence listing that is contained in the file named "CLFRP0463USD1.txt", which is 26 KB (as measured in Microsoft Windows®) and was created on Jun. 6, 2021, is filed herewith by electronic submission and is incorporated by reference herein.

BACKGROUND OF THE INVENTION

1. Field of the Invention

The present invention relates generally to the field of protein engineering. More particularly, it concerns improved serum half life of Fc antibody domains conferring enhanced pH-dependent binding to FcRn.

2. Description of Related Art

Currently, the top 25 marketed recombinant therapeutic antibodies have sales of well over $43.5 billion/year, and with a forecasted annual growth rate of 9.2% from 2010 to 2015, they have been projected to increase to $62.7 billion/year by 2015 (Elvin et al., 2013). Monoclonal antibodies (mAbs) comprise the majority of recombinant proteins currently in the clinic, with 1064 products undergoing company-sponsored clinical trials in the USA or EU, of which 164 are phase III (Elvin et al., 2013). In terms of therapeutic focus, the mAb market is heavily focused on oncology and inflammatory disorders, and products within these therapeutic areas are set to continue to be the key growth drivers over the forecast period. As a group, genetically engineered mAbs generally have a higher probability of FDA approval success than small-molecule drugs. At least 50 biotechnology companies and all major pharmaceutical companies have active antibody discovery programs in place. The original method for isolation and production of mAbs was first reported at 1975 by Milstein and Kohler (Kohler and Milstein 1975), and it involved the fusion of mouse lymphocyte and myeloma cells, yielding mouse hybridomas. Therapeutic murine mAbs entered clinical study in the early 1980s; however, problems with lack of efficacy and rapid clearance due to patients' production of human anti-mouse antibodies (HAMA) became apparent. These issues, as well as the time and cost consumption related to the technology, became driving forces for the evolution of mAb production technology. Polymerase Chain Reaction (PCR) facilitated the cloning of monoclonal antibody genes directly from lymphocytes of immunized animals and the expression of combinatorial libraries of antibody fragments in bacteria (Orlandi et al., 1989). Later libraries were created entirely by in vitro cloning techniques using naive genes with rearranged complementarity determining region 3 (CDR3) (Griffiths and Duncan 1998; Hoogenboom et al., 1998). As a result, the isolation of antibody fragments with the desired specificity was no longer dependent on the immunogenicity of the corresponding antigen. These advantages have facilitated the development of antibody fragments to a number of unique antigens including small molecular compounds (haptens) (Hoogenboom and Winter 1992), molecular complexes (Chames et al., 2000), unstable compounds (Kjaer et al., 1998), and cell surface proteins (Desai et al., 1998).

One method for screening large combinatorial libraries of antibodies to identify clones that bind to a ligand with desired affinity involves expression and display of antibody fragments or full length antibodies on the surface of bacterial cells and more specifically E. coli. Cells displaying antibodies or antibody fragments are incubated with a solution of fluorescently labeled ligand and those cells that bind said ligand by virtue of the displayed antibody on their surface are isolated by flow cytometry. In particular, Anchored Periplasmic Expression (APEx) is based on anchoring the antibody fragment on the periplasmic face of the inner membrane of E. coli followed by disruption of the outer membrane, incubation with fluorescently-labeled target, and sorting of the spheroplasts (U.S. Pat. No. 7,094,571, Harvey et al., 2004; Harvey et al., 2006).

Among human serum proteins, albumin and immunoglobulin G (IgG) have longer serum half life (~three weeks) than other serum proteins in human. The neonatal Fc receptor (FcRn) is known to play a number of important biological functions, such as recycling and transcytosis process, leading to an extraordinarily long, ~21 days serum persistence of IgG in humans (Challa et al., 2014). Such intercellular trafficking of IgG can regulate its homeostasis, resulting in reduced clearance and increased half-life in vivo by preventing IgG intracellular degradation (Ober et al., 2004; Ward et al., 2015). In almost all cell types, FcRn is primarily localized to intracellular vesicles such as early and recycling endosomes and sorting tubules and the expression level of FcRn is limited on the cell surface (Ober et al., 2004). In addition, IgG-FcRn interactions are optimal at acidic pH, but are lost at neutral pH. Thus, the commonly accepted FcRn-mediated IgG recycling model is that IgG is internalized via non-specific pinocytosis, and IgG binds to FcRn at acidic endosomes (~pH 6.0) and is recovered back to the cell surface (physiological pH 7.4), to maintain high serum levels of IgG in the blood (Ghetie et al., 1996; Ghetie and Ward, 2000; Israel et al., 1996; Kim et al., 1999; Martin et al., 2001; Roopenian and Akilesh, 2007; Roopenian et al., 2003). However, IgGs that do not dissociate from FcRn at cell surface are destined for lysosomal degradation, since it is either recovered from transport to the lysosome or are catabolized during receptor turnover (Gan et al., 2009).

Due to the physiological importance of Fc binding to FcRn and the importance of Fc binding to FcRn with therapeutic antibodies, there is a clear need for new Fc domains that have an increased serum half life by enhanced pH-dependent binding for FcRn.

SUMMARY OF THE INVENTION

In some aspects, the present invention overcomes limitations in the prior art by providing Fc domain variants which display enhanced pH-dependent affinity for FcRn. As shown in the below examples, engineered mutant IgG Fc domains are provided that both bind to FcRn with affinities far exceeding that of human IgG wild-type at acidic pH, and in some aspects the mutant Fc domains were further observed to have very low to negligible or undetectable binding to FcRn at physiological pH (physiological pH 7.4). Such high pH-selectivity for affinity for FcRn is very desirable for increasing serum half-life.

In some aspects of the present invention, methods are provided for isolating antibody Fc domains that display enhanced affinity at acidic pH and pH-selectivity for FcRn. In another aspect of the present invention, specific mutations and combinations of mutations in IgG1 Fc domains are provided that can result in pH-selective binding and/or increased affinity to FcRn.

More specifically, in some embodiments, mutant or variant human Fc domains are provided that, as compared to a corresponding wild-type Fc domain, exhibit: (i) enhanced binding at pH 5.8 and (ii) reduced binding or no detectable binding at pH 7.4 for FcRn. The mutant or variant Fc domain may be a mutant or variant IgG domain. The mutant or variant Fc domain may be comprised in a polypeptide, such as an antibody. In some embodiments, the mutant or variant Fc domain may be comprised in a therapeutic antibody such as, e.g., an agonistic or antagonistic antibody. In some embodiments, there are compositions involving a polypeptide that has a mutant or variant Fc domain derived from a human IgG1-4 antibody ("antibody Fc domain"). The mutant Fc domain may be a variant of the wild-type human IgG1 Fc domain (SEQ ID NO: 1), wherein the mutant or variant Fc domain enables binding to FcRn with increased affinity at acidic pH and not at neutral pH. In some embodiments, the engineered Fc domain may display increased affinity for FcRn of, e.g., of about 5-fold greater than a glycosylated wild-type Fc domain. In further embodiments, mutant human Fc domains are provided of all the other wild-type IgG subclasses (human IgG2, IgG3, and IgG4) are provided and enable binding to FcRn with increased affinity at acidic pH and not at neutral pH. The mutant or variant Fc domain may contain the mutations (L/V309D, Q311H, N434S/Y), and optionally (V264E), relative to a wild-type human IgG1 Fc (SEQ ID NO:1), human IgG2 Fc (SEQ ID NO:2), human IgG3 Fc (SEQ ID NO:3), or a human IgG4 Fc (SEQ ID NO:4), in order to increase the binding of the mutant or variant Fc to FcRn at acidic pH (e.g., pH 5.8), but not at physiological pH (pH 7.4). For example, mutations (L/V309D, Q311H, N434S) were made in human IgG1, IgG2, IgG3, and IgG4, resulting in SEQ ID NO:7, SEQ ID NO:9, SEQ ID NO:10, and SEQ ID NO:11, respectively. As noted above, these changes in binding to FcRn at acidic pH can improve the pharmacokinetics of the protein and/or increase serum half-life. As observed in the below examples, the engineered Fc domain were observed to display enhanced serum half-life in a human FcRn transgenic mouse model.

In some aspects, methods are provided for isolating antibody Fc domains that display increased affinity and pH-selectivity for FcRn. The antibody Fc domains may comprise one or more or the specific substitution mutations or combinations of substitution mutations as described herein, e.g., to affect binding or selectively and with increased affinity of the Fc domain to FcRn.

In some embodiments, there are compositions involving a polypeptide that has an Fc domain from a human IgG1 antibody ("antibody Fc domain"). In additional embodiments, the Fc domain is a variant or mutant of the human IgG1 Fc domain (SEQ ID NO: 1) that can display increased or pH-selective binding to FcRn. In some embodiments, the amino acid substitutions of engineered Fc domain (mutations L/V309D, Q311H, and N434S/Y; and optionally V264E), when introduced into other IgG subclasses (IgG2, IgG3, and IgG4), result in both (i) pH-selectively in binding to FcRn and (ii) enhanced binding to FcRn at acidic pH. In some embodiments, the engineered Fc domains provided herein may display increased affinity for FcRn of 3-fold to 5-fold or greater (e.g., at least 2, 2.5, 3, 3.5, 4, 4.5, 5, or 5.5-fold higher enhanced $K_D$ for FcRn), as compared to a polypeptide having a wild-type Fc domain.

An antibody Fc domain may be the Fc domain of an IgG antibody or a variant thereof. Furthermore, the antibody Fc domain may be defined as a human Fc domain. In certain aspects, the Fc domain may be an IgG1 Fc domain, such as the Fc domain of an anti-HER2 antibody. It is also contemplated that a polypeptide may comprise a fusion of an engineered Fc domain as disclosed herein fused to a polypeptide not derived from an antibody molecule.

In some embodiments, a polypeptide comprising an antibody Fc domain comprises particular amino acid substitutions. In some embodiments, there are multiple amino acid substitutions at one of more positions from the following list: (264, 309, 311, and 434); (309, 311, and 434) in some embodiments, the engineered Fc domain may have a substitution mutation at 2, 3, 4 or all of these positions. The Fc domain may be glycosylated or aglycosylated. For example, inclusion of a mutation at position 264 (e.g.,V264E) can result in an aglycosylated Fc domain. In some embodiments, antibody Fc domain of IgG1 may a substitution at amino acid 309 by aspartate (L309D), a substitution at amino acid 311 to histidine (Q311H), a substitution at amino acid 434 to serine or tyrosine (N434S/Y), or combinations of these substitutions thereof. Optionally, the Fc domain IgG1 may further comprise a substitution at amino acid 264 to glutamate (V264E),In other preferred embodiments, antibody Fc domain (such as an Fc domain of a IgG2, IgG3, or IgG4) may comprise a substitution at amino acid 309 by aspartate (V309D), a substitution at amino acid 311 to histidine (Q311H), a substitution at amino acid 434 to serine or tyrosine (N434S/Y), or combinations of these substitutions thereof. Optionally, the Fc domain IgG1 may further comprise a substitution at amino acid 264 to glutamate (V264E).

An aspect of the present invention relates to a polypeptide comprising an mutant or variant human IgG Fc domain capable of binding human FcRn at an acidic pH, wherein the Fc domain has substitution mutations of: (i) aspartic acid at position 309 (L/V309D); (ii) histidine at position 311 (Q311H); and (iii) a substitution mutation at position 434 (N434). The substitution mutation at position 434 may be serine (N434S) or tyrosine (N434Y). The Fc domain may be glycosylated. In some embodiments, the Fc domain has substantially equivalent, essentially the same, about the same, or the same binding to FcγR as compared to wild-type. In some embodiments, the Fc domain has a binding capacity that is substantially equivalent, essentially the same, about the same, the same as, or equivalent to 1, 2, or all of FcγRI, FcγRII, and FcγRIII, as compared to wild-type. The Fc domain may bind FcRn at an acidic pH with an affinity higher than the wild-type. In some embodiments, the Fc domain does not detectably or selectively bind to FcRn, or exhibits no or essentially no binding to FcRn, at neutral pH. In some embodiments, the Fc domain exhibits: (i) enhanced binding at pH 5.8 and (ii) reduced binding or no detectable binding at pH 7.4 for FcRn, as compared to the wild-type. The Fc domain may be aglycosylated. For example, in some embodiments, the Fc domain has a substitution mutation of glutamic acid at position 264 (V264E). The IgG may be IgG1, IgG2, IgG3, or IgG4. In some embodiments, the Fc domain comprises or consists of: EDHS (V264E, L309D, Q311H, and N434S; e.g., SEQ ID NO: 5), EDHY (V264E, L309D, Q311H, and N434Y; e.g., SEQ ID NO: 6), DHS (L309D, Q311H, and N434S; e.g., SEQ ID NO: 7), DHY (L309D, Q311H, and N434Y; e.g., SEQ ID NO: 8), IgG2-DHS (V309D, Q311H, and N434S; SEQ ID NO: 9), IgG3-DHS (L309D, Q311H, and N434S; SEQ ID NO: 10), or IgG4-DHS (L309D, Q311H, and N434S; SEQ ID NO: 11). In some embodiments, the Fc domain comprises or consists of: DHS (L309D, Q311H, and N434S; e.g., SEQ ID NO: 7) or DHY (L309D, Q311H, and N434Y; e.g., SEQ ID NO: 8). In some embodiments, the Fc domain binds FcRn with a $K_D$ value of less than about 550, 525, 500, 475, 450, 425, 400, 375, 350, 325, 300, 275, 250, 225, 200, 175, 150, 125, or 100 nM (e.g., at pH 5.8). The polypeptide may further comprise a non-Fc receptor (non-FcR) binding domain. The non-FcR binding domain may be an Ig variable domain. The polypeptide may be a full-length antibody. In some embodiments, the antibody is an agonistic antibody or an antagonistic antibody. In some embodiments, the antibody selectively binds Her2/neu, CD20, CD40, IL-10, 4-1BB, PD-1, PD-L1, CTLA-40X40, IL-1, IL-6, IL6R, TNFα, RANKL, EGFR, c-Met, Cd11a, VEGF-A, VEGFR1, VEGFR2, C5, or Integrain-α4. The antibody may be chemically conjugated to or covalently bound to a toxin. In some embodiments, the non-FcR binding region is not an antigen binding site of an antibody. In some embodiments, the non-FcR binding region binds a cell-surface protein. In some embodiments, the non-FcR binding regions binds a soluble protein.

Another aspect of the present invention relates to a nucleic acid encoding any of the polypeptides of the present invention or as described above. The nucleic acid may be a DNA segment. In some embodiments, the nucleic acid is an expression vector.

Yet another aspect of the present invention relates to a host cell comprising the nucleic acid of the present invention or as described above. The cell may express the nucleic acid.

Another aspect of the present invention relates to a method for preparing a polypeptide comprising: a) obtaining a host cell of the present invention or as describe above; b) incubating the host cell in culture under conditions to promote expression of the aglycosylated polypeptide; and c) purifying the expressed polypeptide from the host cell. In some embodiments, the host cell is a prokaryotic cell or a mammalian cell.

Yet another aspect of the present invention relates to a pharmaceutical formulation comprising a polypeptide of the present invention or as described above, or a nucleic acid of the present invention or as described above in a pharmaceutically acceptable carrier.

Another aspect of the present invention relates to a method of binding a protein in a subject comprising providing to the subject an antibody, wherein the antibody binds the protein, and comprises an Fc domain of the present invention or as described above. In some embodiments, the antibody is capable of specifically binding human FcRn with a $K_D$ of less than about 550, 525, 500, 475, 450, 425, 400, 375, 350, 325, 300, 275, 250, 225, 200, 175, 150, 125, or 100 nM. In some embodiments, the antibody is glycosylated, and wherein the Fc domain has about equivalent or equivalent binding of FcγRI, FcγRII, and FcγRIII, as compared to wild-type. In some embodiments, the antibody is a glycosylated therapeutic antibody. In some embodiments, the antibody is an aglycosylated version of a therapeutic antibody.

Yet another aspect of the present invention relates to a method of treating a subject having a disease comprising administering to the subject an effective amount of the formulation of the present invention or as described above. The method may induce antibody-dependent cytotoxicity. In some embodiments, The disease is a cancer, an infection, or an autoimmune disease (e.g., rheumatoid arthritis). The subject may be a human patient. The formulation may be administered intratumorally, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage. In some embodiments, the disease is a cancer, and wherein the method further comprises administering at least a second anticancer therapy to the subject. The second anticancer therapy may be a surgical therapy, chemotherapy, radiation therapy, cryotherapy, hormone therapy, immunotherapy or cytokine therapy. The disease may comprise a tumor such as, e.g., a solid tumor or a hematological tumor.

In one embodiment, a composition comprising a variant Fc domain of the present embodiments or a nucleic acid encoding a variant Fc domain of the present embodiments is provided for use in the treatment of a disease (e.g., cancer, an infection, an autoimmune disease, a bacterial infection, or a viral infection). Treating the disease may involve binding a select protein to achieve a therapeutic effect (e.g., resulting from binding of a toxin, or stimulation of a receptor with an agonistic antibody, etc.) while generating a reduced immune activation or reduced complement dependent cytotoxicity. In some aspects, the disease may be a cancer, an autoimmune disease, an inflammatory disease, or an infectious disease. In another embodiment, the use of a polypeptide according to the present embodiments or a nucleic acid encoding a polypeptide according to the present embodiments in the manufacture of a medicament for the treatment of a disease such as cancer is provided.

In some embodiments, a pharmaceutically acceptable composition comprising a polypeptide in accordance with the present invention or as described above and a pharmaceutically acceptable excipient are provided. In some embodiments, a composition for use in a method of treating a disease in a subject in need thereof, said composition comprising a polypeptide in accordance with the present invention or as described above, is provided. The disease may be a cancer, an infection, a bacterial infection, a viral infection, or an autoimmune disease.

A variant Fc domain polypeptide (also referred to as a mutant or engineered Fc domain) may be characterized as having a certain percentage of identity as compared to an unmodified polypeptide (e.g., a wild-type Fc domain polypeptide, such as a wild-type IgG Fc domain, or a human wild-type IgG Fc domain) or to any polypeptide sequence disclosed herein. The percentage identity may be about, at least 80%, 85%, 90%, 95%, 96%, 97%, 98%, 99%, 99.5%, or 100% (or any range derivable therein) between the unmodified portions of a modified polypeptide (i.e., the sequence of the modified polypeptide excluding any specified substitutions) and the corresponding wild-type polypeptide. For example, a variant Fc domain may have, e.g., at least 90%, at least about 95%, at least 99%, or 100% sequence identity as compared to a wild-type Fc domain (e.g., a wild-type human IgG Fc domain, such as any one of SEQ ID NOs:1-4) for regions of the variant Fc domain excluding specified substitution mutations (e.g., L/V309D, Q311H, and N434S/Y; and optionally V264E). The variant Fc domain may contain additional mutations, as compared to a wild-type Fc domain, in addition to the specified substitution mutations in the mutant Fc domain. It is also contemplated that percentage of identity discussed above may relate to the entirety of a variant Fc domain polypeptide as compared to a wild-type Fc domain (e.g., a human IgG Fc domain). For example, a variant Fc domain polypeptide characterized as having at least 90% identity to a wild-type Fc domain means that at least 90% of the amino acids in that variant polypeptide are identical to the amino acids in the wild-type polypeptide.

An antibody Fc domain may be a a mutant or variant Fc domain of a human IgG antibody (e.g., the Fc domain may be a human IgG1, IgG2, IgG3, or IgG4 Fc domain). It is also contemplated that a polypeptide may comprise a fusion of an engineered variant Fc domain as disclosed herein fused to a polypeptide not derived from an antibody molecule. In some embodiments, an engineered Fc domain of the present invention is comprised in an agonistic antibody such as, e.g., an antibody targeting CD40, death receptor 5 (DR5), PD-1, or a TNF receptor (TNFR) molecule.

Polypeptides comprising a variant Fc domain described herein may include a linker in some embodiments. In further embodiments, the linker is a conjugatable linker. In some embodiments, the polypeptide contains an Fc domain from an antibody. It may contain other regions from an antibody, such as another binding domain. The additional binding domain may not be not an FcR binding domain in some embodiments. In some embodiments, the polypeptide may contain an antigen binding site or domain from an antibody, such as all or part of the variable region from an antibody. The polypeptide may contain an Fc domain from an antibody and another binding domain that is a non-FcR binding domain. In some embodiments, the non-Fc binding region is not an antigen binding site of an antibody but specifically binds a cell-surface protein or a soluble protein. In some cases, a cell-surface protein that the non-Fc binding region recognizes is a receptor, such as, e.g., a receptor expressed on a cell surface.

Other polypeptides include those having Fc domain variants (e.g., capable of enhanced binding to a FcRn polypeptide at acidic pH while exhibiting reduced binding or no detectable binding to a FcRn at physiological or neutral pH) and a second binding domain that is a non-Fc receptor binding domain, wherein the second binding domain is capable of specifically binding a cell-surface molecule or a soluble protein. In some embodiments, the second binding domain is an antigen binding domain of an antibody ("Ig variable domain"). In some aspects, the polypeptide may be a full-length antibody. In some cases, the second binding domain is not an antibody antigen binding domain. In some embodiments, the second binding domain is capable of specifically binding a cell-surface molecule that is a protein or proteinaceous molecule. In some aspects, the second binding domain is capable of specifically binding a soluble protein.

Some aspects concern a nucleic acid that encodes any of the polypeptides discussed herein. The nucleic acid may be isolated and/or recombinant. It may be a nucleic acid segment that is isolated and/or recombinant. In some embodiments, the nucleic acid is DNA or RNA. In some embodiments, the nucleic acid is a DNA segment. In some embodiments, the nucleic acid is an expression vector that is capable of expressing any of the polypeptides having an Fc binding domain with one or more substitutions that specifically binds FcγRn. A nucleic acid may encode one or more polypeptides herein, which, depending on the presence or absence of certain mutations, as well as how the polypeptide is produced, may or may not be glycosylated.

In some embodiments, the nucleic acid encodes a polypeptide comprising or consisting of a variant or mutant Fc domain capable of pH-selectively binding FcRn as described herein. The nucleic acid may be placed (e.g., transfected or transformed) into a host cell that can express the polypeptide, such as an aglycosylated version of the polypeptide. The host cell may be a prokaryotic cell, such as a bacterial cell. Alternatively, the host cell may be a eukaryotic cell, such as a mammalian cell. In some embodiments, a host cell contains a first expression vector, though it may comprise a second expression vector as well. Because some antibodies are made of multiple polypeptides, a host cell that contains the expression vector(s) needed to express the polypeptides may be utilized in some embodiments. In some embodiments, the host cell expresses a first expression vector encoding a polypeptide comprising or consisting of an immunoglobulin heavy chain (e.g., containing a variant or mutant Fc domain that binds FcRn with enhanced affinity at acidic pH but is non-bound at neutral pH). In some embodiments, the host cell includes a second expression vector that encodes a polypeptide comprising or consisting of an immunoglobulin light chain. The host cell may comprise, e.g., one or two expression vectors to allow for the expression of an antibody comprising a heavy chain and a light chain.

In some aspects, a population of host cells is provided, wherein the population contains a plurality of host cells that express polypeptides having different Fc domains. It is contemplated that the amino acid sequence of any two different Fc domains may differ in identity by less than 20%, 15%, 10%, 5%, or less.

In some aspects, provided are methods of making the polypeptides described herein (e.g., polypeptides having an Fc region that binds FcRn with enhanced affinity at acidic pH but is non-bound at neutral pH) as well as methods of using these polypeptides. It is anticipated that methods described herein or known to one of ordinary skill may be to generate or use any of the polypeptides described herein.

In some embodiments, methods involve purifying the polypeptide from the supernatant. This may involve subjecting the polypeptides from the supernatant to filtration, HPLC, anion or cation exchange, high performance liquid chromatography (HPLC), affinity chromatography or a combination thereof. In some embodiments, methods involve affinity chromatography using staphylococcal Protein A, which binds the IgG Fc region. Other purification methods are well known to those of ordinary skill in the art.

In some embodiments, there is provided a pharmaceutical formulation comprising a polypeptide or nucleic acid of the present embodiments in a pharmaceutically acceptable carrier or a pharmaceutical preparation comprising an excipient.

In some embodiments, an immune response may be induced in a subject by a method comprising providing or administering (e.g., intravenously, etc.) to the subject an antibody, wherein the antibody comprises an Fc domain that binds to FcRn with enhanced affinity at acidic pH but is unbound at neutral pH or physiological pH, as described herein.

In a further embodiment, cancer, infection, autoimmune or inflammatory diseases may be treated by administering a therapeutic polypeptide comprising a variant or mutant Fc domain that binds to FcRn with enhanced affinity at acidic pH but is unbound at neutral pH or physiological pH, as described herein. It is envisioned that a polypeptide comprising a mutant or variant Fc domain as described herein may exhibit a similar complement-dependent cytotoxicity (CDC) compared to the CDC induced by a polypeptide comprising a wild-type human IgG Fc region. In still a further embodiment, the polypeptides according to the present invention may exhibit a similar ADCC or ADCP as compared to wild-type human IgG antibodies.

As used herein, "pH-selectively binding FcRn" or "binds to FcRn in a pH-selective manner" refers to a property of a polypeptide such as a Fc domain (e.g., a mutant or variant IgG Fc domain) to have the ability to bind FcRn at acidic pH (e.g., pH 5.8), and preferably the polypeptide or Fc domain has the ability to display increased binding of FcRn at acidic pH as compared to a wild-type Fc domain (e.g., a wild-type Fc IgG domain). In some embodiments, a Fc domain or polypeptide that pH-selectively binds FcRn also displays either reduced binding of FcRn at physiological pH as compared to wild-type (e.g., a wild-type IgG Fc domain) or no detectable binding of FcRn at physiological pH.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein, the term "affinity" refers to the equilibrium constant for the reversible binding of two agents and is expressed as $K_D$. Affinity of a binding domain to its target can be, for example, from about 100 nanomolar (nM) to about 0.1 nM, from about 100 nM to about 1 picomolar (pM), or from about 100 nM to about 1 femtomolar (fM); alternatively, it can be between 100 nM and 1 nM or between 0.1 nM and 10 nM. Moreover, it is contemplated that agents specifically bind when there is an affinity between the two agents that is in the affinity ranges discussed above.

As used herein the terms "encode" or "encoding," with reference to a nucleic acid, are used to make the invention readily understandable by the skilled artisan; however, these terms may be used interchangeably with "comprise" or "comprising," respectively.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device used to measure the variable, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-B. Brief schema of two plasmid system for bacterial periplasmic display of Trastuzumab light chain (FIG. 1A) and Trastuzumab heavy chain (FIG. 1B).

FIG. 3A, IgG-displaying spheroplasts were labeled with single chain FcRn (scFcRn)-APC at pH 5.8 and then labeled with dimeric FcRn-FITC at pH7.4. FIG. 3B, Fc library were screened with FcRn for five rounds and the resulting FcRn-binding activities were presented.

FIGS. 16A-C. ELISA assays of IgG2-DHS, IgG3-DHS, and IgG4-DHS. FcγR-binding activities of IgG variants compared with their wild type IgG. 400, 80, 16, 3.2 nM of FcγRs were assayed with IgG variants.

FIG. 17. Pharmacokinetics of antibodies in human FcRn transgenic mice.

DESCRIPTION OF ILLUSTRATIVE EMBODIMENTS

Figure 2:
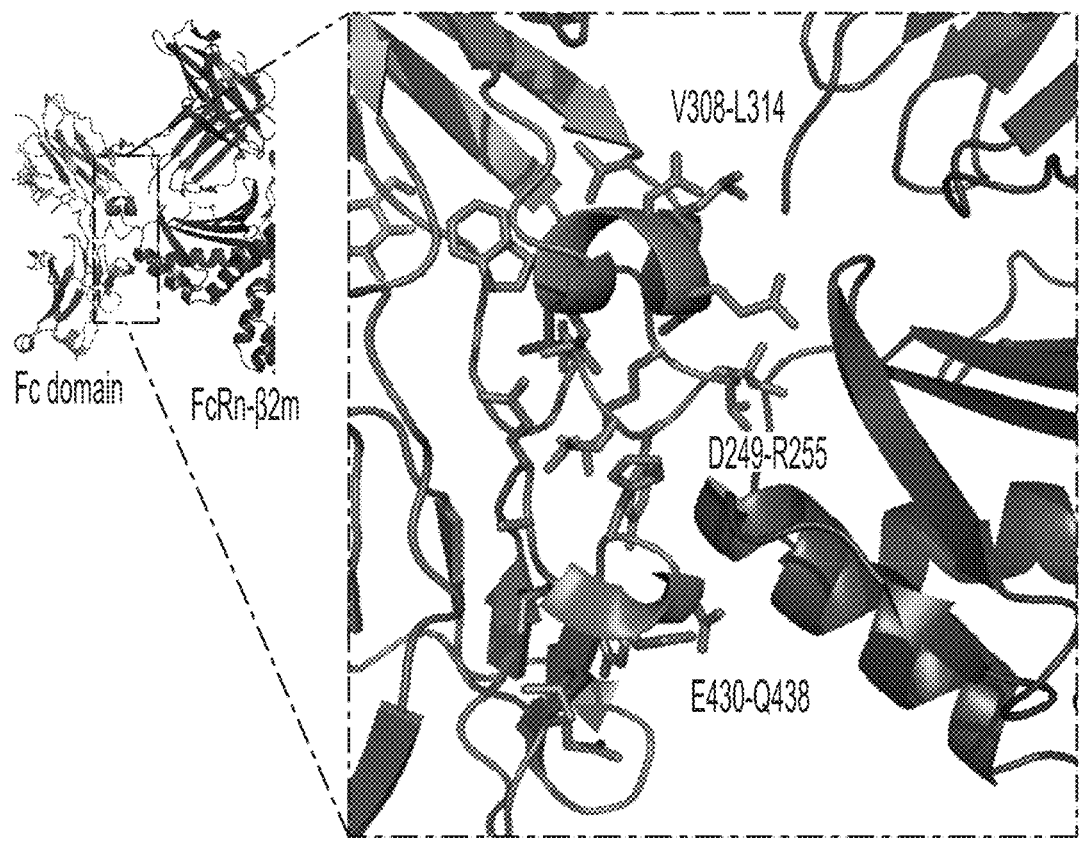
FIG. 2. Complex structure of Fc domain of IgG1 with FcRn-β2m. The neighboring residues of Fc domain near FcRn (<7 Å) has been highlighted on the basis of FcRn-Fc complex structure (PDB ID: 4N0U) (Oganesyan V. et al., 2014). The side chains of neighboring residues in Fc Domain to FcRn are shown in the highlighted structure. The neighboring residues in Fc domain to FcRn are randomized with primers, which contains degenerated codons. IgG1-Fc domain (left), FcRn-β2m (right).

Provided herein are methods and compositions involving polypeptides having engineered antibody Fc domains displaying improved pH-dependent binding to FcRn. In some preferred aspects, the mutant Fc domains may exhibit improved half-life or reduced degradation after administration to a mammalian subject in vivo. As shown in the below examples, these improvements in FcRn binding have been observed in mutant Fc domains that may exist in glycosylated or aglycosylated antibodies for a variety of antibody types (e.g., IgG1, IgG2, IgG3, IgG4). Since, in some instances, aglycosylated antibodies have been associated with some risks (e.g., immunogenicity, poor in vivo stability, or unfavorable pharmacokinetics), in some embodiments it may be desirable to include the mutant Fc domain in a glycosylated antibody. Nonetheless, aglycosylated antibodies may be used for a variety of useful or therapeutic approaches, and thus inclusion of the mutant Fc domain in an aglycosylated antibody may also result in benefits, e.g., improved in vivo half-life of the aglycosylated antibodies. In some embodiments, the mutant Fc domains bind to FcRn at an acidic pH and do not bind to FcRn at neutral pH, and have a FcγR-binding capacity equivalent to wild type Fc domains. For example, the polypeptide may include a mutant or variant Fc domain that binds to FcRn in a pH-selective manner, while having a binding capacity equivalent to wild-type for binding FcγRI, FcγRII, and/or FcγRIII.

I. ANTIBODY FC DOMAINS

It is well known that the neonatal Fc receptor (FcRn) plays a central role in the regulation of serum IgG levels in mammals (Ghetie, V., and Ward, E. S. 2000). The Fc-binding FcRn is a heterodimer which comprises β2-microglobulin (β2m) and a membrane-anchored chain that is related to the chain of major histocompatibility complex class I (MHC class I) molecules. IgG-FcRn interactions exhibit significant pH dependence varying from strong at slightly acidic pH to weak under neutral and basic pH (Rodewald, R. 1976 and Raghavan, M. et al., 1995). The generally accepted FcRn-mediated IgG recycling mechanism are the following procedure; 1) Internalization of IgG by pinocytosis, 2) Acidification of endosome (early endosome: ~pH 6.0, late endosome: ~pH 4.5) and interaction of IgG and FcRn, 3) Exocytosis and dissociation of IgG from FcRn, 4) Re-internalization of non-released IgG by endocytosis, 5) Lysosome fusion and degradation of IgGs. As a result, the recycled IgG exhibits a significantly prolonged serum half-life compared to other serum proteins (Ghetie, V. et al., 1996 and Borvak, J. et al., 1998). IgG that maintains significant binding to FcRn at neutral pH has significantly reduced serum persistence (Dall'Acqua, W. F. et al., 2003).

Therapeutic antibodies with longer serum half-lives are beneficial when the efficacy increases due to continuous serum concentrations, reduced frequency of administration and/or lower costs. Although it seems sensible to manipulate Fc-FcRn interactions to prolong plasma half-life, many of the potential biological consequences associated with the IgG-transporting role of FcRn are well known. In particular, this function includes the transcytosis of IgG through human placenta (Firan et al., 2001) and intestines (Israel et al., 1997 and Dickinson et al., 1999) as well as the reabsorption of IgG (Haymann et al., 2000) in human kidneys.

Based on the FcRn-mediated homeostasis, the Fc Engineering to enhance the serum half-life is usually focused on enhancing the affinity of Fc to FcRn at acidic pH and maintaining original pH dependent binding character. Many engineered Fc variants for FcRn, such as Fc domains containing the M428L/N434S (LS) or M252Y/S254T/T256E (YTE)amino acid substitutions, have been developed and LS and YTE showed 10 to 20-fold enhanced affinity at endosomal pH comparing with wild-type IgG1 (WT) and no significant affinity at pH 7.4, resulting in the enhanced serum half-life in transgenic human FcRn (hFcRn) mice, primates and/or human (Acqua et al., 2002; Zalevsky et al., 2010; Ko et al., 2014; Deng et al., 2010; Hinton et al., 2004 and 2006; Yeung et al., 2009 and 2010; Borrok et al., 2015; Robbie et al., 2013). Notably antibodies with the "YTE" variant are being evaluated in several clinical trials. Antibodies with the "YTE" mutations have been shown to have serum half-lives as long as 3 months, a property that can substantially reduce dosing, enable better patient compliance and better therapeutic efficacy. However, higher FcRn affinity at acidic pH is not clearly correlated to the enhancement of serum half-life and some engineered variants with similarly or better improved FcRn binding characteristics at acidic pH failed to exhibit expected increases in in vivo half-life (Borrok et al., 2015, Datta-Mannan et al., 2007 and 2012, and Zheng et al., 2011). On the other hand, the affinity of antibodies at neutral pH showed better correlation to PK than it at acidic pH (Cooper et al., 2014 and Wang et al., 2011). Based on the FcRn-recycling mechanism, the affinity of IgG at pH 7.4 is critical factor for antibody recycling. Accurate and precise measurement of affinity of antibodies at neutral pH is very critical. Recently, attempts have been reported to measure the affinity of antibodies for FcRn at pH 7.4 by SPR, using a very high level of immobilized FcRn. The YTE variant showed about 57-fold higher affinity than wild type IgG1 at pH 7.4 by kinetic analysis with high-density FcRn, which was not shown in the assay with low-density FcRn (Walters et al., 2016).

In certain embodiments, there are compositions comprising a proteinaceous molecule that has been modified relative to a native or wild-type protein. In some embodiments that proteinaceous compound has been deleted of amino acid residues; in other embodiments, amino acid residues of the proteinaceous compound have been replaced; while in still further embodiments both deletions and replacements of amino acid residues in the proteinaceous compound have been made. Furthermore, a proteinaceous compound may include an amino acid molecule comprising more than one polypeptide entity. As used herein, a "proteinaceous molecule," "proteinaceous composition," "proteinaceous compound," "proteinaceous chain," or "proteinaceous material" generally refers, but is not limited to, a protein of greater than about 200 amino acids or the full-length endogenous sequence translated from a gene; a polypeptide of 100 amino acids or greater; and/or a peptide of 3 to 100 amino acids. All the "proteinaceous" terms described above may be used interchangeably herein; however, it is specifically contemplated that embodiments may be limited to a particular type of proteinaceous compound, such as a polypeptide. Furthermore, these terms may be applied to fusion proteins or protein conjugates as well. A protein may include more than one polypeptide. An IgG antibody, for example, has two heavy chain polypeptides and two light chain polypeptides, which are joined to each other through disulfide bonds.

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide," and "peptide" are used interchangeably herein.

As used herein, an "amino acid residue" refers to any amino acid, amino acid derivative, or amino acid mimic as would be known to one of ordinary skill in the art. In certain embodiments, the residues of the proteinaceous molecule are sequential, without any non-amino acid residue interrupting the sequence of amino acid residues. In other embodiments, the sequence may comprise one or more non-amino acid moieties. In particular embodiments, the sequence of residues of the proteinaceous molecule may be interrupted by one or more non-amino acid moieties.

As used herein a "distinct Fc domain" may be defined as a domain that differs from another Fc by as little as one amino acid. Methods for making a library of distinct antibody Fc domains or nucleic acids that encode antibodies are well known in the art. For example, in some cases Fc domains may be amplified by error prone PCR. Furthermore, in certain cases a plurality of antibody Fc domains may comprise a stretch (1, 2, 3, 4, 5, 6, 7, 8, 9, 10 or more) of amino acids that have been randomized. In certain cases, specific mutations may be engineered into Fc domains. For example, in some aspects, residues that are normally glycosylated in an antibody Fc domain may be mutated. Furthermore, in certain aspects, residues that are normally glycosylated (or adjacent residues) may be used as a site for an insertion of 1, 2, 3, 4, 5, 6, 7, 8, 9, 10 or more amino acids.

A polypeptide may comprise a mutant or variant antibody Fc domain capable of binding an FcR polypeptide. In some aspects, the Fc domain may be further defined as having a specific affinity for an FcR polypeptide under physiological conditions. For instance an Fc domain may have an equilibrium dissociation constant between about $10^{-6}$ M to about $10^{-9}$ M under physiological conditions. Furthermore in some aspects an aglycosylated Fc domain may be defined as comprising one or more amino acid substitutions or insertions relative to a wild-type sequence, such as a human wild-type sequence. The Fc domain may be glycosylated or aglycosylated.

Means of preparing such a polypeptide include those discussed in PCT Publn. WO 2008/137475, which is hereby incorporated by reference. One can alternatively prepare such polypeptides directly by genetic engineering techniques such as, for example, by introducing selected amino acid substitutions or insertions into a known Fc background, wherein the insertion or substitution provides an improved FcR binding capability to aglycosylated Fc regions, as discussed above. In some embodiments, an Fc domain is engineered to bind one or more specific Fc receptors. Additionally or alternatively, an Fc domain may be engineered so that it does not specifically bind one or more specific Fc receptors.

In some embodiments, an Fc domain comprises a specific binding affinity for an FcR such as human FcγRIA, FcγRIIA, FcγRIIB, FcγRIIc, FcγRIIIA, FcγRIIIb, FcαRI, or for C1q. In some embodiments, the antibody is a glycosylated antibody that displays FcR binding that is similar to, essentially the same as, or the same as FcR binding for the wild type antibody, e.g., as compared to the corresponding IgG2, IgG3, or IgG4 antibody. In some embodiments, the antibody is glycosylated. In some embodiments, the antibody is an aglycosylated antibody. The binding affinity of an antibody Fc or other binding protein can, for example, be determined by the Scatchard analysis of Munson and Pollard (1980). Alternatively, binding affinity can be determined by surface plasmon resonance or any other well-known method for determining the kinetics and equilibrium constants for protein:protein interactions. Isolated IgG variants are provided below in Table 1. In various embodiments, the mutations may be introduced into an IgG1 Fc domain (e.g., SEQ ID NOs: 5-8), or corresponding mutations may be made in an IgG2 Fc domain (e.g., SEQ ID NO:9), an IgG3 Fc domain (e.g., SEQ ID NO:10), or an IgG4 Fc domain (e.g., SEQ ID NO:11), as desired.

TABLE 1

Isolated IgG variants (Sequence numbering is based on Kabat and mutations are specified below)

EDHS (V264E, L309D, Q311H, N434S; SEQ ID NO: 5),
EDHY (V264E, L309D, Q311H, N434Y; SEQ ID NO: 6),
DHS (L309D, Q311H, N434S; SEQ ID NO: 7),
DHY (L309D, Q311H, N434Y; SEQ ID NO: 8),
IgG2-DHS (V309D, Q311H, N434S; SEQ ID NO: 9),
IgG3-DHS (L309D, Q311H, N434S; SEQ ID NO: 10),
IgG4-DHS (L309D, Q311H, N434S; SEQ ID NO: 11)

By "position" as used herein is meant a location in the sequence of a protein. Positions may be numbered sequentially, or according to an established format, for example the EU index for antibody numbering.

For all positions discussed in the present invention, numbering is according to the EU index. The "EU index" or "EU index as in Kabat" or "EU numbering scheme" refers to the numbering of the EU antibody (Edelman et al., 1969; Kabat et al., 1991; both incorporated herein by reference in their entirety).

In certain embodiments the size of the at least one Fc polypeptide proteinaceous molecule may comprise, but is not limited to, about or at least 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 350, 400, 450, 500, 550, 600, 650, 700, 750, 800, 850, 900, 950, 1000 or greater amino molecule residues, and any range derivable therein. Compounds may include the above-mentioned number of contiguous amino acids from SEQ ID NO:1-4 (human IgG1-4 Fc polypeptide) or from SEQ ID NOs: 5-11, and these may be further qualified as having a percent sequence identity or homology to a wild-type human IgG Fc domain (e.g., percent sequence identity to any one of SEQ ID NOs:1-4).

A. Modified Proteins and Polypeptides

Some embodiments concern modified proteins and polypeptides, particularly a modified protein or polypeptide that exhibits at least one functional activity that is comparable to the unmodified version, yet the modified protein or polypeptide possesses an additional advantage over the unmodified version, such as suppressing B-cell activation, being easier or cheaper to produce, eliciting fewer side effects, and/or having better or longer efficacy or bioavailability. Thus, when the present application refers to the function or activity of "modified protein" or a "modified polypeptide" one of ordinary skill in the art would understand that this includes, for example, a protein or polypeptide that 1) performs at least one of the same activities or has at least one of the same specificities as the unmodified protein or polypeptide, but that may have a different level of another activity or specificity; and 2) possesses an additional advantage over the unmodified protein or polypeptide. Determination of activity may be achieved using assays familiar to those of skill in the art, particularly with respect to the protein's activity, and may include for comparison purposes, for example, the use of native and/or recombinant versions of either the modified or unmodified protein or polypeptide. It is specifically contemplated that embodiments concerning a "modified protein" may be implemented with respect to a "modified polypeptide," and vice versa. In addition to the modified proteins and polypeptides discussed herein, embodiments may involve domains, polypeptides, and proteins described in PCT Publn. WO 2008/137475, which is hereby specifically incorporated by reference.

Modified proteins may possess deletions and/or substitutions of amino acids; thus, a protein with a deletion, a protein with a substitution, and a protein with a deletion and a substitution are modified proteins. In some embodiments these modified proteins may further include insertions or added amino acids, such as with fusion proteins or proteins with linkers, for example. This may include the insertion of a targeting peptide or polypeptide or simply a single residue. Terminal additions, called fusion proteins, are discussed below.

A "modified deleted protein" lacks one or more residues of the native protein, but possesses the specificity and/or activity of the native protein. A "modified deleted protein" may also have reduced immunogenicity or antigenicity. An example of a modified deleted protein is one that has an amino acid residue deleted from at least one antigenic region (i.e., a region of the protein determined to be antigenic in a particular organism, such as the type of organism that may be administered the modified protein).

Substitutional or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a native polypeptide are included, provided the biological activity of the protein is maintained. A modified protein may be biologically functionally equivalent to its native counterpart.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure with or without appreciable loss of interactive binding capacity with structures such as, for example, binding sites to substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated that various changes may be made in the DNA sequences of genes without appreciable loss of their biological utility or activity, as discussed below. A proteinaceous molecule has "homology" or is considered "homologous" to a second proteinaceous molecule if one of the following "homology criteria" is met: 1) at least 30% of the proteinaceous molecule has sequence identity at the same positions with the second proteinaceous molecule; 2) there is some sequence identity at the same positions with the second proteinaceous molecule and at the non-identical residues, at least 30% of them are conservative differences, as described herein, with respect to the second proteinaceous molecule; or 3) at least 30% of the proteinaceous molecule has sequence identity with the second proteinaceous molecule, but with possible gaps of non-identical residues between identical residues. As used herein, the term "homologous" may equally apply to a region of a proteinaceous molecule, instead of the entire molecule. If the term "homology" or "homologous" is qualified by a number, for example, "50% homology" or "50% homologous," then the homology criteria, with respect to 1), 2), and 3), is adjusted from "at least 30%" to "at least 50%." Thus it is contemplated that there may homology of at least 30%, 35%, 40%, 45%, 50%, 55%, 60%, 65%, 70%, 75%, 80%, 85%, 90%, 95%, or more between two proteinaceous molecules or portions of proteinaceous molecules.

Alternatively, a modified polypeptide may be characterized as having a certain percentage of identity to an unmodified polypeptide or to any polypeptide sequence disclosed herein, including any of the mutant or variant Fc domains or sequences (e.g., SEQ ID NOs:5-11) described herein. The percentage identity may be at most or at least 50%, 55%, 60%, 65%, 70%, 75%, 80%, 85%, 90%, 95%, 96%, 97%, 98%, 99% or 100% (or any range derivable therein) between two proteinaceous molecules or portions of proteinaceous molecules. It is contemplated that percentage of identity discussed above may relate to a particular region of a polypeptide compared to an unmodified region of a polypeptide. For instance, a polypeptide may contain a modified or mutant Fc domain that can be characterized based on the identity of the amino acid sequence of the modified or mutant Fc domain to an unmodified or mutant Fc domain from the same species. A modified or mutant human Fc domain characterized, for example, as having 90% identity to an unmodified Fc domain means that 90% of the amino acids in that domain are identical to the amino acids in an unmodified human Fc domain (e.g., SEQ ID NOs:1-4).

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine, and isoleucine.

B. Modified Antibodies and Proteinaceous Compounds with Heterologous Regions

Once an Fc domain has been isolated, it may be desired to link the molecule to at least one agent to form a conjugate to enhance the utility of that molecule. For example, in order to increase the efficacy of Fc domains or antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles, or ligands, such as biotin. Another such example is the formation of a conjugate comprising an antibody linked to a cytotoxic or anti-cellular agent, and may be termed "immunotoxins." Techniques for labeling such a molecule are known to those of skill in the art and have been described herein above.

Labeled proteins, such as Fc domains that have been prepared in accordance with the invention may also then be employed, for example, in immunodetection methods for binding, purifying, removing, quantifying, and/or otherwise generally detecting biological components, such as protein(s), polypeptide(s), or peptide(s). Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev, 1999; Gulbis and Galand,1993; and De Jager et al., 1993, each incorporated herein by reference.

The Fc domain molecules, including antibodies, may be used, for example, in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Abbondanzo et al., 1990).

Some embodiments concern an Fc polypeptide proteinaceous compound that may include amino acid sequences from more than one naturally occurring or native polypeptides or proteins. Embodiments discussed above are contemplated to apply to this section, and vice versa. For instance, a modified antibody is one that contains a modified Fc domain with an antigen binding domain. Moreover, the antibody may have two different antigen binding regions, such as a different region on each of the two heavy chains. Alternatively or additionally, in some embodiments, there are polypeptides comprising multiple heterologous peptides and/or polypeptides ("heterologous" meaning they are not derived from the same polypeptide). A proteinaceous compound or molecule, for example, could include a modified Fc domain with a protein binding region that is not from an antibody. In some embodiments, there are polypeptides comprising a modified Fc domain with a protein binding region that binds a cell-surface receptor. These proteinaceous molecules comprising multiple functional domains may be two or more domains chemically conjugated to one another or it may be a fusion protein of two or more polypeptides encoded by the same nucleic acid molecule. It is contemplated that proteins or polypeptides may include all or part of two or more heterologous polypeptides.

Thus, a multipolypeptide proteinaceous compound may be comprised of all or part of a first polypeptide and all or part of a second polypeptide, a third polypeptide, a fourth polypeptide, a fifth polypeptide, a sixth polypeptide, a seventh polypeptide, an eight polypeptide, a ninth polypeptide, a tenth polypeptide, or more polypeptides.

Amino acids, such as selectively-cleavable linkers, synthetic linkers, or other amino acid sequences, may be used to separate proteinaceous moieties.

Polypeptides or proteins (including antibodies) having an antigen binding domain or region of an antibody and a mutant or variant Fc domain can be used against any antigen or epitope, including but not limited to proteins, subunits, domains, motifs, and/or epitopes belonging to the following list of targets: 17-IA, 4-1BB, 4Dc, 6-keto-PGF1a, 8-iso-PGF2a, 8-oxo-dG, A2 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAMS, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Ax1, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/ZIP, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCLS, CCL6, CCL7, CCL8, CCL9/10, CCR, CCR1, CCR10, CCR10, CCR2, CCR3, CCR4, CCRS, CCR6, CCR7, CCR8, CCR9, CD1, CD2, CD3, CD3E, CD4, CDS, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD3OL, CD32, CD33 (p67 proteins), CD34, CD38, CD40, CD4OL, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAMS, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCLS, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCRS, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, EGAD, EDA, EDA-Al, EDA-A2, EDAR, EGF, EGFR (ErbB-1), EMA, EMMPRIN, ENA, endothelin receptor, Enkephalinase, eNOS, Eot, eotaxinl, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MM), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Mucl), MUC18, Muellerian-inhibitin substance, Mug, MuSK, NAIP, NAP, NCAD, N-Cadherin, NCA 90, NCAM, NCAM, Neprilysin, Neurotrophin-3,-4, or -6, Neurturin, Neuronal growth factor (NGF), NGFR, NGF-beta, nNOS, NO, NOS, Npn, NRG-3, NT, NTN, OB, OGG1, OPG, OPN, OSM, OX4OL, OX4OR, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGD2, PIN, PLA2, placental alkaline phosphatase (PLAP), PIGF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, 5100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p'75-80), TNFRSF26 (TNFRH3), TNFRSF3 (LTbR TNF RIII, TNFC R), TNFRSF4 (OX40 ACT35, TXGP1 R), TNFRSFS (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (DcTRAIL R1 TNFRH1), TNFRSF25 (DR3 Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3 Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (flt-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNTSA, WNTSB, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors. In some embodiments, a polypeptide or protein has an antigen binding domain specific for one or more cell surface tumor antigens or B-cell antigen. Methods and compositions may be employed to target a tumor cell or B-cell.

Any antibody of sufficient selectivity, specificity, or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4, and the HIV-1 envelope (Silverman, 1995; Cleary et al., 1994; Lenert et al., 1990; Berberian et al., 1993; Kreier et al., 1981). In addition, the variable domain is involved in antibody self-binding (Kang et al., 1988), and contains epitopes (idiotopes) recognized by anti-antibodies (Bhattacharya et al., 1989).

Fc domains can bind to an FcR; however, it is contemplated that the regulation of immune response can be directed not only through an antigen binding domain on the polypeptide containing the Fc domain, but through some other protein binding domain. Consequently, some embodiments may concern an Fc domain and a heterologous non-antigen binding domain. In certain embodiments, the non-antigen binding domain binds to the cell surface. Therefore, these agents require either chemical conjugation to, or fusion with, agents/proteins that are capable of binding to specific target cells. Embodiments may further include adjoining all or part of a mutant or variant Fc domain to all or part of any of the proteins listed in Table 2. It is contemplated that embodiments include, but are not limited to, the examples provided in Table 2 and the description herein.

A ligand for a receptor may be employed to target a cell expressing on its surface the receptor for the ligand. Ligands also include, for instance, CD95 ligand, TRAIL, TNF (such as TNF-α or TNF-β), growth factors, including those discussed above, such as VEGF, and cytokines, such as interferons or interleukins, and variants thereof. Embodiments with multiple domains are also contemplated, such as a VEGF Trap fusion protein that includes the second extracellular domain of the VEGF receptor 1 (Flt-1) with the third domain of the VEGF receptor 2 (KDR/FlK-1) and an IgG Fc region.

TABLE 2

Agents/proteins capable of binding specific target cells

| Protein Genus | Subgenus | Species | Subspecies |
|---|---|---|---|
| Antibodies | Polyclonal Monoclonal | Non-recombinant Recombinant | |
| | | | Chimeric Single chain Diabody |
| | | Multimeric | |
| Ligands for cell-surface receptors | | | IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19 |
| | Cytokines/ growth factors | | |
| | | Cytokines/growth factors for receptor tyrosine kinases | |
| | | | GM-CSF, G-CSF, M-CSF, EGF, VEGF, FGF, PDGF, HGF, GDNF, Trk, AXL, LTK, TIE, ROR, DDR, KLG, RYK, MuSK ligands |
| Non-Ab binding protein for cell-surface molecule | Binders of cell surface proteins | | |
| | | Cluster of differentiation (CD) molecules | |

C. Antibody Fc Libraries

Examples of techniques that could be employed in conjunction with embodiments for creation of diverse antibody Fc domains and/or antibodies comprising such domains may employ techniques similar to those for expression of immunoglobulin heavy chain libraries described in U.S. Pat. No. 5,824,520. Previously employed Fc libraries are discussed in PCT Publn. WO 2008/137475, which is specifically incorporated herein by reference.

II. ANTIBODY-BINDING POLYPEPTIDES

A variety of antibody-binding domains (e.g., FcR polypeptides) are known in the art and may be used in the methods and compositions of the invention. For example, in some aspects, an FcR may have specificity for a particular type or subtype of Ig, such as IgA, IgM, IgE, or IgG (e.g., IgG1, IgG2a, IgG2b, IgG3, or IgG4). Thus, in some embodiments the antibody-binding domain may be defined as an IgG binding domain. The FcR polypeptide may comprise a eukaryotic, prokaryotic, or synthetic FcR domain. For instance, an antibody Fc-binding domain may be defined as a mammalian, bacterial, or synthetic binding domain. Some Fc-binding domains for use in the invention include but are not limited to a binding domain from one of the polypeptides of Table 3. For example, an Fc-binding polypeptide may be encoded by an FCGR2A, FCGR2B, FCGR2C, FCGR3A, FCGR3B, FCGR1A, Fcgr1, FCGR2, FCGR2, Fcgr2, Fcgr2, FCGR3, FCGR3, Fcgr3, FCGR3, Fcgr3, FCGRT, mrp4, spa, or spg gene. Preferably, an FcR polypeptide for use according to the invention may be an Fc binding region from human FcγRIA, FcγRIIA, FcγRIIB, FcγRIIc, FcγRIIIA, FcγRIIIb, FcαRI, or C1q. A variety of Fc receptors to which Fc domains bind are well known in the art and some examples of receptors are listed below in Table 3.

TABLE 3

Selected FcR Polypeptides

| Protein name | Gene name | Description | Organisms | Length (aa) | Reference |
|---|---|---|---|---|---|
| Fc-gamma RII-a (CD32) | FCGR2A | Low affinity immunoglobulin gamma Fc region receptor II-a precursor | Homo sapiens (Human) | 317 | (Stuart et al., 1987) |
| Fc-gamma RIIa | FCGR2A | Low affinity immunoglobulin gamma Fc region receptor II-a precursor | Pan troglodytes (Chimpanzee) | 316 | |
| Fc-gamma RII-b | FCGR2B | Low affinity immunoglobulin gamma Fc region receptor II-b precursor | Homo sapiens (Human) | 310 | (Stuart et al., 1989) |
| Fc-gamma RII-c | FCGR2C | Low affinity immunoglobulin gamma Fc region receptor II-c precursor | Homo sapiens (Human) | 323 | (Stuart et al., 1989) |
| Fc-gamma RIIIa | FCGR3A | Low affinity immunoglobulin gamma Fc region receptor III-A precursor | Homo sapiens (Human) | 254 | (Ravetch and Perussia, 1989) |
| Fc-gamma RIIIb | FCGR3B | Low affinity immunoglobulin gamma Fc region receptor III-B precursor | Homo sapiens (Human) | 233 | (Ravetch and Perussia, 1989) |
| Fc-gamma RI (CD64) | FCGR1A | High affinity immunoglobulin gamma Fc receptor I precursor | Homo sapiens (Human) | 374 | (Allen and Seed, 1988) |
| Fc-gamma RI | Fcgr1 | High affinity immunoglobulin gamma Fc receptor I precursor | Mus musculus (Mouse) | 404 | (Sears et al., 1990) |
| Fc-gamma RII | FCGR2 | Low affinity immunoglobulin gamma Fc region receptor II precursor | Bos taurus (Bovine) | 296 | (Zhang et al., 1994) |
| Fc-gamma RII | FCGR2 | Low affinity immunoglobulin gamma Fc region receptor II precursor | Cavia porcellus (Guinea pig) | 341 | (Tominaga et al., 1990) |
| Fc-gamma RII | Fcgr2 | Low affinity immunoglobulin gamma Fc region receptor II precursor | Mus musculus (Mouse) | 330 | (Ravetch et al., 1986) |
| Fc-gamma RII | Fcgr2 | Low affinity immunoglobulin gamma Fc region receptor II precursor | Rattus norvegicus (Rat) | 285 | (Bocek and Pecht, 1993) |
| Fc-gamma RIII | FCGR3 | Low affinity immunoglobulin gamma Fc region receptor III precursor | Bos taurus (Bovine) | 250 | (Collins et al., 1997) |
| Fc-gamma RIII | FCGR3 | Low affinity immunoglobulin gamma Fc region receptor III precursor | Macaca fascicularis (Crab eating macaque) (Cynomolgus monkey) | 254 | |
| Fc-gamma RIII | Fcgr3 | Low affinity immunoglobulin gamma Fc region receptor III precursor | Mus musculus (Mouse) | 261 | (Ravetch et al., 1986) |
| Fc-gamma RIII | FCGR3 | Low affinity immunoglobulin gamma Fc region receptor III precursor | Sus scrofa (Pig) | 257 | (Halloran et al., 1994) |
| Fc-gamma RIII | Fcgr3 | Low affinity immunoglobulin gamma Fc region receptor III precursor | Rattus norvegicus (Rat) | 267 | (Zeger et al., 1990) |
| FcRn | FCGRT | IgG receptor transporter FcRn large subunit p51 precursor | Homo sapiens (Human) | 365 | |

TABLE 3-continued

Selected FcR Polypeptides

| Protein name | Gene name | Description | Organisms | Length (aa) | Reference |
|---|---|---|---|---|---|
| FcRn | FCGRT | IgG receptor transporter FcRn large subunit p51 precursor | *Macaca fascicularis* (Crab eating macaque) (Cynomolgus monkey) | 365 | |
| FcRn | Fcgrt | IgG receptor transporter FcRn large subunit p51 precursor | *Mus musculus* (Mouse) | 365 | (Ahouse et al., 1993) |
| FcRn | Fcgrt | IgG receptor transporter FcRn large subunit p51 precursor | *Rattus norvegicus* (Rat) | 366 | (Simister and Mostov, 1989) |
| MRP protein | mrp4 | Fibrinogen- and Ig-binding protein precursor | *Streptococcus pyogenes* | 388 | (Stenberg et al., 1992) |
| Protein B | | cAMP factor | *Streptococcus agalactiae* | 226 | (Ruhlmann et al., 1988) |
| protein A | spa | Immunoglobulin G-binding protein A precursor | *Staphylococcus aureus* (strain NCTC 8325) | 516 | (Uhlen et al., 1984) |
| protein A | spa | Immunoglobulin G-binding protein A precursor | *Staphylococcus aureus* | 508 | (Shuttleworth et al., 1987) |
| protein A | spa | Immunoglobulin G-binding protein A precursor | *Staphylococcus aureus* (strain Mu50/ATCC 700699) | 450 | (Kuroda et al., 2001) |
| protein A | spa | Immunoglobulin G-binding protein A precursor | *Staphylococcus aureus* (strain N315) | 450 | (Kuroda et al., 2001) |
| protein G | spg | Immunoglobulin G-binding protein G precursor | *Streptococcus* sp. group G | 448 | (Fahnestock et al., 1986) |
| protein G | spg | Immunoglobulin G-binding protein G precursor | *Streptococcus* sp. group G | 593 | (Olsson et al., 1987) |
| protein H | | Immunoglobulin G-binding protein H precursor | *Streptococcus pyogenes* serotype M1 | 376 | (Gomi et al., 1990) |
| Protein sbi | sbi | Immunoglobulin G-binding protein sbi precursor | *Staphylococcus aureus* (strain NCTC 8325-4) | 436 | (Zhang et al., 1998) |
| Allergen Asp fl 1 | | Allergen Asp fl 1 causes an allergic reaction in human. Binds to IgE and IgG | *Aspergillus flavus* | 32 | |
| Allergen Asp fl 2 | | Allergen Asp fl 2 causes an allergic reaction in human. Binds to IgE and IgG | *Aspergillus flavus* | 20 | |
| Allergen Asp fl 3 | | Allergen Asp fl 3 causes an allergic reaction in human. Binds to IgE and IgG | *Aspergillus flavus* | 32 | |
| Fc-epsilon RI | | IgE receptor displayed on Mast cells, Eosinophils and Basophils | *Homo sapiens* (Human) | | |
| Fc-alpha RI (CD86) | | IgA (IgA1, IgA2) receptor displayed on Macrophages | *Homo sapiens* (Human) | | |
| C1q | C1QA NP_057075.1, C1QB NP_000482.3, C1QC NP_758957.1 | C1q is multimeric complex that binds to antibody Fc composed of 6 A chains, 6 B chains and 6 C chains | *Homo sapiens* (Human) | | |

III. METHODS FOR SCREENING ANTIBODY FC DOMAINS

In certain aspects there are methods for identifying antibody Fc domains with a specific affinity for a target ligand (e.g., an antibody-binding polypeptide, such as an Fc receptor). Such methods are described herein, as well as in PCT Publn.WO 2008/137475, which is hereby specifically incorporated by reference in its entirety. For example, methods may be used to identify additional mutations that may be further included in a mutant or variant Fc domain or antibody, in addition to Fc domain substitution mutations disclosed herein (e.g., in addition to L309D, Q311H, and N434S/Y in a human IgG Fc domain). A variety of methods for identifying additional mutations are known in the art and may be used herein (e.g., U.S. Pat. Nos. 7,094,571, 7,419,783, 7,611,866 and U.S. Patent Publn. No. 2003/0219870; Harvey et al.,2004; Harvey et al., 2006).

IV. NUCLEIC ACID-BASED EXPRESSION SYSTEMS

Nucleic acid-based expression systems may find use, in certain embodiments of the invention, for the expression of recombinant proteins. For example, one embodiment of the invention involves transformation of Gram-negative bacteria with the coding sequences for an antibody Fc domain, or preferably a plurality of distinct Fc domains.

A. Methods of Nucleic Acid Delivery

Certain aspects of the invention may comprise delivery of nucleic acids to target cells (e.g., Gram-negative bacteria). For example, bacterial host cells may be transformed with nucleic acids encoding candidate Fc domains potentially capable binding an FcR. In particular embodiments of the invention, it may be desired to target the expression to the periplasm of the bacteria. Transformation of eukaryotic host cells may similarly find use in the expression of various candidate molecules identified as capable of binding a target ligand.

Suitable methods for nucleic acid delivery for transformation of a cell are well known in the art. In some aspects, a mutant or variant Fc domain is encoded in a nucleic acid expression vector, which may be used to transform a cell such as a bacterial or eukaryotic cell.

The term "expression vector" refers to a vector containing a nucleic acid sequence coding for at least part of a gene product capable of being transcribed. Expression vectors can contain a variety of "control sequences," which refer to nucleic acid sequences necessary for the transcription and possibly translation of an operably linked coding sequence in a particular host organism. Additionally, an expression vector may include a promoter, enhancer, initiation signal, multiple cloning site (MCS), termination signal, one or more origins of replication sites (often termed "ori"), a selectable and/or a screenable marker (e.g., to confer resistance to neomycin, puromycin, hygromycin, DHFR, GPT, zeocin, or histidinol; or a protein such as GFP or chloramphenicol acetyltransferase (CAT)).

A "promoter" is a control sequence that is a region of a nucleic acid sequence at which initiation and rate of transcription are controlled. It may contain genetic elements to which regulatory proteins and molecules may bind, such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence. Those of skill in the art of molecular biology generally are familiar with the use of promoters, enhancers, and cell type combinations for protein expression, for example, see Sambrook et al. (1989), incorporated herein by reference.

B. Host Cells

In the context of expressing a heterologous nucleic acid sequence, "host cell" refers to a prokaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

In particular embodiments of the invention, a host cell is a Gram-negative bacterial cell. These bacteria are suited for use with the invention in that they possess a periplasmic space between the inner and outer membrane and, particularly, the aforementioned inner membrane between the periplasm and cytoplasm, which is also known as the cytoplasmic membrane. As such, any other cell with such a periplasmic space could be used in accordance with the invention. Examples of Gram-negative bacteria that may find use with the invention may include, but are not limited to, *E. coli, Pseudomonas aeruginosa, Vibrio cholera, Salmonella typhimurium, Shigella flexneri, Haemophilus influenza, Bordotella pertussi, Erwinia amylovora, Rhizobium* sp.

An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (Stratagene®, La Jolla). Alternatively, bacterial cells such as *E. coli* LE392 could be used as host cells for bacteriophage.

Examples of mammalian host cells include Chinese hamster ovary cells (CHO-K1; ATCC CCL61), rat pituitary cells (GH1; ATCC CCL82), HeLa S3 cells (ATCC CCL2.2), rat hepatoma cells (H-4-II-E; ATCCCRL 1548), SV40-transformed monkey kidney cells (COS-1; ATCC CRL 1650), and murine embryonic cells (NIH-3T3; ATCC CRL 1658). The foregoing being illustrative but not limitative of the many possible host organisms known in the art.

Mammalian host cells expressing the polypeptide are cultured under conditions typically employed to culture the parental cell line. Generally, cells are cultured in a standard medium containing physiological salts and nutrients, such as standard RPMI, MEM, IMEM, or DMEM, typically supplemented with 5%-10% serum, such as fetal bovine serum. Culture conditions are also standard, e.g., cultures are incubated at 37° C. in stationary or roller cultures until desired levels of the proteins are achieved.

Many host cells from various cell types and organisms are available and would be known to one of skill in the art. Similarly, a viral vector may be used in conjunction with a prokaryotic host cell, particularly one that is permissive for replication or expression of the vector. Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

Numerous expression systems exist that comprise at least a part or all of the compositions discussed above. Such systems could be used, for example, for the production of a polypeptide product identified in accordance with the invention as capable of binding a particular ligand. Prokaryote-based systems can be employed for use with the present invention to produce nucleic acid sequences, or their cognate polypeptides, proteins, and peptides. Many such systems are commercially and widely available. Other examples of expression systems comprise of vectors containing a strong prokaryotic promoter such as T7, Tac, Trc, BAD, lambda pL, Tetracycline or Lac promoters, the pET Expression System, and an *E. coli* expression system.

In certain aspects of the invention, nucleic acid sequences encoding a polypeptide are disclosed. Depending on which expression system is used, nucleic acid sequences can be selected based on conventional methods. For example, if the polypeptide is derived from a human polypeptide and contains multiple codons that are rarely utilized in *E. coli*, then that may interfere with expression in *E. coli*. Therefore, the respective genes or variants thereof may be codon optimized for *E. coli* expression. Various vectors may be also used to express the protein of interest. Exemplary vectors include, but are not limited, plasmid vectors, viral vectors, transposon, or liposome-based vectors.

V. PROTEIN PURIFICATION

Protein purification techniques are well known to those of skill in the art. These techniques involve, at one level, the homogenization and crude fractionation of the cells, tissue, or organ into polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure peptide include ion-exchange chromatography, size-exclusion chromatography (SEC), reverse phase chromatography, hydroxyapatite chromatography, polyacrylamide gel electrophoresis, affinity chromatography, immunoaffinity chromatography, and isoelectric focusing. A particularly efficient method of purifying peptides is fast-performance liquid chromatography (FPLC) or even high-performance liquid chromatography (also called high-pressure liquid chromatography or HPLC). As is generally known in the art, it is believed that the order of conducting the various purification steps may be changed, or that certain steps may be omitted, and still result in a suitable method for the preparation of a substantially purified protein or peptide.

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various methods for quantifying the degree of purification of the protein or peptide are known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "fold purification number." The actual units used to represent the amount of activity will, of course, be dependent upon the particular assay technique chosen to follow the purification, and whether or not the expressed protein or peptide exhibits a detectable activity.

There is no general requirement that the protein or peptide will always be provided in its most purified state. Indeed, it is contemplated that less substantially purified products may have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "fold" purification than the same technique utilizing a low pressure chromatography system. Methods exhibiting a lower degree of relative purification may have advantages in total recovery of protein product, or in maintaining the activity of an expressed protein.

VI. PHARMACEUTICAL COMPOSITIONS

Where clinical application of a pharmaceutical composition containing a polypeptide or antibody is undertaken, it will generally be beneficial to prepare a pharmaceutical or therapeutic composition appropriate for the intended application. Generally, pharmaceutical compositions may comprise an effective amount of one or more polypeptide or additional agents dissolved or dispersed in a pharmaceutically acceptable carrier. In certain embodiments, pharmaceutical compositions may comprise, for example, at least about 0.1% of a polypeptide or antibody. In other embodiments, a polypeptide or antibody may comprise between about 2% to about 75% of the weight of the unit, or between about 25% to about 60%, for example, and any range derivable therein. The amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by FDA Office of Biological Standards.

Further in accordance with certain aspects of the present invention, the composition suitable for administration may be provided in a pharmaceutically acceptable carrier with or without an inert diluent. The carrier should be assimilable and includes liquid, semi-solid, i.e., pastes, or solid carriers. Examples of carriers or diluents include fats, oils, water, saline solutions, lipids, liposomes, resins, binders, fillers, and the like, or combinations thereof. As used herein, "pharmaceutically acceptable carrier" includes any and all aqueous solvents (e.g., water, alcoholic/aqueous solutions, ethanol, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings (e.g., lecithin), surfactants, antioxidants, preservatives (e.g., antibacterial or antifungal agents, antioxidants, chelating agents, inert gases, parabens (e.g., methylparabens, propylparabens), chlorobutanol, phenol, sorbic acid, thimerosal), isotonic agents (e.g., sugars, sodium chloride), absorption delaying agents (e.g., aluminum monostearate, gelatin), salts, drugs, drug stabilizers (e.g., buffers, amino acids, such as glycine and lysine, carbohydrates, such as dextrose, mannose, galactose, fructose, lactose, sucrose, maltose, sorbitol, mannitol, etc), gels, binders, excipients, disintegration agents, lubricants, fluid and nutrient replenishers, such like materials and combinations thereof, as would be known to one of ordinary skill in the art. Except insofar as any conventional media, agent, diluent, or carrier is detrimental to the recipient or to the therapeutic effectiveness of the composition contained therein, its use in administrable composition for use in practicing the methods is appropriate. The pH and exact concentration of the various components in a pharmaceutical composition are adjusted according to well-known parameters. In accordance with certain aspects of the present invention, the composition is combined with the carrier in any convenient and practical manner, i.e., by solution, suspension, emulsification, admixture, encapsulation, absorption, grinding, and the like. Such procedures are routine for those skilled in the art.

Certain embodiments of the present invention may comprise different types of carriers depending on whether it is to be administered in solid, liquid, or aerosol form, and whether it needs to be sterile for the route of administration, such as injection. The compositions can be formulated for administration intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference) .Typically, such compositions can be prepared as either liquid solutions or suspensions; solid forms suitable for use to prepare solutions or suspensions upon the addition of a liquid prior to injection can also be prepared; and, the preparations can also be emulsified. In some embodiments, a therapeutic protein comprising a mutant or variant Fc domain is administered to a mammalian subject (e.g., a human) via injection or intravenous administration.

The polypeptides may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine.

In further embodiments, the present invention may concern the use of a pharmaceutical lipid vehicle composition that includes polypeptides, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods.

One of ordinary skill in the art would be familiar with the range of techniques that can be employed for dispersing a composition in a lipid vehicle. For example, the polypeptide or a fusion protein thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes. In some embodiments, an antibody comprising a mutant or variant Fc domain as described herein may be included in antibody-targeted liposomes.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above. The practitioner responsible for administration will, in any event, determine the concentration of active ingredient(s) in a composition and appropriate dose(s) for the individual subject.

It is not intended that the present invention be limited by the particular nature of the therapeutic preparation. For example, such compositions can be provided in formulations together with physiologically tolerable liquid, gel, or solid carriers, diluents, and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects. The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

VII. METHODS OF TREATING

Certain aspects of the present invention provide a polypeptide for treating diseases, such as tumors, e.g., with a therapeutic protein or antibody comprising a mutant or variant Fc domain as described herein. Particularly, the polypeptide may have human polypeptide sequences and thus may prevent allergic reactions in human patients, allow repeated dosing, and increase the therapeutic efficacy.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an antibody that targets CDC to cancer cells without triggering cancer cell proliferation.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant;

lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The polypeptide may be used herein as an antitumor agent in a variety of modalities for triggering complement activation in tumor tissue or for triggering complement activation where it is considered desirable. In a particular embodiment, the invention contemplates methods of using a polypeptide as an antitumor agent, and therefore comprises contacting a population of tumor cells with a therapeutically effective amount of a polypeptide for a time period sufficient to inhibit tumor cell growth.

In one embodiment, the contacting in vivo is accomplished by administering, by intravenous intraperitoneal, or intratumoral injection, a therapeutically effective amount of a physiologically tolerable composition comprising a polypeptide of this invention to a patient. The polypeptide can be administered parenterally by injection or by gradual infusion over time. The polypeptide can be administered intravenously, intraperitoneally, orally, intramuscularly, subcutaneously, intracavity, transdermally, dermally, can be delivered by peristaltic means, or can be injected directly into the tissue containing the tumor cells.

Therapeutic compositions comprising polypeptides are conventionally administered intravenously, such as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial and booster administration are also contemplated and are typified by an initial administration followed by repeated doses at one or more hour intervals by a subsequent injection or other administration. Exemplary multiple administrations are described herein and are particularly preferred to maintain continuously high serum and tissue levels of polypeptide. Alternatively, continuous intravenous infusion sufficient to maintain concentrations in the blood in the ranges specified for in vivo therapies are contemplated.

It is contemplated that a polypeptide of the invention can be administered systemically or locally to treat disease, such as to inhibit tumor cell growth or to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive.

A therapeutically effective amount of a polypeptide is a predetermined amount calculated to achieve the desired effect, i.e., to trigger CDC in the tumor tissue, and thereby mediate a tumor-ablating pro-inflammatory response. Thus, the dosage ranges for the administration of polypeptide of the invention are those large enough to produce the desired effect in which the symptoms of tumor cell division and cell cycling are reduced. The dosage should not be so large as to cause adverse side effects, such as hyperviscosity syndromes, pulmonary edema, congestive heart failure, neurological effects, and the like. Generally, the dosage will vary with age of, condition of, sex of, and extent of the disease in the patient and can be determined by one of skill in the art. The dosage can be adjusted by the individual physician in the event of any complication.

VIII. COMBINATION THERAPY

In certain embodiments, the compositions and methods of the present embodiments involve administration of a polypeptide or antibody in combination with a second or additional therapy. Such therapy can be applied in the treatment of any disease that is responsive to CDC. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve administering a polypeptide or antibody and a second therapy. The second therapy may or may not have a direct cytotoxic effect. For example, the second therapy may be an agent that upregulates the immune system without having a direct cytotoxic effect. A tissue, tumor, or cell can be exposed to one or more compositions or pharmacological formulation(s) comprising one or more of the agents (e.g., a polypeptide or an anti-cancer agent), or by exposing the tissue, tumor, and/or cell with two or more distinct compositions or formulations, wherein one composition provides 1) a polypeptide or antibody, 2) an anti-cancer agent, or 3) both a polypeptide or antibody and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic polypeptide or antibody and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

A polypeptide or antibody may be administered before, during, after, or in various combinations relative to an anti-cancer treatment. The administrations may be in intervals ranging from concurrently to minutes to days to weeks. In embodiments where the polypeptide or antibody is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the polypeptide and the anti-cancer therapy within about 12 to 24 or 72 h of each other and, more particularly, within about 6-12 h of each other. In some situations, it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a polypeptide or antibody is "A" and an anti-cancer therapy is "B":

| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of any polypeptide or therapy of the present embodiments to a patient will follow general protocols for the administration of such compounds, taking into account the toxicity, if any, of the agents. Therefore, in some embodiments there is a step of monitoring toxicity that is attributable to combination therapy. In some embodiments involving treating a cancer in a subject, the second therapy may be, e.g., a chemotherapy, a radiotherapy, an immunotherapy, a gene therapy, or a surgery.

A. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammall and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cis-platin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine,plicomycin, gemcitabien, navelbine, farnesyl-protein tansferase inhibitors, transplatinum, and pharmaceutically acceptable salts, acids, or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

The skilled artisan will understand that immunotherapies may be used in combination or in conjunction with methods of the embodiments. In the context of cancer treatment, immunotherapeutics, generally, rely on the use of immune effector cells and molecules to target and suppress immune cells. Blinatumomab (Blincyto®) is such an example. Checkpoint inhibitors, such as, for example, ipilumimab, are another such example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions may increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IX. KITS

Certain aspects of the present invention may provide kits, such as therapeutic kits. For example, a kit may comprise one or more pharmaceutical composition as described herein and optionally instructions for their use. Kits may also comprise one or more devices for accomplishing administration of such compositions. For example, a subject kit may comprise a pharmaceutical composition and catheter for accomplishing direct intravenous injection of the composition into a cancerous tumor. In other embodiments, a subject kit may comprise pre-filled ampoules of a polypeptide, optionally formulated as a pharmaceutical, or lyophilized, for use with a delivery device.

Kits may comprise a container with a label. Suitable containers include, for example, bottles, vials, and test tubes. The containers may be formed from a variety of materials, such as glass or plastic. The container may hold a composition that includes a polypeptide that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

X. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Library Construction Strategy for the Isolation of IgG1 Fc Domains

*E. coli* does not encode a protein glycosylation machinery and therefore the Fc domain of IgG expressed in the periplasm of *E. coli* is aglycosylated, lacking the glycan that is normally appended to N297 of the Fc domain. Aglycosylated Fc domains display a greater degree of conformational flexibility which results in highly attenuated or no detectable binding to effector FcγRs (FcγRIA, FcγRIIA, FcγRIIB, FcγRIIc, FcγRIIIA, FcγRIIIB) and C1q (Jefferis et al., 2005; Borrok et al., 2012), but loss of glycan does not affect the pH-dependent FcRn binding properties of IgG. To isolate Fc domain variants containing mutations that enable enhanced binding to FcRn than wild type IgG, the binding sites of Fc domain for FcRn were randomized. Random amino acid substitutions were introduced at Asp249, Thr250, Leu251, Met252, Ile253, Ser254, Arg255, Val308, Leu309, Gln311, Asp312, Leu314, Glu430, Leu432, Tyr436, and Gln438. Eight primers (SEQ ID NOs:12-19) were designed and used for mutagenesis as described in example 2 below (Table 4).

TABLE 4

Primers used in this study
(provided as SEQ ID NOs: 12-19)

| SEQ ID NO: | Sequence Name: | Primer nucleotide sequence (5'→3') |
|---|---|---|
| 12 | PCHT01 | GTT ATT ACT CGC GGC CCA GCC GGC CAT GGC GGA GGT TC A A |
| 13 | PCHT02 | CTT GGG TTT TGG GGG GAA GAG GAA GAC |
| 14 | PCHT03 | GTC TTC CTC TTC CCC CCA AAA CCC AAG VRK VMB CDC V WB VWH VRK VRK ACC CCT GAG GTC ACA TGC GTG GTG |
| 15 | PCHT04 | GAC CTT GCA CTT GTA CTC CTT GCC ATT GHG CCA MYB GH G GTG VWS VWS GGT GAG GAC GCT GAC CAC ACG GTA |
| 16 | PCHT05 | AAT GGC AAG GAG TAC AAG TGC AAG GTC |
| 17 | PCHT06 | CGG GGA CAG GGA GAG GCT CTT MYB CGT GTV GTG MYB G TG GHG AGC MYB ATG CAT CAC GGA GCA TGA GAA GAC GT T |
| 18 | PCHT07 | AAG AGC CTC TCC CTG TCC CCG |
| 19 | PCHT08 | GCG GCC GCG AAT TCG GCC CCC GAG GCC CCT TTA CCC GG G G |

Example 2

The Construction of Libraries for Engineering Fc Domain

All plasmids and primers are described in Tables 4, 10 and 11. All primers were synthesized by Integrated DNA Technologies. IgG polypeptides were expressed and displayed on the inner membrane of *E. coli* using the vectors: pBAD30-PelB-VL-Ck-NlpA-VL-Ck-His-cMyc and pMopac12-pelB-IgG-VH-CH1-CH2-CH3-FLAG (Jung et al., 2012 and Lee et al., 2017) (FIG. 1-2). In order to randomize the FcRn-binding sites of Fc domain, the eight primers (SEQ ID NOs: 12-19) were designed (Table 4 and FIG. 2). Four fragments of the heavy chain gene of IgG1 were amplified with the eight primers and stitched together by overlap extension with PCHT01 (SEQ ID NO: 12) and PCHT08 (SEQ ID NO: 19). The Fc library genes were amplified with the following thermocycling program: One cycle of 94° C. for 5 min; 30 cycles of 94° C. for 1 min, 55° C. for 1 min, and 72° C. for 1.5 min; one cycle of 72° C. for 5 min. The amplified heavy chain library genes were ligated in-frame into SfiI digested pMopac12-pelB-IgG-VH-CH1-CH2-CH3-FLAG vector. The resulting plasmids were transformed into *E. coli* JUDE-1 cells containing the plasmid pBAD30-PelB-VL-Ck-NlpA-VL-Ck-His-cMyc. (Jung et al., 2010; Jung et al., 2012; Lee et al., 2017). The sizes of library were 1×10$^8$.

Example 3

Preparation of Human FcRn-β2m-GST

Plasmid for mammalian expression of FcRn was constructed as described previously (Lee et al., 2017). FcRn-β2m-GST was produced by transient transfection of HEK293F cells (Invitrogen) using the pcDNA3.4 (Thermofisher). The transfected HEK293F cells were cultured for 5 days in a 5% $CO_2$ incubator at 37° C. The supernatant was collected by centrifugation at 4,000×g for 10 min and filtered using a 0.22 μm polyethersulfone (PES) membrane filter (PALL). The FcRn-β2m-GST was purified with Glutathione Sepharose (GE Healthcare) affinity columns according to the manufacturer's instructions. To remove lipopolysaccharide (LPS) and non-specifically bound protein, the FcRn-β2m-GST-bound resins were washed with 50 mL of PBS containing 0.1% Triton® X-114 (Sigma-Aldrich) and 50 mL of PBS. The FcRn-β2m-GST was eluted with PBS containing 10 mM reduced L-glutathione. The buffer of eluted FcRn-β2m-GST was exchanged to PBS using an Amicon Ultra-4 (Millipore) unit. And single chain FcRn-β2m-his (scFcRn) was purchased from Acro Biosystems (Cat. No. FCM-H5286). The human scFcRn was labeled with FITC using FITC Fast Conjugation Kit (Abcam, Cat. No. ab188285) according to the manufacturer's instructions. In addition, the human FcRn-β2m-GST was labeled with R-phycoerythrin (R-PE) using an EasyLink R-PE Conjugation Kit (Abcam) according to the manufacturer's instructions.

Plasmids for mammalian expression of FcγRs were constructed as described previously (Jung et al., 2012 and Lee et al., 2017). FcγRI-His, FcγRIIa-$_{H131}$-GST, FcγRIIa-$_{R131}$-GST, FcγRIIb-GST, FcγRIIIa-$_{V158}$-GST, and FcγRIIIa-$_{F158}$-GST were produced by transient transfection of HEK293F cells (Invitrogen) using the pMAZ-IgH (U.S. Pat. No. 8,043,621) derived expression vectors described in Table 11. Detailed procedures were described in above paragraph. The FcγRI-His was purified with Ni-NTA (GE Healthcare) affinity columns according to the manufacturer's instructions. The FcγRI-His was eluted with PBS containing 250 mM imidazole. The FcγRs-GSTs were purified with same methods for FcRn-β2m-GST. The buffer of all eluted FcγRs was exchanged to PBS by Amicon Ultra-4 (Millipore).

Example 4

Screening of Fc Libraries for FcRn

*E. coli* JUDE-1 cells were cultured overnight at 37° C. and 250 rpm in Terrific Broth (TB) with chloramphenicol (40 μg/mL) and kanamycin (50 μg/mL). Following overnight growth, cells were diluted 1:50 in fresh 100 mL TB media with two antibiotics. *E. coli* JUDE-1 cells were cultured at 37° C. and 250 rpm until the $OD_{600}$ reached a value of approximately 0.4. Then, 1 mM isopropyl-β-D-thiogalactopyranoside (IPTG, Sigma Aldrich) and 2% L-arabinose (Sigma-Aldrich) were added to the *E. coli* JUDE-1 cells to facilitate the protein expression, and the cells were then further incubated at 25° C. for 20 h. Cultures (8 mL culture volume) were harvested by centrifugation and washed two times in 1 mL of ice-chilled 10 mM Tris-HCl (pH8.0). The washed cells were resuspended in 1 mL of ice-chilled STE solution (0.5 M sucrose, 10 mM Tris-HCl, 10 mM EDTA, pH 8.0) and incubated at 37° C. for 30 min. The cells were centrifuged at 13,000 rpm for 1 min and washed with 1 mL of Solution A (0.5 M sucrose, 20 mM $MgCl_2$, 10 mM MOPS, pH6.8). The washed cells were incubated in 1 mL of Solution A with 1 mg/mL hen egg lysozyme (Sigma-Aldrich) at 37° C. for 15 min. After centrifugation at 13,000 rpm for 1 min, the pelleted spheroplasts were resuspended in 1 mL of cold PBS (Jung et al., 2010; Jung et al., 2012; Lee et al., 2017).

Figure 3A:
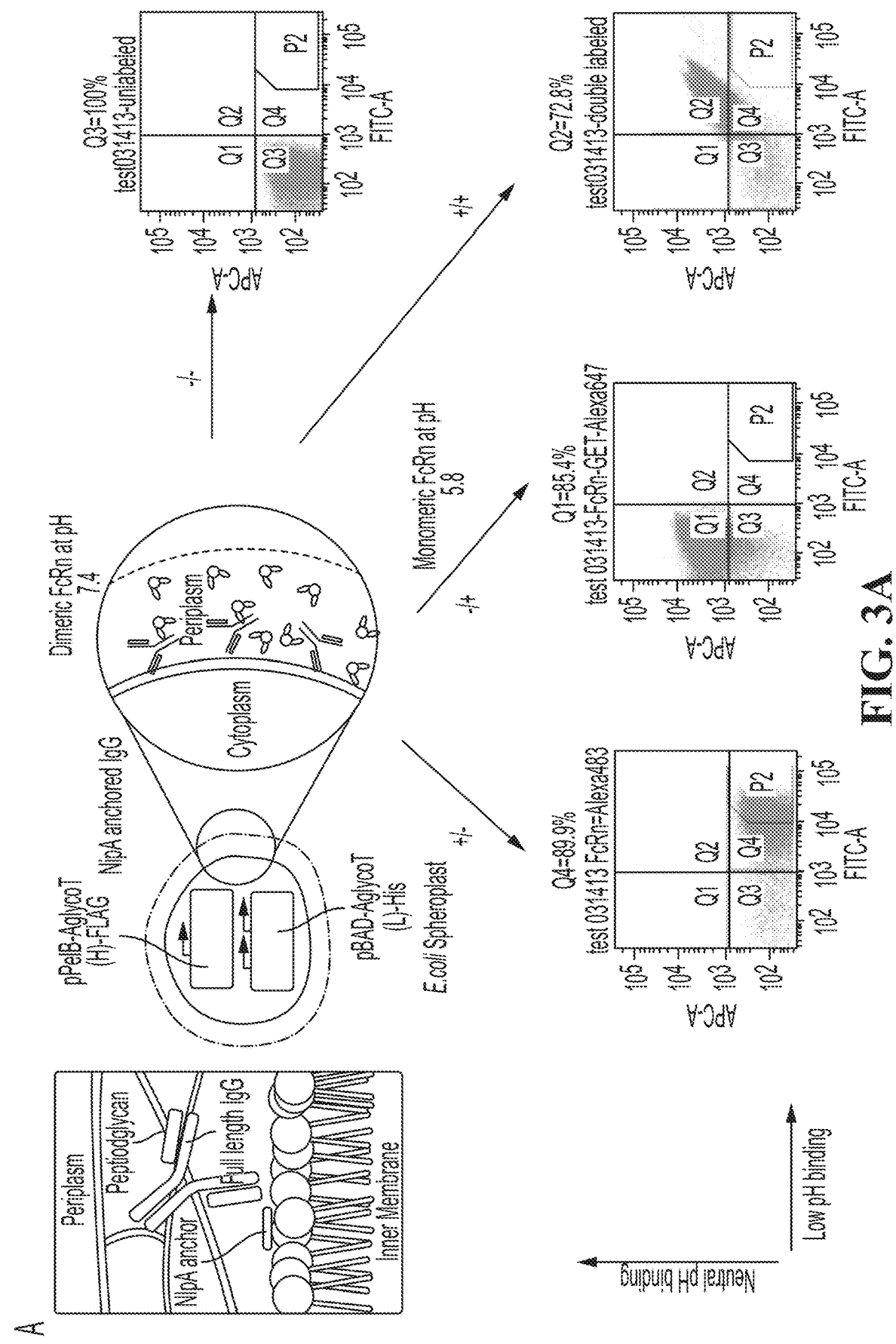
FIGS. 3A-B. Screening strategy of Fc library and the results.
Figure 3B:
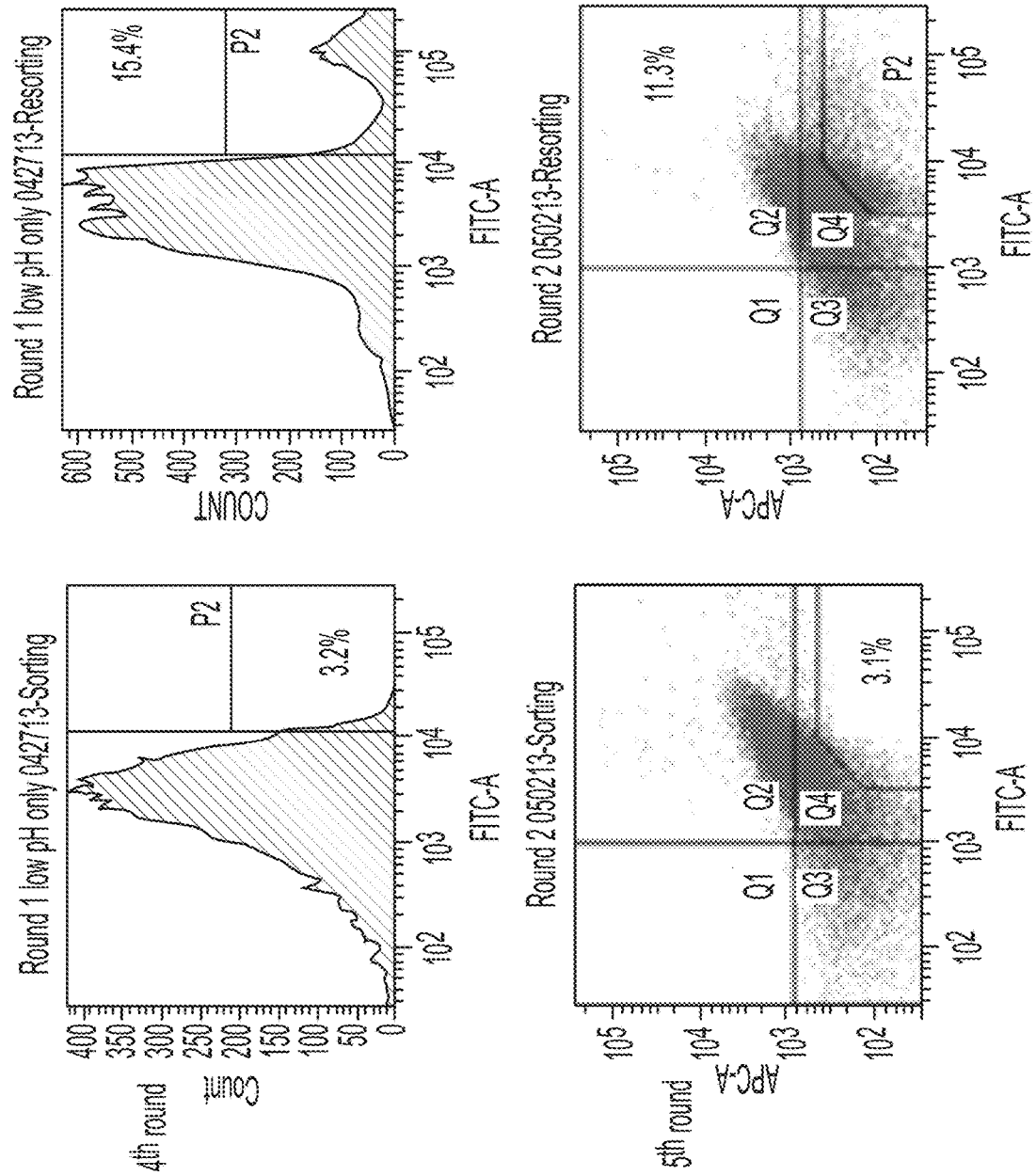

To isolate enhanced FcRn-binding IgG1 variants, cells expressing the library described in Example 1 and 2 were labeled with 100 nM FcRn-β2m-FITC and screened by on FACSAria™ (BD Biosciences). For each of four rounds FACS of screening, the top 3% of the population showing the highest fluorescence was recovered and these sorted spheroplasts were resorted immediately to remove false positives. The heavy chain genes in the sorted spheroplasts were rescued by PCR using two primers (PCHT01 and PCHT08) after boiling for 5 min and ligated into SfiI-cut pMopac12 vector. The ligated plasmids were transformed in *E. coli* JUDE-1 cells. Transformants were selected on chloramphenicol- and kanamycin-containing media and the spheroplasts were prepared for the next round of screening using 100 nM of FcRn-β2m-FITC (FIGS. 3A-B). In order to isolate pH-dependent binding IgG variants for FcRn, the spheroplasts were labeled with 100 nM of single chain FcRn-β2m-FITC at pH 5.8 PBS and then incubated with FcRn-β2m-GST-APC at pH 7.4 PBS (FIG. 3A). Next, spheroplasts which has FITC-positive and APC-negative signals are sorted (FIG. 3B).

Example 5

FACS Analysis of IgG Variants

Figure 4:
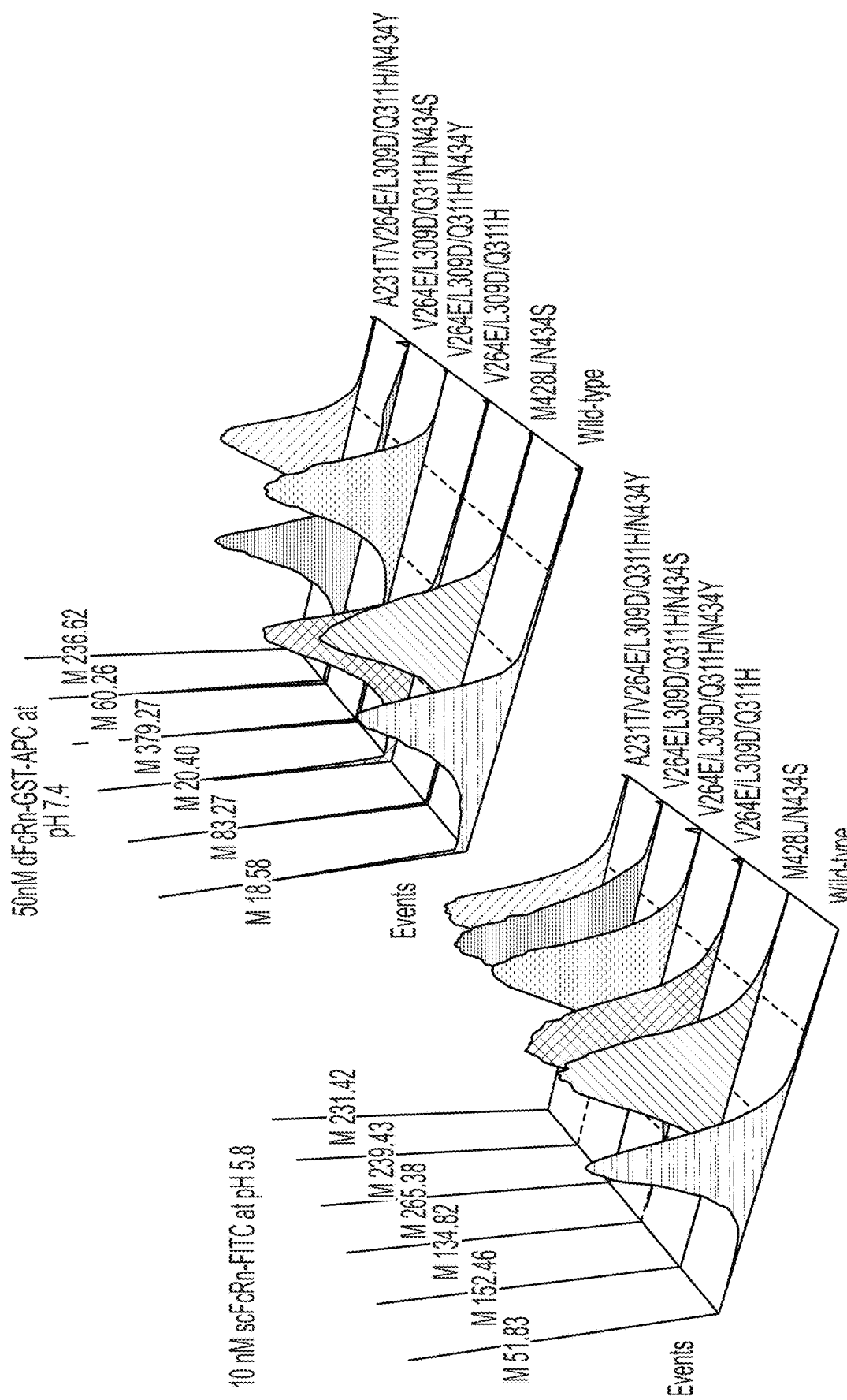
FIG. 4. FACS analysis of the isolated Fc variants. *E. coli* spheroplasts expressing Fc variants were labeled with 10 nM scFcRn-FITC at pH 5.8 or 50 nM dFcRn-APC at pH 7.4.

Four IgG variants were identified, EDH (V264E, L309D, and Q311H), EDHS (SEQ ID NO: 5; V264E, L309D, Q311H, and N434S), EDHY (SEQ ID NO: 6; V264E, L309D, Q311H, and N434Y), and TEDHY (A231T, V264E, L309D, Q311H, and N434Y). The respective genes were transformed in *E. coli* JUDE-1, the cells were spheroplasted and analyzed with 10 nM of FcRn-β2m-FITC in pH 5.8 PBS or 50 nM of FcRn-β2m-GST-APC in pH 7.4 PBS by FACS. As shown in FIG. 4, four IgG variants showed 2.6-5.1 fold-higher mean fluorescence intensity (MFI) values relative to wild-type aglycosylated IgG for FcRn-β2m-FITC. For FcRn-β2m-GST-APC in pH 7.4 PBS, EDHY and TEDHY showed significantly high binding activities than wild type IgG1 while EDH and EDHS showed similar or slightly increased binding activities comparing with wild type IgG1.

Example 6

Expression and Purification of the Selected Mutant IgG Variants

All plasmids and primers are described in Tables 4, 10 and 11. The four mutants Fc genes were amplified from pMopac12-pelB-IgG-VH-CH1-CH2-CH3-FLAG using two specific primers (TH083 (SEQ ID NO: 20) and TH084 (SEQ ID NO: 21)). pcDNA3.4-IgH plasmids were amplified using two specific primers (TH081 (SEQ ID NO: 22) and TH082 (SEQ ID NO: 23)). The four Fc genes were cloned into pcDNA3.4 using a Gibson Assembly® cloning kit (NEB) according to the manufacturer's instructions (Lee et al., 2017). The Gibson assembled mixtures were transformed into *E. coli* JUDE-1 cells and their sequences confirmed. And the Fab of trastuzumab was used. The heavy chain genes of four trastuzumab-Fc variants were transiently transfected with an equal mass of light chain plasmid in HEK293F cells (Invitrogen). After incubation in a 5% $CO_2$ incubator at 37° C. for six days, the supernatants were collected by centrifugation at 4,000×g for 10 min and filtered using a 0.22 μm PES membrane filter (PALL). The filtered supernatants were passed over Protein A high capacity agarose resin (Thermo Scientific) three times. To remove LPS and non-specifically bound protein, the IgG-bound resins were washed with 50 mL PBS containing 0.1% Triton®X-114 (Sigma-Aldrich) and 50 mL PBS. All IgG variants were eluted with 100 mM glycine buffer (pH 3.0) and immediately neutralized with 1M Tris-HCl buffer (pH 8.0). The buffer of all eluted trastuzumab-Fc antibody variants was exchanged to PBS by Amicon® Ultra-4 (Millipore). The purity of reduced or non-reduced proteins for the trastuzumab-Fc antibody variants and for authentic (w.t.) trastuzumab expressed in HEK293 cells as above were assessed by 4%-20% gradient SDS-PAGE gel (NuSep) under reducing and non-reducing conditions.

Example 7

Binding Properties of the Selected IgG Variants to Human FcRn and FcγRs

The binding affinities of the three IgG variants, EDH, EDHS and EDHY, to human FcRn was evaluated with enzyme-linked immunosorbent assay (ELISA) and surface plasmon resonance (SPR).

Figure 5A:
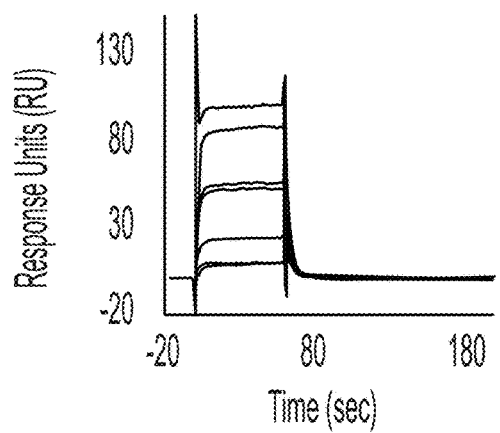
FIGS. 5A-F. Surface plasmon resonance (SPR) sensorgrams of Heceptin (FIG. 4A), and the selected IgG variants, EDH (FIG. 4B), EDHY (FIG. 4C), EDHS (FIG. 4D), Herceptin-LS (FIG. 4E), Herceptin-YTE (FIG. 4F). Each antibody was immobilized on CM5 chip and the serially diluted scFcRn proteins in pH 5.8 PBS were injected into CM5 chip.
Figure 5B:
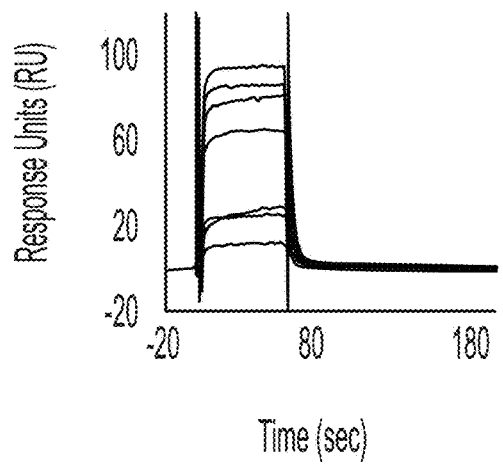
Figure 5C:
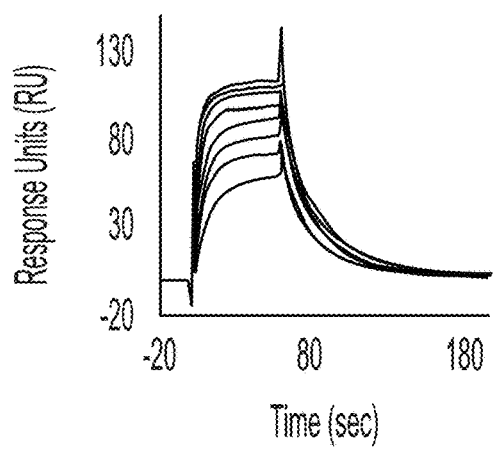
Figure 5D:
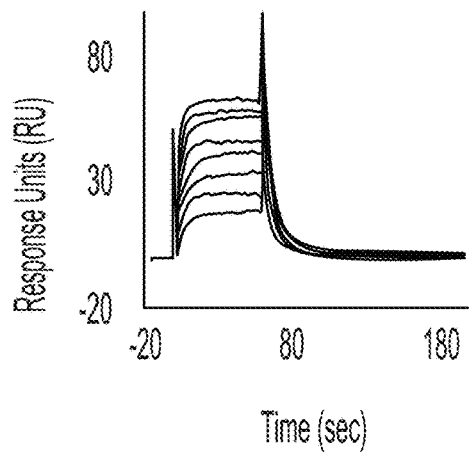

SPR measurements: SPR measurements were performed on Biacore® 3000 (GE Healthcare) instrument. Reference channel of the CM5 sensor chip was closed without immobilization of any proteins to subtract buffer effect and non-specific binding signal. Clinical grade Herceptin, EDH, EDHY, and EDHS were immobilized on the CM5 sensor chips by amine coupling method at pH 5.0. The serially diluted FcRn (400–25 nM) protein was injected onto the CM5 chip at 30 μL/min for 1 min in pH 5.8 phosphate buffered saline (PBS, 1.8 mM $KH_2PO_4$, 10 mM $Na_2HPO_4$, 2.7 mM KCl, and 137 mM NaCl). The chip was regenerated after each binding event with 10 mM tris (pH 8.0) with a contact time of 1 min. The resulting sensorgrams were fit with 1:1 Langmuir model using Biaevaluation 3.0 software (FIG. 5; Table 5). As a control group, previously reported Herceptin-LS (M428L/N434S, Xencor) and Herceptin-YTE (M252Y/S254T/T256E, Medimmune) were immobilized on the CM5 sensor chips by same method and analyzed. Herceptin-EDH showed similar affinity comparing with wild type Herceptin (FIG. 5A-B; Table 5). In other hands, Herceptin-EDHY and Herceptin-EDHS showed 19.6 and 5.9-fold enhanced affinity than Herceptin, respectively (FIG. 5C-D; Table 5).

Figure 5E:
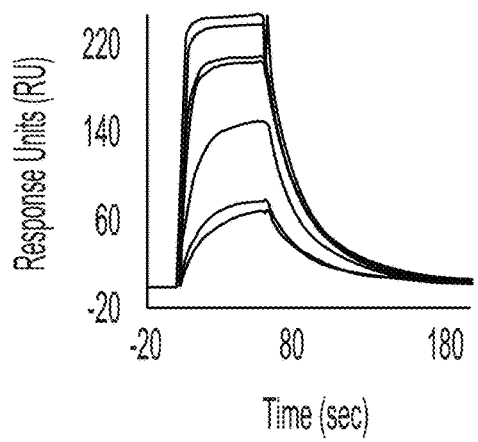
Figure 5F:
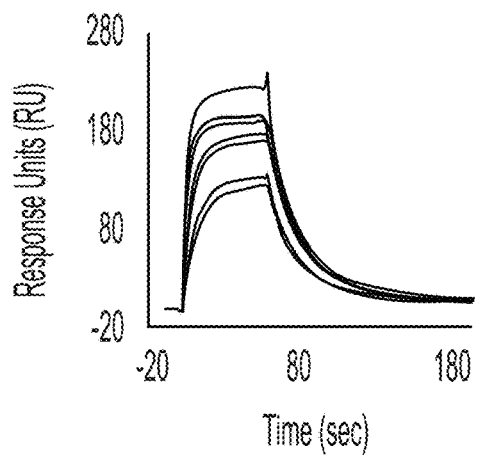
Figure 6:
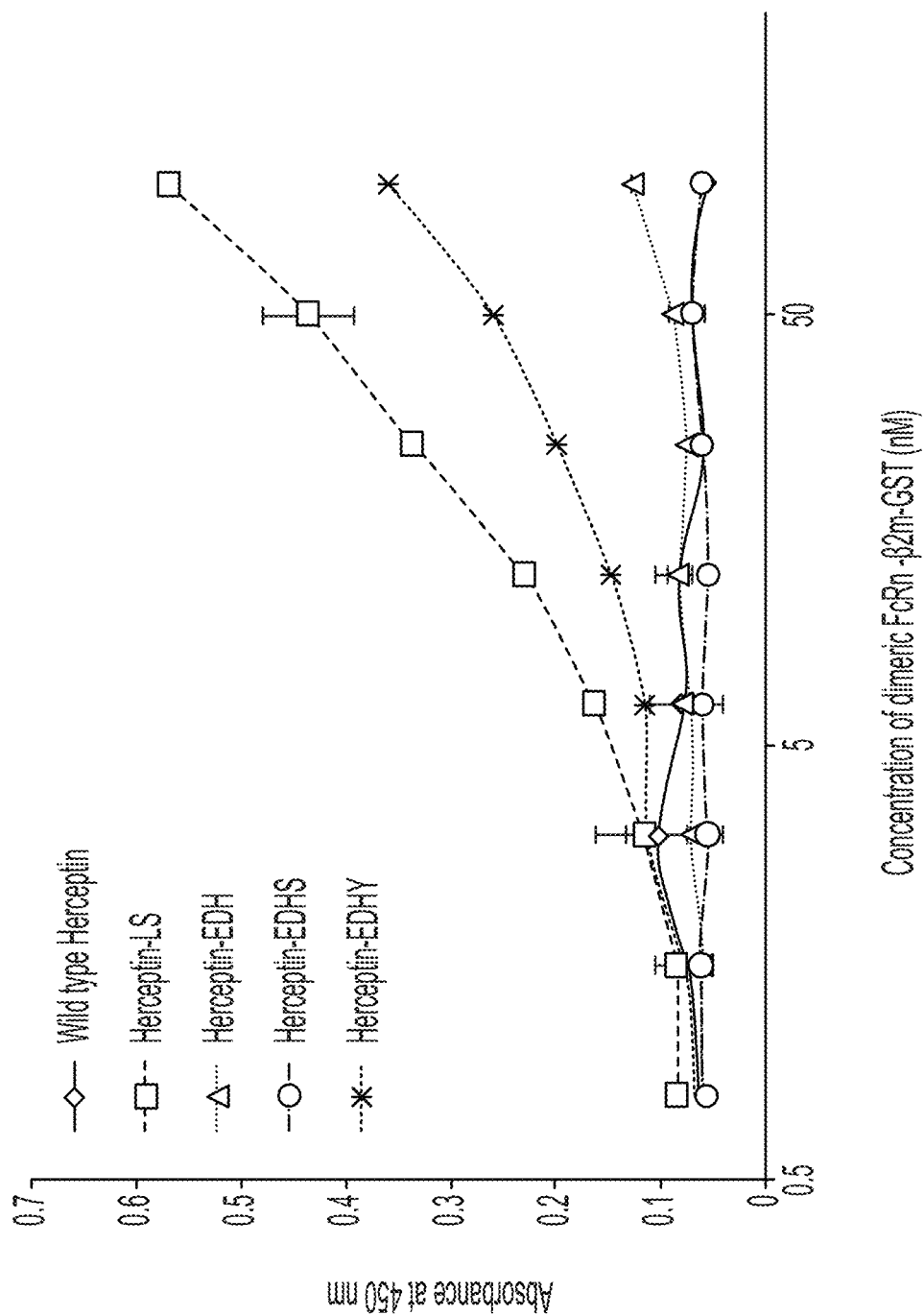
FIG. 6. The binding activities of antibody variants with dFcRn at pH 7.4. Each antibody were coated in 96 wells and the binding activities of dFcRn were detected by anti-GST HRP.
Figure 7A:
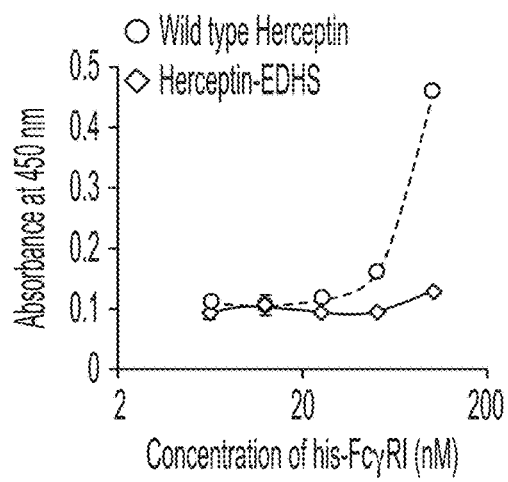
FIGS. 7A-F. ELISA results of wild type Herceptin and the selected IgG variant Herceptin-EDHS to FcγRs; monomeric FcγRI (FIG. 7A), dimeric FcγRIIA$_{H131}$ (FIG. 7B), dimeric FcγRIIA$_{R131}$ (FIG. 7C), dimeric FcγRIIB (FIG. 7D) dimeric FcγRIIIA$_{V157}$ (FIG. 7E), and dimeric FcγRIIIA$_{F157}$ (FIG. 7F).
Figure 7B:
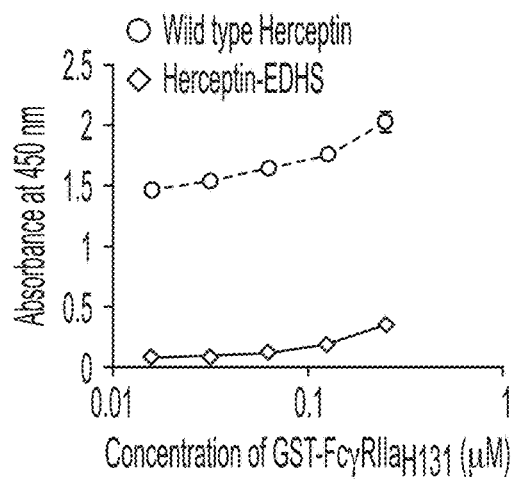
Figure 7C:
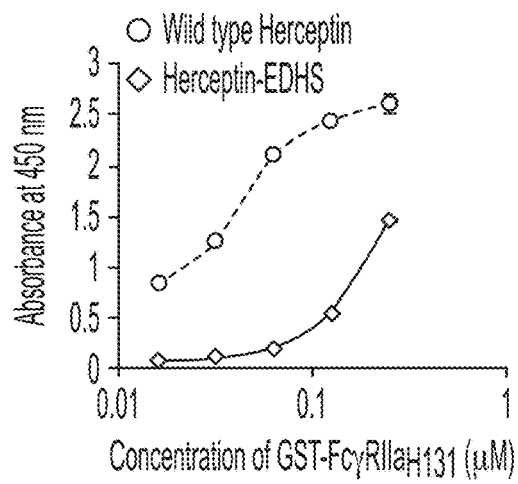
Figure 7D:
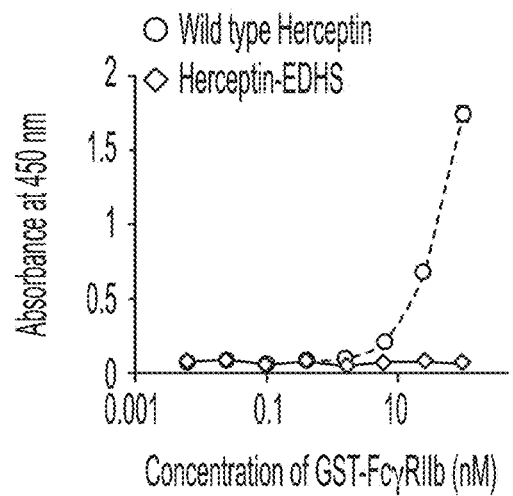
Figure 7E:
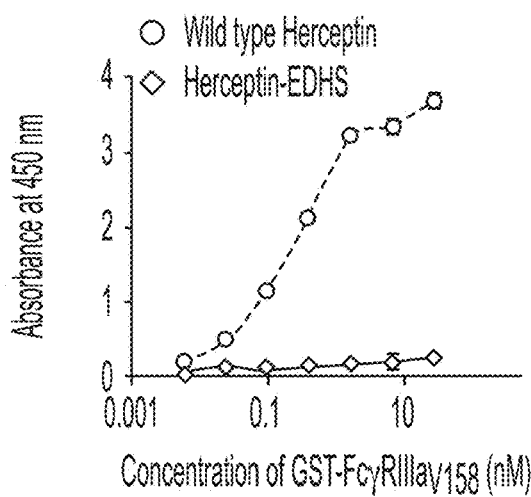
Figure 7F:
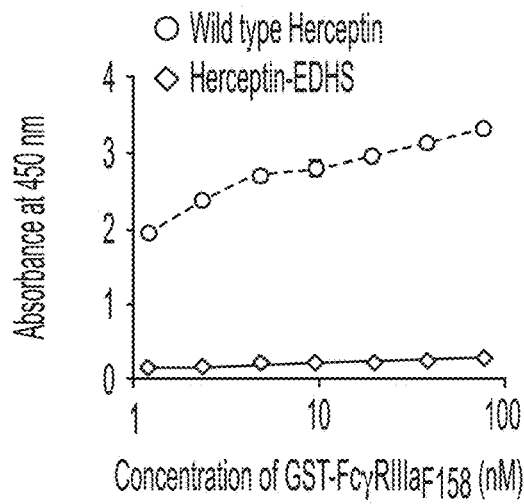

Herceptin-LS and Herceptin-YTE showed 10 and 23.9-fold enhanced affinity than Herceptin, respectively, and these were consistent results with previous report (FIG. 5E-F; Table 5).

TABLE 5

$K_D$ values of the isolated Fc variants for FcRn at pH 5.8

| | $K_{on}$ ($10^5 M^{-1} sec^{-1}$) | $K_{off}$ ($10^{-2} sec^{-1}$) | $K_D$ (nM) |
|---|---|---|---|
| Herceptin | 5.4 ± 0.30 | 29 ± 0.85 | 550 ± 46 |
| Herceptin-LS | 6.2 ± 1.6 | 3.3 ± 0.07 | 55 ± 3.2 |
| Herceptin-YTE | 8.2 ± 1.4 | 2.3 ± 0.1 | 23 ± 1.0 |
| Herceptin-EDH | 4.65 ± 0.38 | 23 ± 0.01 | 487 ± 35 |
| Herceptin-EDHY | 14 ± 2.0 | 3.8 ± 0.11 | 28 ± 4.7 |
| Herceptin-EDHS | 12 ± 1.3 | 11 ± 1.0 | 93 ± 1.3 |
| Herceptin-DHS | 7.77 ± 0.24 | 8.7 ± 0.09 | 111 ± 20 |

ELISA measurements of IgG variants with hFcRn: 1 μg of each of EDH, EDHY, EDHS, or Herceptin were coated onto a 96-well EIA/RIA plate (Qiagen) at 4° C overnight, and the plates were washed three times with PBS containing 0.05% Tween® 20 (PBST). The plates were blocked for 1 h at room temperature with 1× fish gelatin blocking solution (Biotium) in PBS and washed three times with PBST. Serially diluted dimeric FcRn-β2m-GST (100 nM–0.8125 nM) was then added to the plates. After 1 h of incubation at room temperature, the plates were washed with PBST and then they were incubated with 50 μL of PBS containing 1:5000 goat anti-GST HRP (GE Healthcare) for 1 h. After washing with PBST three times, 50 μL TMB substrate was added per well (Thermo Scientific), 50 μL of 1 M $H_2SO_4$ was added to neutralize, and the absorbance at 450 nm was recorded. Wild type Herceptin, Herceptin-EDH, and Herceptin-EDHS did not show any binding activities for dimeric FcRn-β2m-GST at physiological pH 7.4. In the other hands, Herceptin-LS and Herceptin-EDHY showed significant binding activities for dimeric FcRn-β2m-GST at physiological pH 7.4.

Notably, EDHS showed 5.9-fold enhanced $K_D$ at pH 5.8 and no-binding signals at pH 7.4 for FcRn.

ELISA measurements of IgG variants with hFcγR: The binding properties of EDHS to human FcγRs were assayed. Briefly, 1 μg of each of wild type Herceptin or Herceptin-EDHS was coated onto a 96-well EIA/RIA plate (Qiagen) at 4° C. overnight, and the plates were washed three times with PB ST. The plates were blocked for 1 h at room temperature with 1% BSA in PBS and washed three times with PBST. The serially diluted monomeric His-FcγRI, dimeric GST-FcγRIIa$_{R131}$, dimeric GST-FcγRIIa$_{H131}$, dimeric GST-FcγRIIb, dimeric GST-FcγRIIIa$_{V158}$, and dimeric GST-FcγRIIIa$_{F158}$ were then added to the plates. After 1 h of incubation at room temperature, the plates were washed with PBST and were incubated with 50 μL of PBS containing 1:5000 goat anti-His or anti-GST HRP (GE Healthcare) for 1 h. After three times of washing with PBST, 50 μL TMB substrate was added per well (Thermo Scientific), 50 μL of 1 M $H_2SO_4$ was added to neutralize, and the absorbance at 450 nm was recorded. The Herceptin-EDHS showed significantly decreased binding signals with all FcγRs comparing with wild type Herceptin (FIGS. 7A-F).

Example 8

Construction and Characterization of DHS-Fc Variant

Effector function by FcγRs are essential antibody-mediated immune response to remove pathogen. Herceptin-EDHS failed to bind to the effector FcγRs Herceptin-EDHS contains four amino acids substitutions, V264E, L309D, Q311H, and N434S. V264E impairs the glycosylation of IgG which is critical for binding to effector FcRs (Xiaojie Yu et al., 2013). Therefore, we constructed Herceptin-DHS (SEQ ID NO: 7; L309D; Q311H; N434S) without the V264E mutation. The binding affinities of DHS to human FcRn and FcγRs were evaluated with enzyme-linked immunosorbent assay (ELISA) and surface plasmon resonance (SPR).

Figure 8:
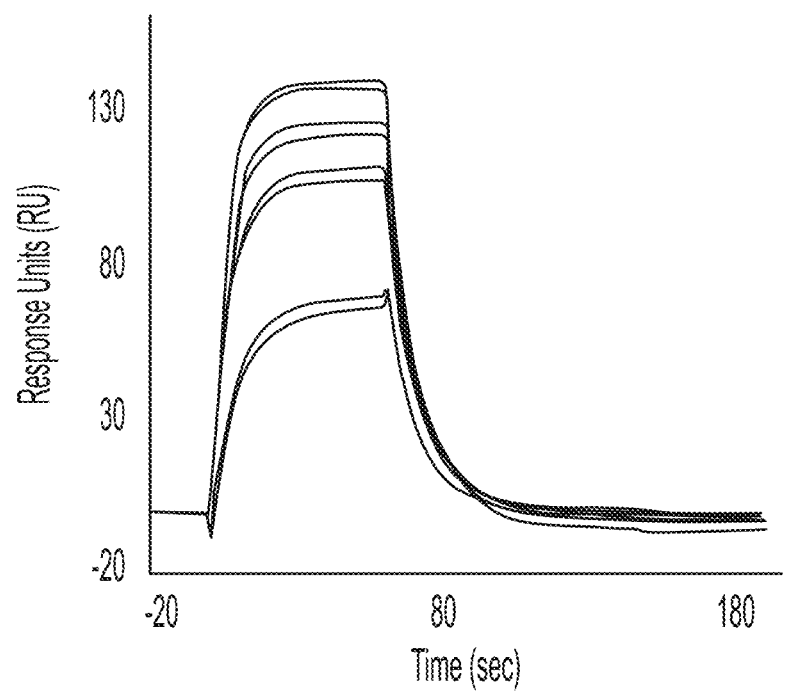
FIG. 8. Surface plasmon resonance (SPR) sensorgrams of Heceptin-DHS. Antibody was immobilized on CM5 chip and the serially diluted scFcRn proteins in pH 5.8 PBS were injected into CM5 chip.
Figure 9:
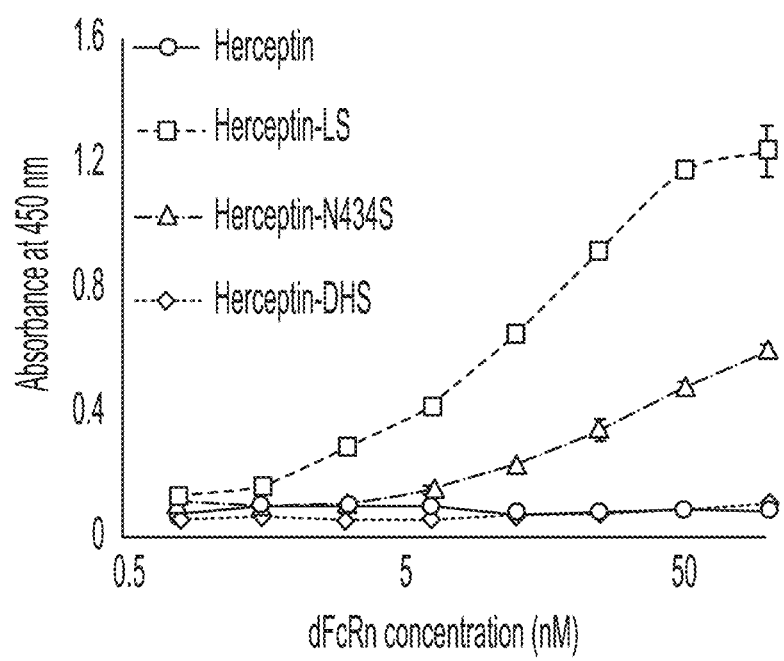
FIG. 9. The binding activities of antibody variants with dimeric FcRn (dFcRn) at pH 7.4. Each antibody were coated in 96 wells and the binding activities of dFcRn were detected by anti-GST HRP.
Figure 10A:
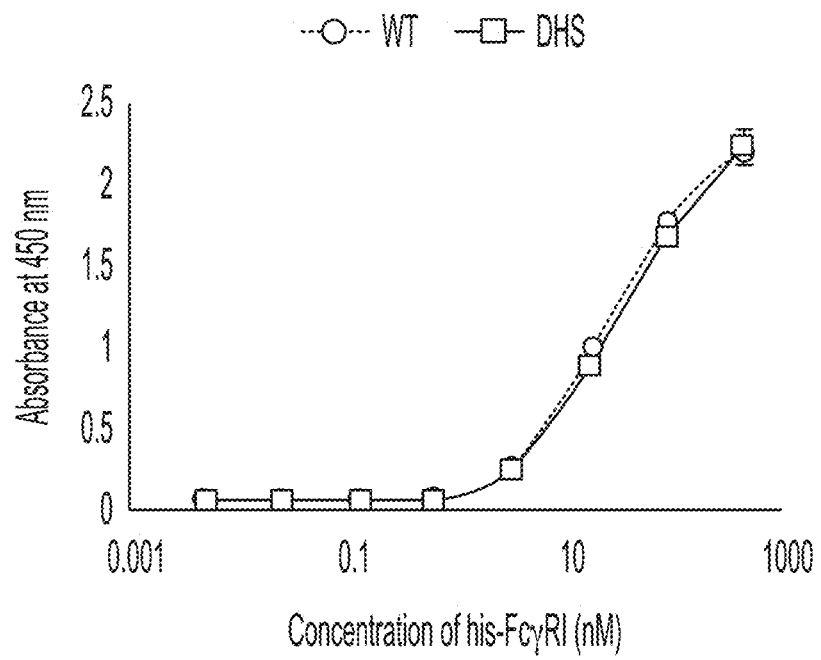
FIGS. 10A-F. ELISA results of wild type Herceptin and the selected IgG variant Herceptin-DHS to FcγRs; monomeric FcγRI (FIG. 10A), dimeric FcγRIIAH131 (FIG. 10B), dimeric FcγRIIA$_{R131}$ (FIG. 10C), dimeric FcγRIIB (FIG. 10D) dimeric FcγRIIIA$_{V157}$ (FIG. 10E), and dimeric FcγRIIIA$_{F157}$ (FIG. 10F).
Figure 10B:
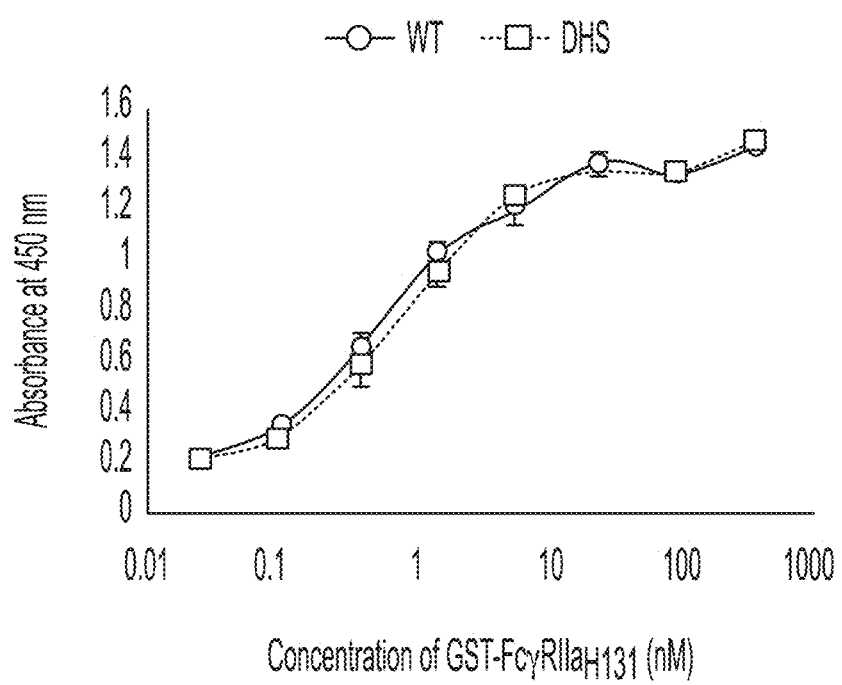
Figure 10C:
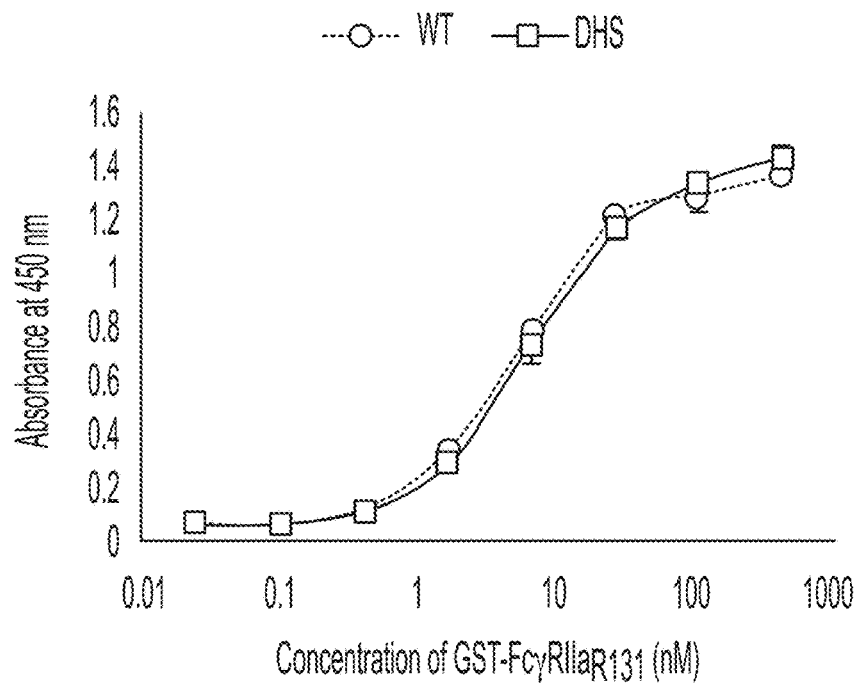
Figure 10D:
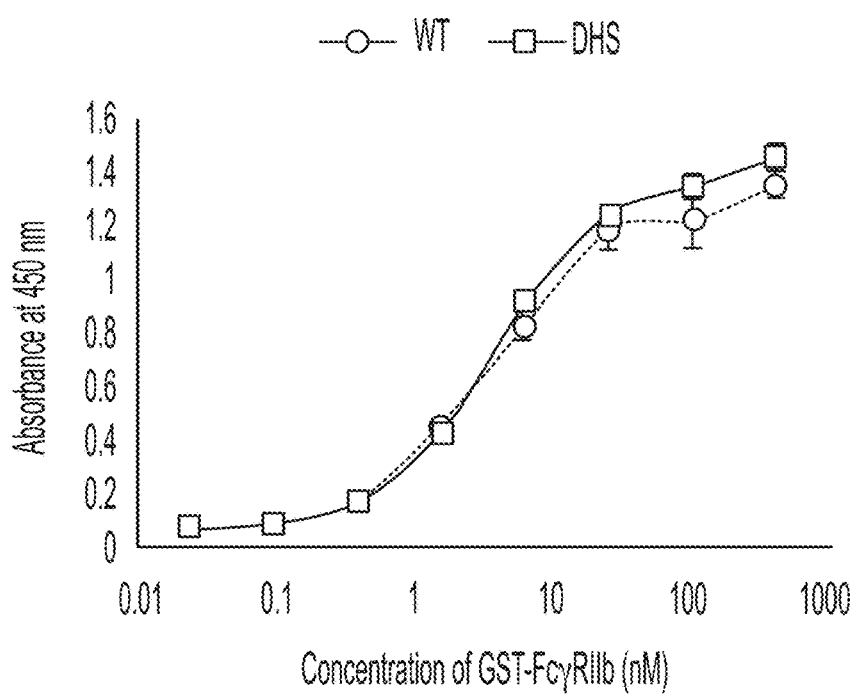
Figure 10E:
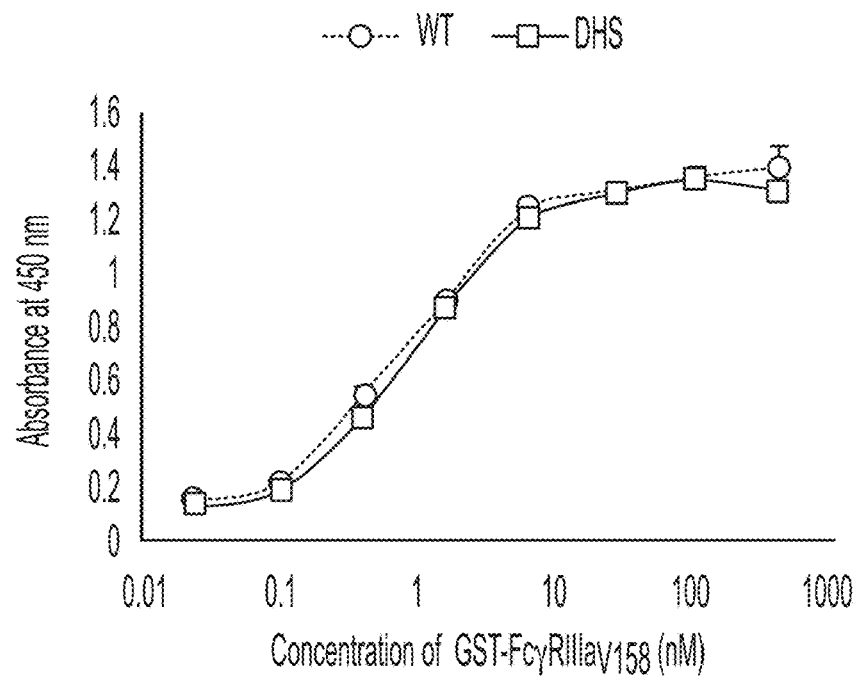
Figure 10F:
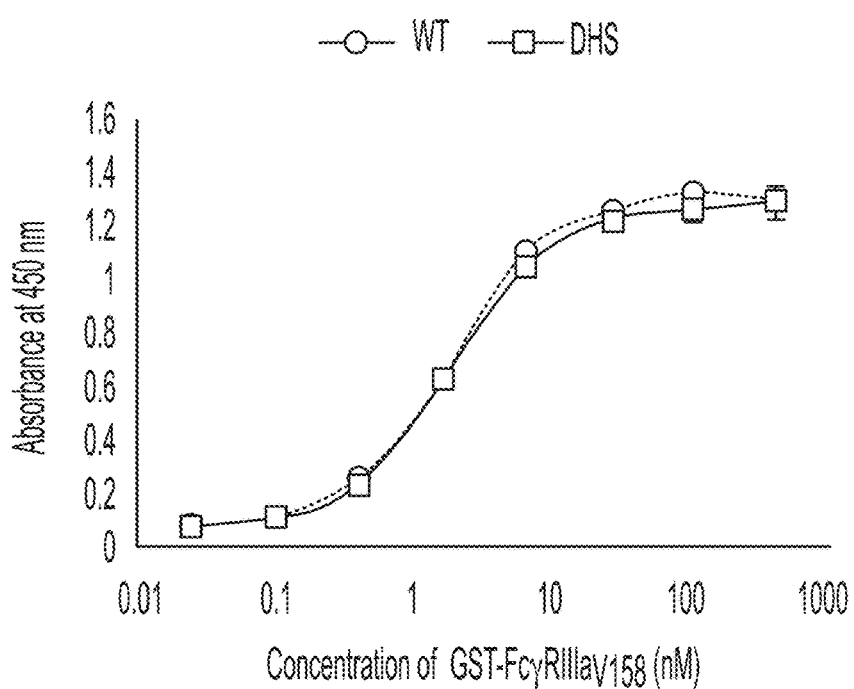
Figure 11A:
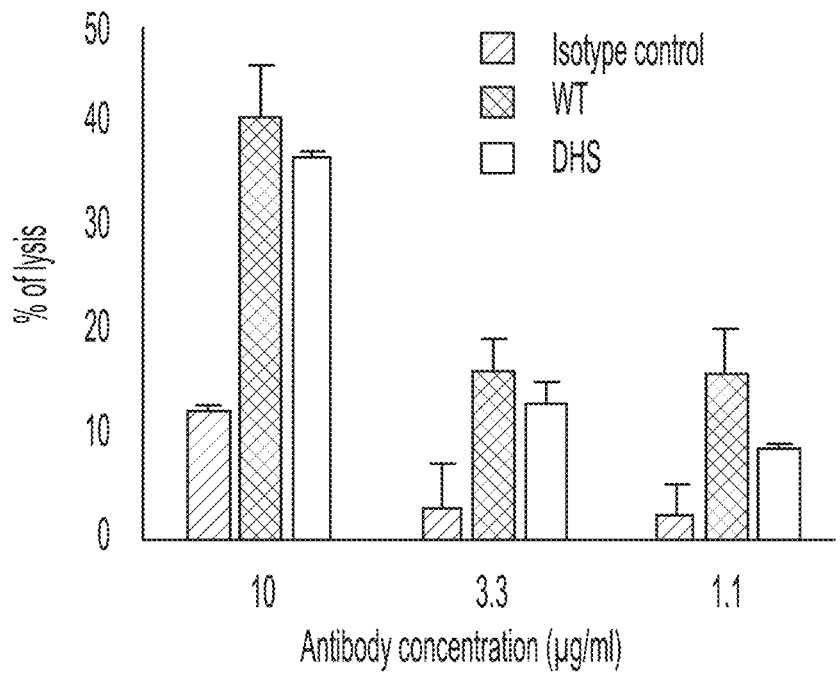
FIGS. 11A-B. Herceptin-DHS mediated ADCC and ADCP assays. Antibodies were incubated with Her2-positive SK-BR3 cells and PBMC or macrophages for each assay.
Figure 11B:
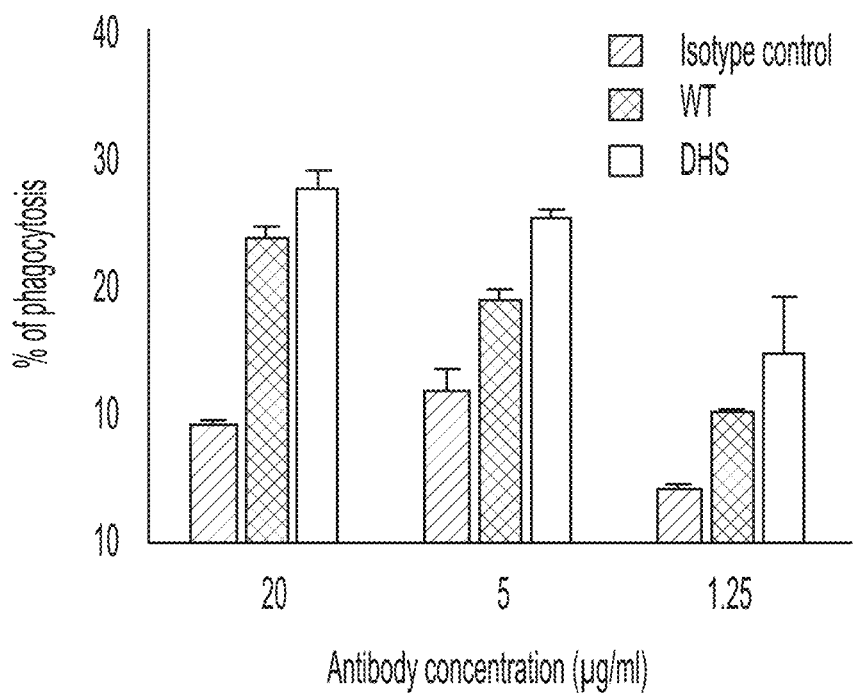

SPR measurements: SPR measurements were performed on Biacore® 3000 (GE Healthcare) instrument. Reference channel of the CM5 sensor chip was closed without immobilization of any proteins to subtract buffer effect and non-specific binding signal. Herceptin-DHS was immobilized on the CM5 sensor chip by amine coupling method at pH 5.0 (Lee et al., 2017). Serially diluted FcRn (400–25 nM) protein was injected onto the CM5 chip at 30 μL/min for 1 min in pH 5.8 PBS. The chip was regenerated after each binding event with 10 mM tris (pH 8.0) with a contact time of 1 min. The resulting sensorgrams were fit with 1:1 Langmuir model using Biaevaluation 3.0 software (FIG. 8). Herceptin-DHS showed similar affinity, 111±20 nM of $K_D$, comparing with Herceptin-EDHS (FIGS. 5 and 8; Table 5). Removal of V264E from Herceptin-EDHS does not affect for FcRn-binding ability.

ELISA measurements of IgG variants with hFcRn: 1 µg of each of Herceptin-DHS was coated onto a 96-well EIA/RIA plate (Qiagen) at 4° C. overnight, and the plate was washed three times with PBST. The plate was blocked for 1 h at room temperature with 1× fish gelatin blocking solution (Biotium) in PBS and washed three times with PBST. Serially diluted dimeric FcRn-β2m-GST (100 nM–0.8125 nM) was then added to the plates. After 1 h of incubation at room temperature, the plates were washed with PBST and then they were incubated with 50 µL of PBS containing 1:5000 goat anti-GST HRP (GE Healthcare) for 1 h. After washing with PBST three times, 50 µL TMB substrate was added per well (Thermo Scientific), 50 µL of 1 M $H_2SO_4$ was added to neutralize, and the absorbance at 450 nm was recorded. Herceptin-DHS did not show any binding activities for dimeric FcRn-β2m-GST at physiological pH 7.4 comparing with wild type Herceptin. As the controls, Herceptin-LS and Herceptin-N434S were tested at same time.

ELISA measurements of IgG variants with hFcγR: The binding properties of EDHS to human FcγRs were assayed as above. Briefly, 1 µg of each of wild type Herceptin or Herceptin-EDHS was coated onto a 96-well EIA/RIA plate (Qiagen) at 4° Covernight, and the plates were washed three times with PB ST. The plates were blocked for 1 h at room temperature with 1% BSA in PBS and washed three times with PBST. The serially diluted monomeric His-FcγRI, dimeric GST-FcγRIIa$_{R131}$, dimeric GST-FcγRIIa$_{H131}$, dimeric GST-FcγRIIb, dimeric GST-FcγRIIIa$_{V158}$, and dimeric GST-FcγRIIIa$_{F158}$ were then added to the plates. After 1 h of incubation at room temperature, the plates were washed with PBST and were incubated with 50 µL of PBS containing 1:5000 goat anti-His or anti-GST HRP (GE Healthcare) for 1 h. After three times of washing with PBST, 50 µL TMB substrate was added per well (Thermo Scientific), 50 µL of 1 M $H_2SO_4$ was added to neutralize, and the absorbance at 450 nm was recorded. The Herceptin-DHS showed same binding profiles comparing with wild type Herceptin for all FcγRs (FIGS. 10A-F).

Figure 18:
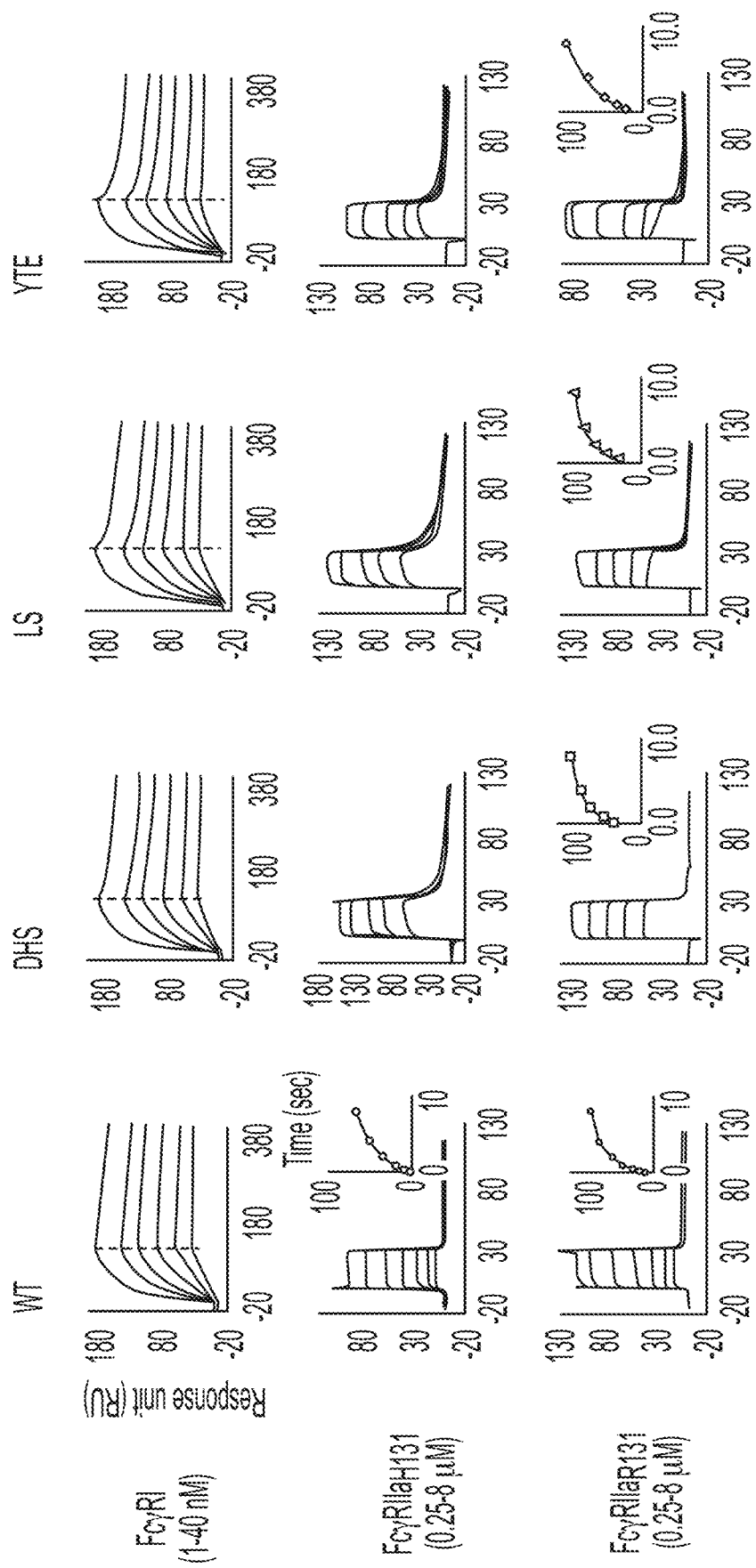
FIG. 18. SPR analysis of antibody variants. Each antibody was immobilized onto a CM5 chip, and the serially diluted FcγRs or C1q were injected at 30 µl/min. All experiments were repeated three times independently, and the kinetic values of each antibody are presented in Table 12.
Figure 18:
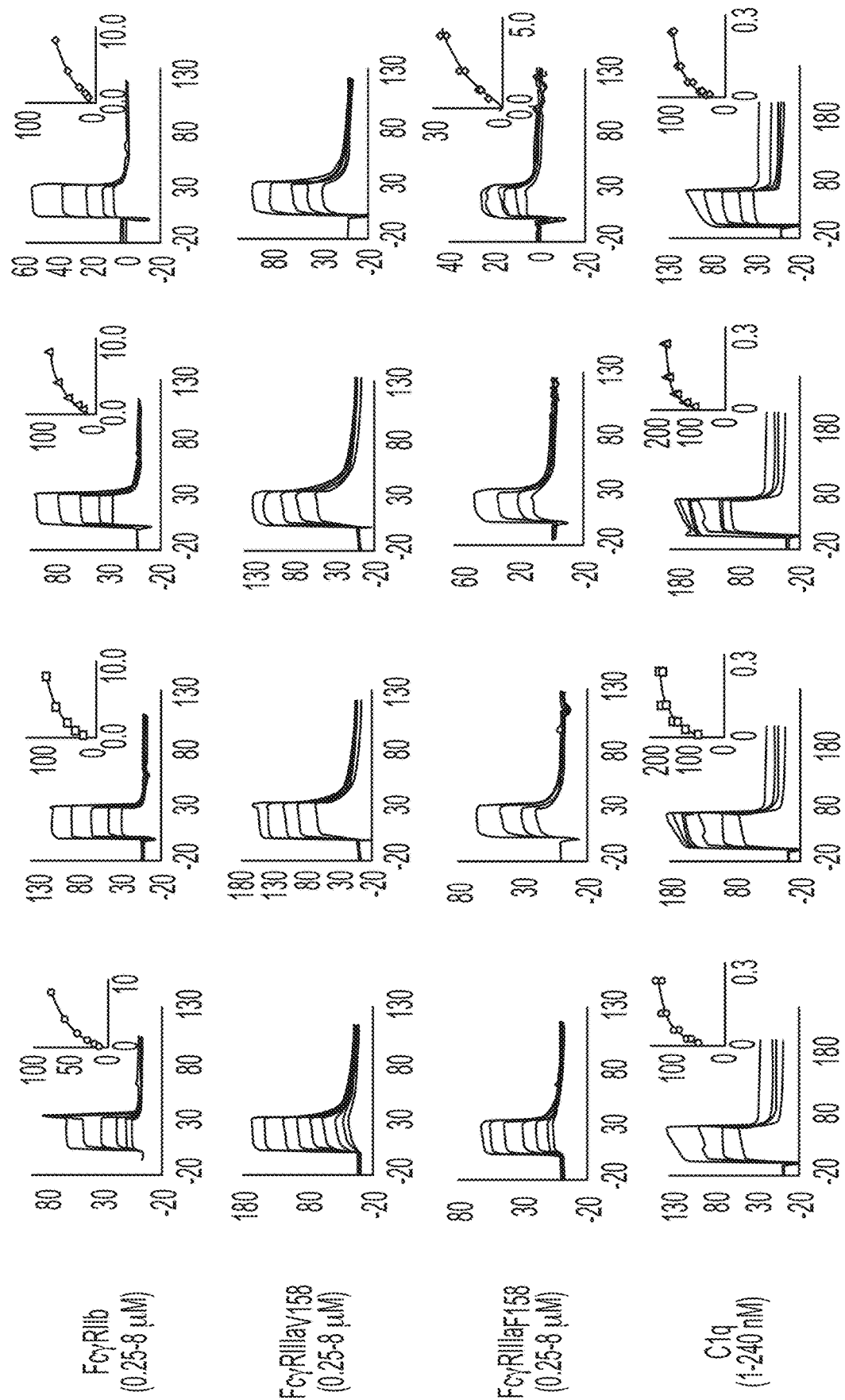

SPR measurements: SPR measurements were performed on Biacore® 3000 (GE Healthcare) instrument. Reference channel of the CM5 sensor chip was closed without immobilization of any proteins to subtract buffer effect and non-specific binding signal. Wild type Herceptin, Herceptin-DHS, Herceptin-LS, and Herceptin-YTE were immobilized on the CM5 sensor chips by amine coupling method at pH 5.0. The serially diluted FcγRs or C1q (400–25 nM) protein was injected onto the CM5 chip at 30 µL/min for 1 min in pH 7.4 HBS-EP. The chip was regenerated after each binding event with 10 mM glycine (pH 5.0) with a contact time of 1 min. The resulting sensorgrams were fit with 1:1 Langmuir model or euivalent binding model using Biaevaluation 3.0 software (FIG. 18 and Table 12). The results of kinetic analysis for Fc receptors were consistent with ELISA results. Herceptin-DHS showed equivalent kinetic values for FcγRs and C1q comparing with wild type Herceptin but Herceptin-LS and Herceptin-YTE significantly lost FcγRs binding ability, especially FcγRIIIa which is key receptor for ADCC (FIG. 18 and Table 12).

In conclusion, removal of V264E does not affect pH-dependent FcRn binding ability of Herceptin-EDHS for FcRn but recovers the binding capability for FcγR.

TABLE 12

Kinetic values of IgG variants for Fc receptors

| | | $k_a$ ($10^5$/Ms) | $k_d$ ($10^{-2}$/s) | $K_D$ (µM) | Fold* |
|---|---|---|---|---|---|
| WT | FcRn/β2m | 5.4 ± 0.3 | 29.0 ± 0.8 | 0.55 ± 0.05 | |
| | FcγRI | 21.7 ± 2.6 | 0.045 ± 0.003 | 0.21 ± 0.02 nM | |
| | FcγRIIa$_{H131}$ | — | — | 0.22 ± 0.06 | |
| | FcγRIIa$_{H131}$ | — | — | 1.16 ± 0.25 | |
| | FcγRIIb | — | — | 2.64 ± 0.39 | |
| | FcγRIIIa$_{F158}$ | 0.85 ± 0.09 | 9.95 ± 0.49 | 1.17 ± 0.23 | |
| | FcγRIIIa$_{V158}$ | 1.98 ± 0.49 | 3.55 ± 0.61 | 0.17 ± 0.04 | |
| | C1q | — | — | 0.042 ± 0.005 | |
| DHS | FcRn/β2m | 7.8 ± 0.2 | 8.7 ± 0.1 | 0.11 ± 0.02 | 5.0 |
| | FcγRI | 18.7 ± 1.5 | 0.052 ± 0.004 | 0.28 ± 0.02 nM | 0.8 |
| | FcγRIIa$_{H131}$ | 1.59 ± 0.20 | 4.02 ± 0.27 | 0.27 ± 0.04 | 0.8 |
| | FcγRIIa$_{R131}$ | — | — | 0.95 ± 0.02 | 1.2 |
| | FcγRIIb | — | — | 2.91 ± 0.54 | 0.9 |
| | FcγRIIIa$_{F158}$ | 2.07 ± 0.29 | 9.39 ± 0.20 | 0.48 ± 0.07 | 2.4 |
| | FcγRIIIa$_{V158}$ | 2.10 ± 0.19 | 3.59 ± 0.23 | 0.18 ± 0.03 | 0.9 |
| | C1q | — | — | 0.025 ± 0.002 | 1.7 |
| LS | FcRn/β2m | 6.2 ± 1.6 | 3.3 ± 0.1 | 0.055 ± 0003 | 10.0 |
| | FcγRI | 15.3 ± 4.2 | 0.039 ± 0.011 | 0.58 ± 0.12 nM | 0.4 |
| | FcγRIIa$_{H131}$ | 0.91 ± 0.07 | 3.67 ± 0.09 | 0.41 ± 0.30 | 0.5 |
| | FcγRIIa$_{R131}$ | — | — | 1.21 ± 0.02 | 1.0 |
| | FcγRIIb | — | — | 2.25 ± 0.03 | 1.2 |
| | FcγRIIIa$_{F158}$ | 1.34 ± 0.17 | 8.16 ± 0.62 | 0.64 ± 0.09 | 1.8 |
| | FcγRIIIa$_{V158}$ | 1.01 ± 0.15 | 4.96 ± 0.14 | 0.52 ± 0.09 | 0.3 |
| | C1q | — | — | 0.016 ± 0.001 | 2.6 |
| YTE | FcRn/β2m | 8.2 ± 1.4 | 2.3 ± 0.1 | 0.023 ± 0.001 | 23.9 |
| | FcγRI | 19.3 ± 1.0 | 0.055 ± 0.005 | 0.29 ± 0.02 nM | 0.7 |
| | FcγRIIa$_{H131}$ | 1.28 ± 0.28 | 6.54 ± 0.07 | 0.62 ± 0.18 | 0.4 |
| | FcγRIIa$_{R131}$ | — | — | 3.20 ± 0.26 | 0.4 |
| | FcγRIIb | — | — | 6.24 ± 0.10 | 0.4 |
| | FcγRIIIa$_{F158}$ | — | — | 4.41 ± 0.93 | 0.3 |
| | FcγRIIIa$_{V158}$ | 1.06 ± 0.22 | 8.03 ± 0.66 | 0.82 ± 0.11 | 0.2 |
| | C1q | — | — | 0.042 ± 0.08 | 1.0 |

Example 9

Effector Functions of Herceptin-DHS

ADCC assay: Human peripheral blood mononuclear cell (PBMC) was isolated from human blood from healthy donor on the day prior to the ADCC assay. 50 mL of human blood was collected in heparinised vials (BD biosciences) and mixed well by gently inverting the tube several times. 25 mL of blood was layered over 25 mL of room temperature Ficoll Histopaque (Invitrogen) in a 50 mL conical tube. The tubes were centrifuged at 2,500 rpm for 30 min in a swing-bucket rotor without brakes. The human PBMCs were aspirated in the interphase between histopaque and medium. Human PBMC was resuspended with red blood cell (RBC) lysis buffer (155 mM $NH_4Cl$, 12 mM $NaHCO_3$, and 0.1 mM EDTA), and washed twice with PBS. The isolated human PBMCs were mixed with calcein AM-labeled SK-BR3 Her2-positive cancer cells and various concentrations of IgG variants in 96-well plates. The ratio of tumor versus effector cell was 1:10 and the plates incubated at 37° C. with 5% $CO_2$ for 4 h. The percent of tumor cell lysis was calculated according to the following formula: 100×(E–S)/(M–S), where E is the fluorescence of the experimental well, S is that in the absence of antibody (tumor cells were incubated with medium and effector cells), and M is that of tumor cells with lysis buffer. As described in Example 8, Herceptin-DHS showed equivalent ADCC activities with PBMC comparing with Herceptin because Herceptin-DHS has the same affinities for FcγRs (FIGS. 10A-F and 11A) comparing with Herceptin.

ADCP assay: CD14-positive monocytes were purified from PBMC using CD14 MicroBead Kit (Miltenyi Biotec). And then, monocytes were differentiated into macrophages by culture for 7 days in RPMI medium containing 15% FBS and 50 ng/ml GM-CSF before combination at a 10:1 effector:tumor cell ratio with Calcein-labeled SK-BR3 cells. For ADCP assays, SK-BR3 cells were incubated with various concentrations of antibodies and macrophages. After 2 hr at 37° C., the cells were labeled with anti-CD11b-APC and anti-CD14-APC. Phagocytosis was evaluated by FACS on an LSRFortessa (BD Bioscience), and reported as the fraction of double positive cells over the total number of tumor cells in the sample. Herceptin-DHS showed equivalent ADCC activities with PBMC comparing with Herceptin because Herceptin-DHS has the same affinities for FcγRs (FIGS. 10A-F and 11B) comparing with Herceptin.

Example 10

Binding Properties of the Herceptin-DHS to FcRn

In order to examine the detailed pH-dependent binding activities of Herceptin-DHS, antibodies were evaluated with three different densities of scFcRn or different pH conditions by SPR.

Figure 12:
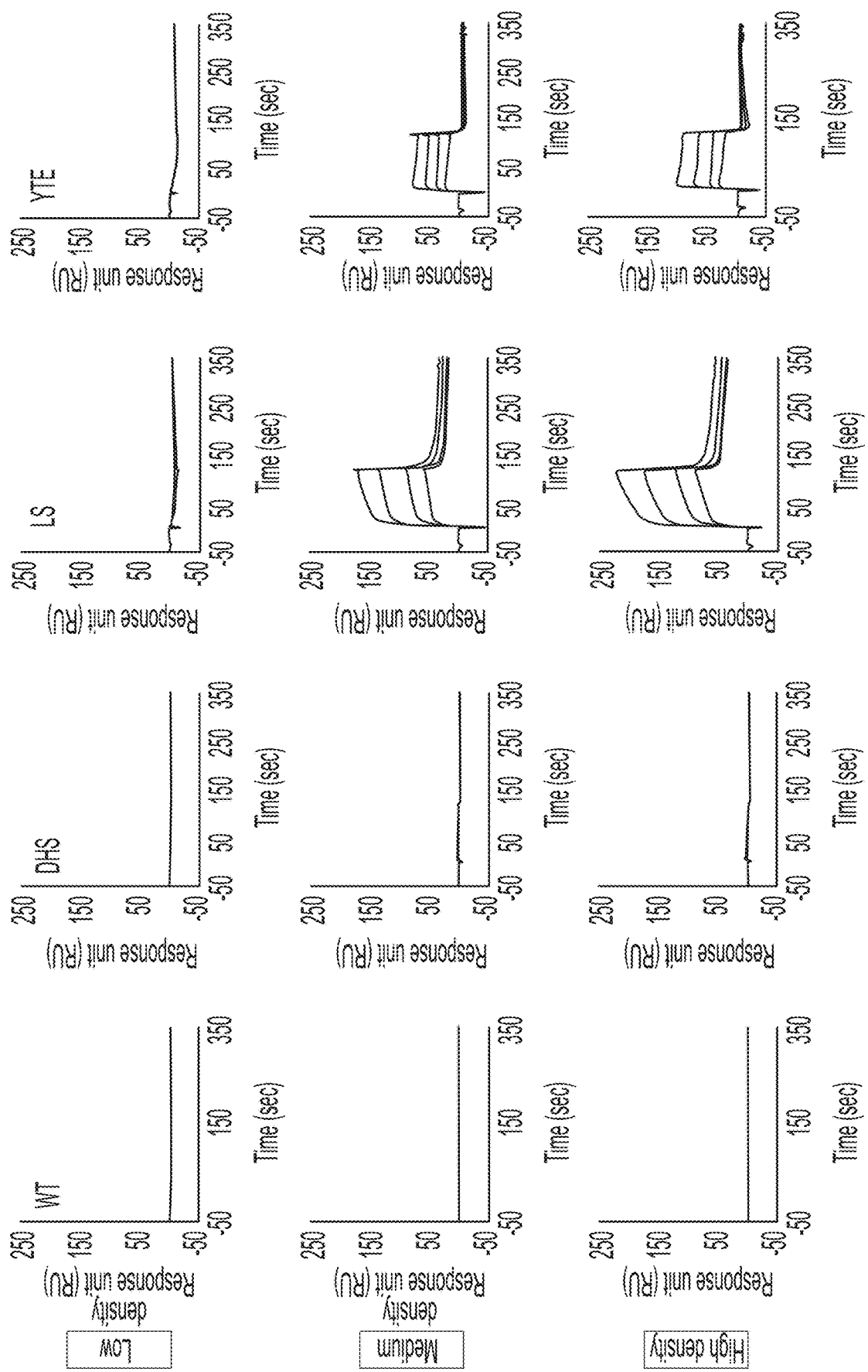
FIG. 12. Surface plasmon resonance (SPR) sensorgrams of Herceptin, Herceptin-DHS, Herceptin-LS, and Herceptin-YTE with three different densities of scFcRn. scFcRn was immobilized on CM5 chip with three different levels, 500 RU, 2000 RU, and 4000 RU, and the serially diluted antibody proteins in pH 7.4 PBS were injected into CM5 chip.

SPR measurements: SPR measurements were performed on Biacore® 3000 (GE Healthcare) instrument. Reference channel of the CM5 sensor chip was closed without immobilization of any proteins to subtract buffer effect and non-specific binding signal. scFcRn was immobilized with three different immobilization levels (500 RU, 2000 RU, and 4000 RU) on the CM5 sensor chips by amine coupling method at pH 5.0. The serially diluted antibody (400–25 nM) protein was injected onto the CM5 chip at 30 µL/min for 1 min in pH 7.4 PBS. The chip was regenerated after each binding event with 10 mM tris (pH 8.0) with a contact time of 1 min. The resulting sensorgrams were fit with 1:1 Langmuir model using Biaevaluation 3.0 software (FIG. 12 and Table 6). Herceptin-DHS and wild type Herceptin did not show any binding signals with low, medium and high density of scFcRn. Herceptin-LS and Herceptin-YTE did not show any binding signals with low density of scFcRn but showed significant binding onto scFcRn immobilized at w medium and high densities (Table 6). The $K_D$ of Herceptin-LS is 58.7 nM with medium density of FcRn and 22.7 nM with high density of FcRn. The $K_D$ of Herceptin-YTE is 4.73 µM with medium density of FcRn and 4.29 µM with high density of FcRn.

TABLE 6

$K_D$ values of the isolated Fc variant for FcRn at pH 7.4

| FcRn density | Wild type Herceptin | Herceptin-DHS | Herceptin-LS | Herceptin-YTE |
|---|---|---|---|---|
| Low | — | — | — | — |
| Medium | — | — | 58.7 nM | 4.73 µM |
| High | — | — | 22.7 nM | 4.29 µM |

Figure 13A:
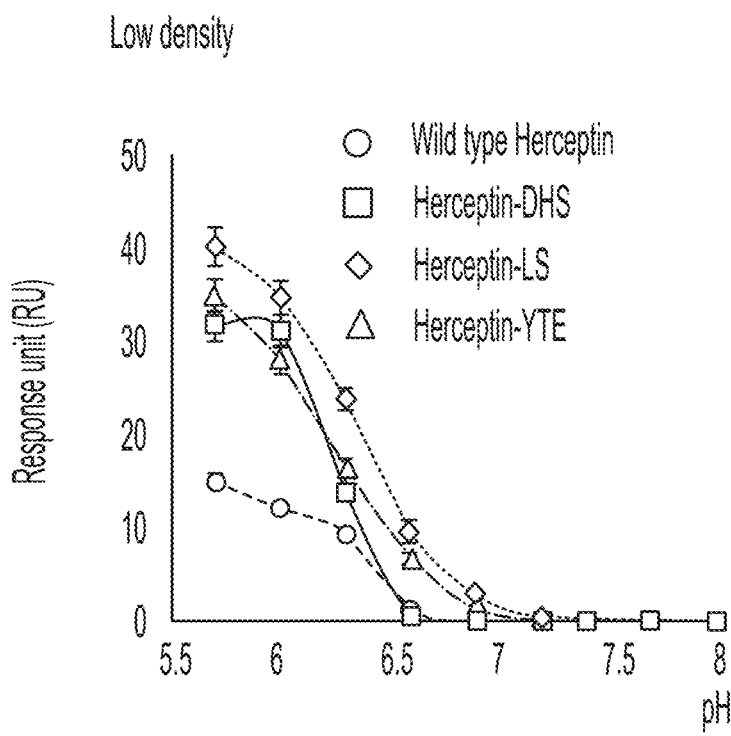
FIGS. 13A-C. Surface plasmon resonance (SPR) sensorgrams of Herceptin, Herceptin-DHS, Herceptin-LS, and Herceptin-YTE with three different densities of scFcRn. scFcRn was immobilized on CM5 chip with three different levels, 500 RU, 2000 RU, and 4000 RU, and the 1 µM of antibody proteins with diverse pH were injected into CM5 chip.
Figure 13B:
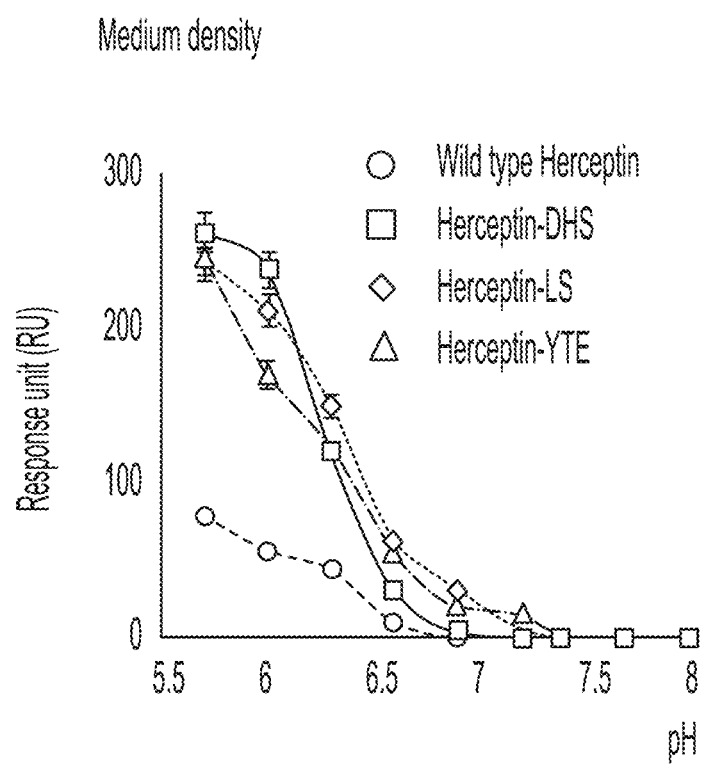
Figure 13C:
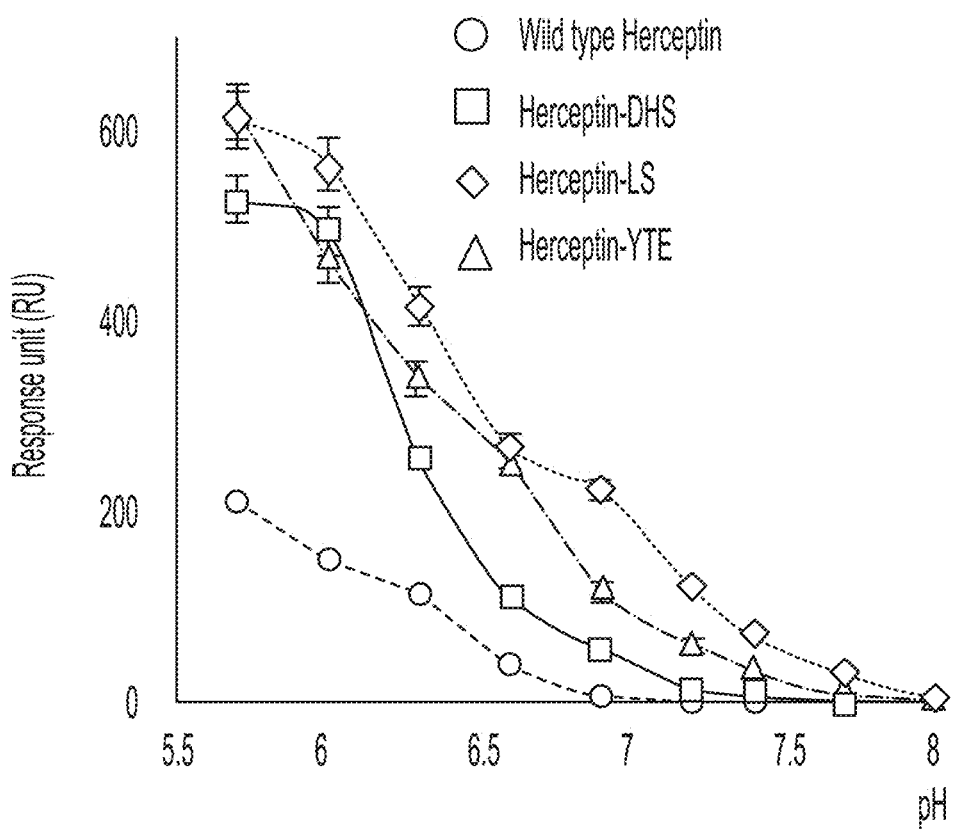

Next, to examine the detailed pH-dependent binding activities of antibodies, antibodies were assayed with diverse pH conditions. 1 µM of wild type Herceptin, Herceptin-DHS, Herceptin-LS, and Herceptin-YTE was injected onto CM5 chip at 30 µL/min for 1 min in pH 4.5-8.5 PBS. The chip was regenerated after each binding event with 10 mM tris (pH 8.0) with a contact time of 1 min. As shown in FIGS. 13A-C, Herceptin-DHS showed better binding activities than wild type Herceptin but Herceptin-DHS lost significantly FcRn-binding activities at from pH 6.2 to pH 6.5 under the conditions of three different FcRn-densities. And Herceptin-DHS completely lost FcRn-binding activities at pH 6.8.

Example 11

Pharmacokinetics of Herceptin-DHS in Human FcRn Transgenic Mice

Figure 14:
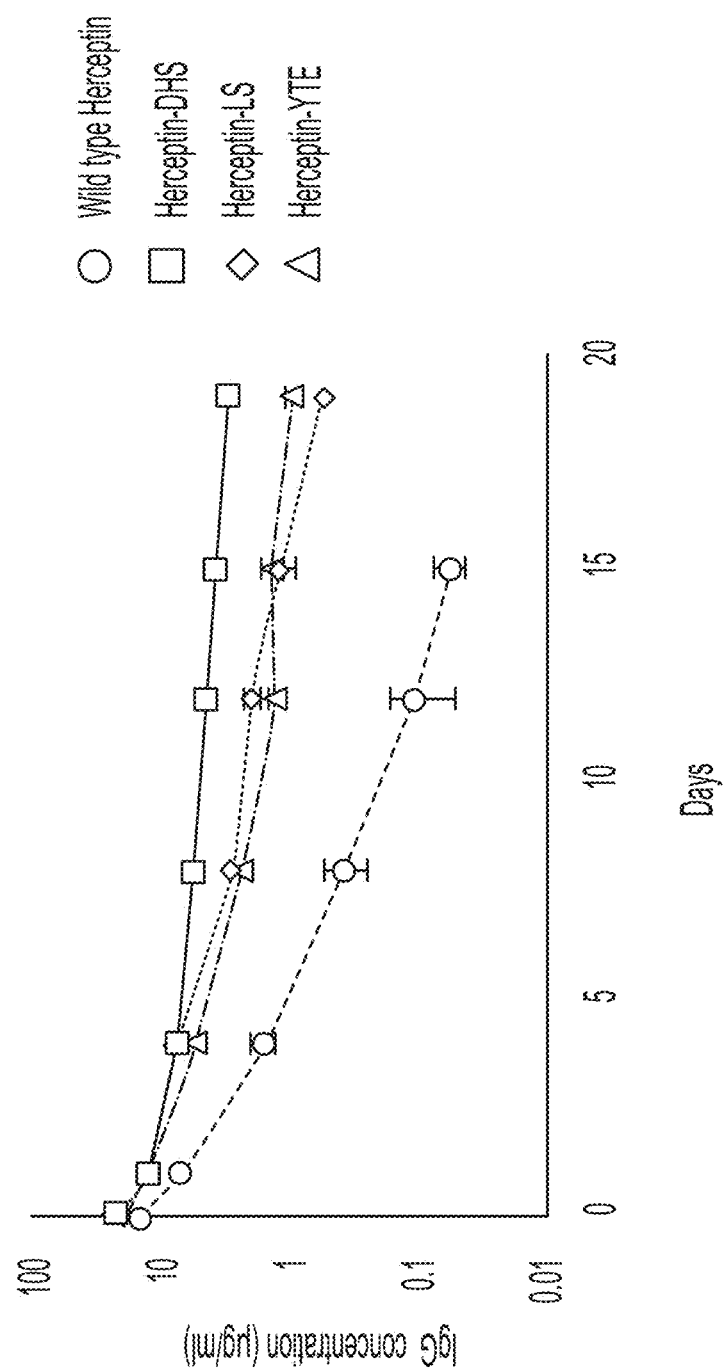
FIG. 14. Pharmacokinetics of antibodies in human FcRn transgenic mice.
Figure 15A:
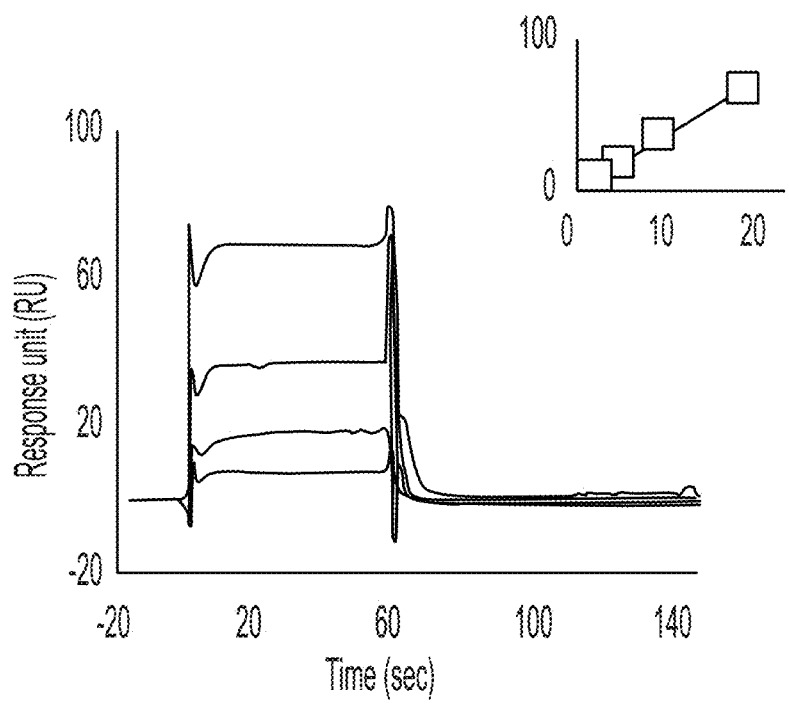
FIGS. 15A-F. Surface plasmon resonance (SPR) assays of IgG2 (FIG. 15A), IgG2-DHS (FIG. 15B), IgG3 (FIG. 15C), IgG3-DHS (FIG. 15D), IgG4 (FIG. 15E) and IgG4-DHS (FIG. 15F) for scFcRn.
Figure 15B:
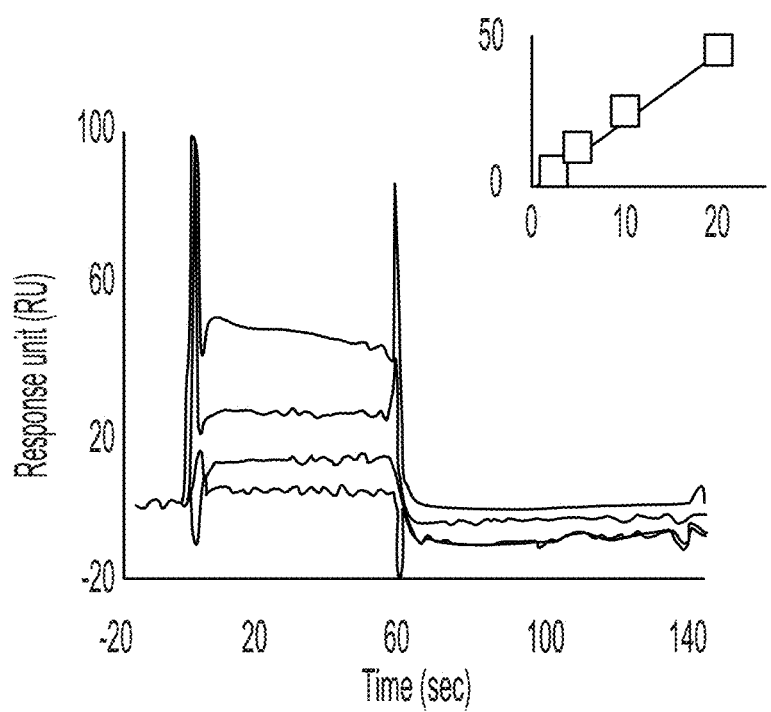
Figure 15C:
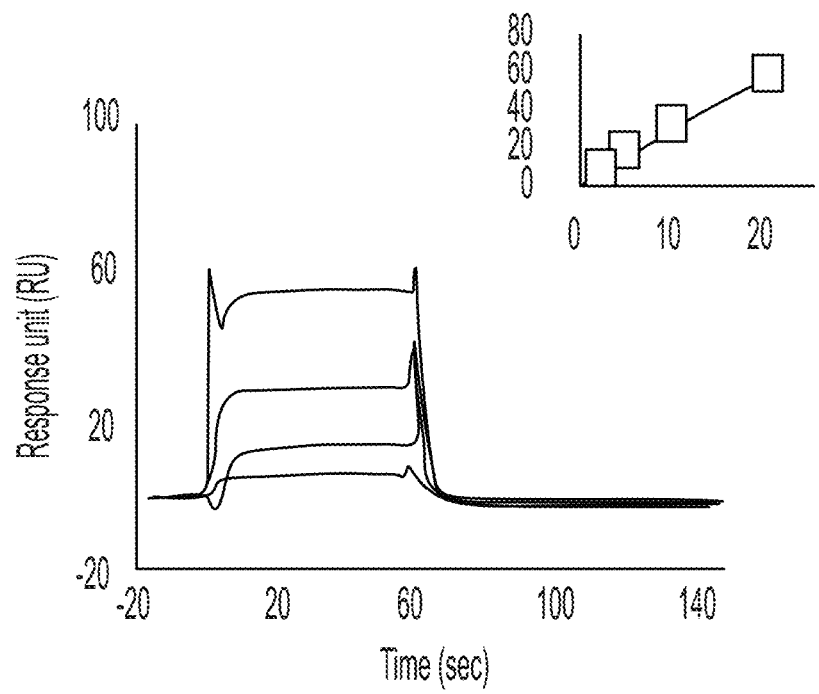
Figure 15D:
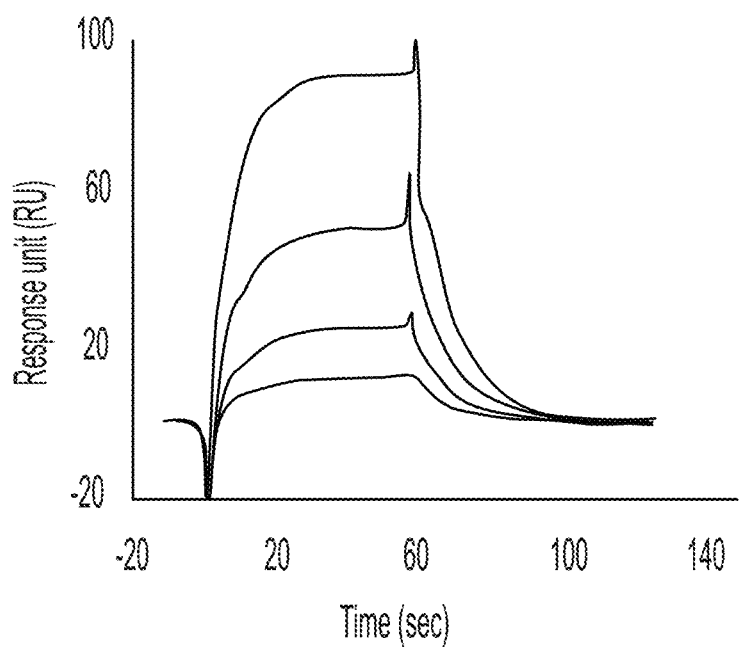
Figure 15E:
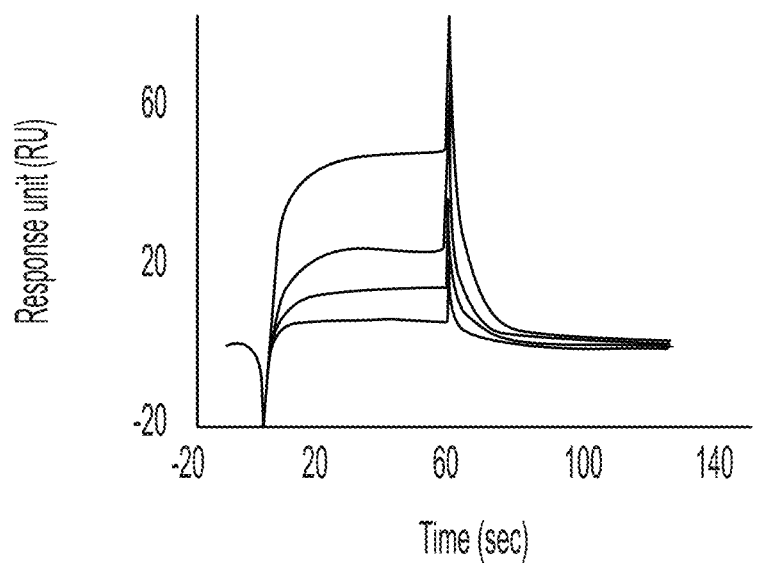
Figure 15F:
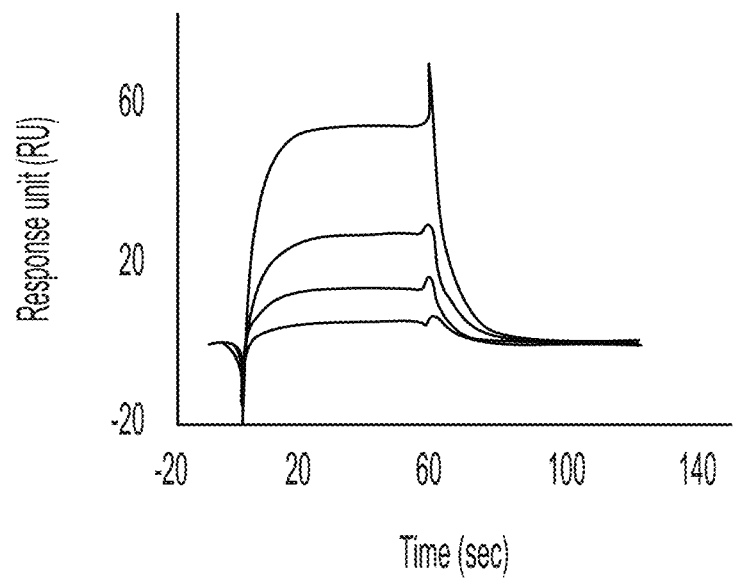

Pharamokinetics of the modified IgGs were performed in hemizygous hFcRn transgenic mice (line 276) produced by the F1 cross of murine FcRn deficient B6.129X1-Fcgrttm1Dcr/DcrJ and hFcRn cDNA transgenic line B6.Cg-Fcgrttm1Dcr Tg (CAG-FCGRT) 276 Dcr/DcrJ (Roopenian et al., 2003 and Chaudhury et al., 2003). hFcRn mice were given a bolus intravenous (IV) dose of 2 mg/kg antibody on day 0. Eleven mice were used per antibody. Blood samples were obtained from the tail vein using capillary pipettes at different time points throughout the 2-3 weeks studies. A quantitative ELISA was used to monitor the serum concentrations of the tested antibodies. Briefly, 96-well plates were coated with 2m/ml of Goat anti-human F(ab')2 fragment-specific F(ab')2 (Jackson Immunoresearch). Plates were blocked with 1% Fish gelatin (AMRESCO-inc) in PBS for an hour, and then incubated with appropriately diluted serum samples (1:200 for earlier time points and 1:50 or 1:100 for later time points). Anti-Kappa light chain antibody-HRP (Abcam) was used to detect the human antibody (dilution 1:5,000). Absorbance at 450 nm was measured after development with TMB substrate (Pierce Biotechnology, Rockford, Ill.) according to manufacturer's directions. Standard curves were generated for each antibody variant diluted into 1:100 pre-bleed mouse serum. The linear portions of standard curves generated in Prism (GraphPad Software) were then used to quantify human IgG in the serum samples. AUCinf (Area under the curve to infinity) was calculated using the log-linear trapezoidal method. Terminal half-life (T1/2) was calculated using log-linear regression of the concentration data including at least the last three sampling time-points with measurable concentrations. Serum clearance was estimated as: CL=Dose/AUCinf. Descriptive statistics for major PK parameters were then calculated. As results, Herceptin-DHS showed 6.8-fold increased beta phase serum half-life (β phase $T_{1/2}$=336±24.8 hours) than wild type Herceptin (FIG. 14 and Table 7). Herceptin-DHS also showed 9.5-fold slow clearance rate (0.061±0.003 ml/day/kg), 7.9-fold enhanced AUCinf (326.6±17.9 µg*days/ml), and 3.96-fold lower tissue distribution (0.28±0.01 ml/kg) than wild type Herceptin.

TABLE 7

Pharmacokinetic values of the isolated Fc variant

| | Clearance (ml/days/kg) | β phase $T_{1/2}$ (hrs) | $AUC_{inf.}$ (µg * days/ml) | Vss (ml/kg) |
|---|---|---|---|---|
| Wild-type Herceptin | 0.58 ± 0.17 | 49.3 ± 4.4 | 41.2 ± 23.6 | 1.11 ± 0.15 |
| Herceptin-DHS | 0.061 ± 0.003 | 336 ± 24.8 | 326.6 ± 17.9 | 0.28 ± 0.01 |
| Herceptin-LS | 0.099 ± 0.004 | 107 ± 7.2 | 200.7 ± 9.4 | 0.34 ± 0.01 |
| Herceptin-YTE | 0.111 ± 0.028 | 204.3 ± 8.7 | 178.7 ± 12.5 | 0.42 ± 0.01 |

Example 12

DHS Mutations in IgG-Subclasses

IgG has four subclass members, IgG1, IgG2, IgG3, and IgG4. The FcRn binding sites in IgG subclasses are highly conserved such that IgG2 and IgG4 display serum half-life comparable to that of IgG1. There are two single nucleotide polymorphisms at the $435^{th}$ residue of IgG: IgG3-R435 has shorter serum half-life (~8 days) but IgG3-H435 has similar half-life compared with other IgG subclasses (~21 days). To examine whether the DHS mutation (L309D, Q311H, and N434S) mutations are capable of enhancing FcRn-binding activity in other IgG subclasses, the DHS mutations were introduced into heavy chain genes of IgG2, IgG3-H435, and IgG4. Fc genes for IgG2-DHS, IgG3-DHS, and IgG4-DHS were synthesized by IDT and Fc genes were cloned into pcDNA3.4 using a Gibson Assembly® cloning kit (NEB) according to the manufacturer's instructions (Lee et al., 2017). The Gibson assembled mixtures were transformed into E. coli JUDE-1 cells and their sequences confirmed. And the Fab of trastuzumab was used. The heavy chain genes of four trastuzumab-Fc variants were transiently transfected with an equal mass of light chain plasmid in HEK293F cells (Invitrogen). After incubation in a 5% $CO_2$ incubator at 37° C. for six days, the supernatants were collected by centrifugation at 4,000×g for 10 min and filtered using a 0.22 μm PES membrane filter (PALL). The filtered supernatants were passed over Protein A high capacity agarose resin (Thermo Scientific) three times. To remove LPS and non-specifically bound protein, the IgG-bound resins were washed with 50 mL PBS containing 0.1% Triton® X-114 (Sigma-Aldrich) and 50 mL PBS. All IgG variants were eluted with 100 mM glycine buffer (pH 3.0) and immediately neutralized with 1M Tris-HCl buffer (pH 8.0). The buffer of all eluted trastuzumab-Fc antibody variants was exchanged to PBS by Amicon® Ultra-4 (Millipore). The purity of reduced or non-reduced proteins for the trastuzumab-Fc antibody variants and for authentic (w.t.) trastuzumab expressed in HEK293 cells as above were assessed by 4%-20% gradient SDS-PAGE gel (NuSep) under reducing and non-reducing conditions.

SPR measurements: SPR measurements were performed on Biacore® 3000 (GE Healthcare) instrument. Reference channel of the CM5 sensor chip was closed without immobilization of any proteins to subtract buffer effect and non-specific binding signal. Wild type IgG2, wild type IgG3, wild type IgG4, IgG2-DHS, IgG3-DHS and IgG4-DHS were immobilized on the CM5 sensor chips by amine coupling method at pH 5.0. The serially diluted FcRn (400–25 nM) protein was injected onto the CM5 chip at 30 μL/min for 1 min in pH 5.8 PBS. The chip was regenerated after each binding event with 10 mM tris (pH 8.0) with a contact time of 1 min. The resulting sensorgrams were fit with 1:1 Langmuir model using Biaevaluation 3.0 software (FIGS. 15). IgG2-DHS showed 5.7-fold enhanced $K_D$ (377±26 nM) for scFcRn comparing with wild type IgG2 (FIGS. 15A-B; Table 8). IgG3-DHS showed 5.5-fold enhanced $K_D$ (739±75 nM) for scFcRn comparing with wild type IgG3 (FIGS. 15C-D; Table 8). IgG4-DHS showed 3.0-fold enhanced $K_D$ (832±16 nM) for scFcRn comparing with wild type IgG4 (FIGS. 15E-F; Table 8).

TABLE 8

Kinetic values of DHS-Fc variant for FcRn at pH 5.8

| | $K_{on}$ ($10^5 M^{-1} sec^{-1}$) | $K_{off}$ ($10^{-2} sec^{-1}$) | $K_D$ (nM) |
|---|---|---|---|
| Herceptin-IgG2 | | | 2140 ± 380 |
| Herceptin-IgG2-DHS | 2.27 ± 0.13 | 8.6 ± 0.1 | 377 ± 26 |
| Herceptin-IgG3 | | | 4080 ± 790 |
| Herceptin-IgG3-DHS | 1.7 ± 0.13 | 12.6 ± 0.3 | 739 ± 75 |
| Herceptin-IgG4 | | | 2460 ± 165 |
| Herceptin-IgG4-DHS | 2.81 ± 0.10 | 15.1 ± 0.2 | 832 ± 16 |

Figure 16A:
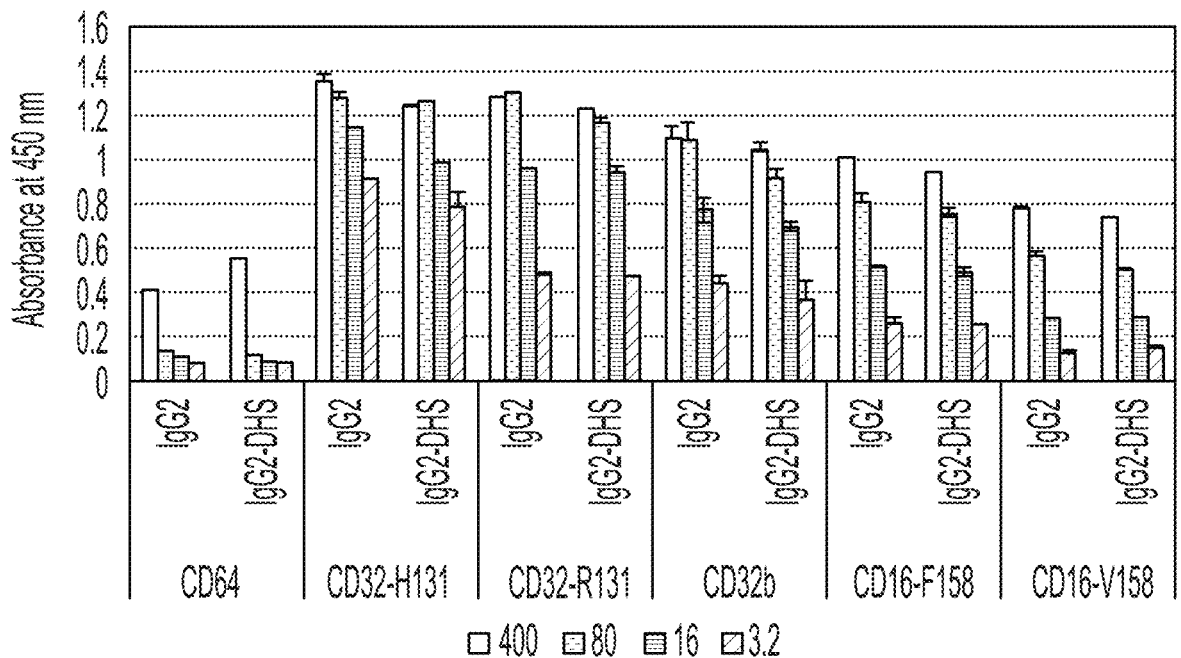
Figure 16B:
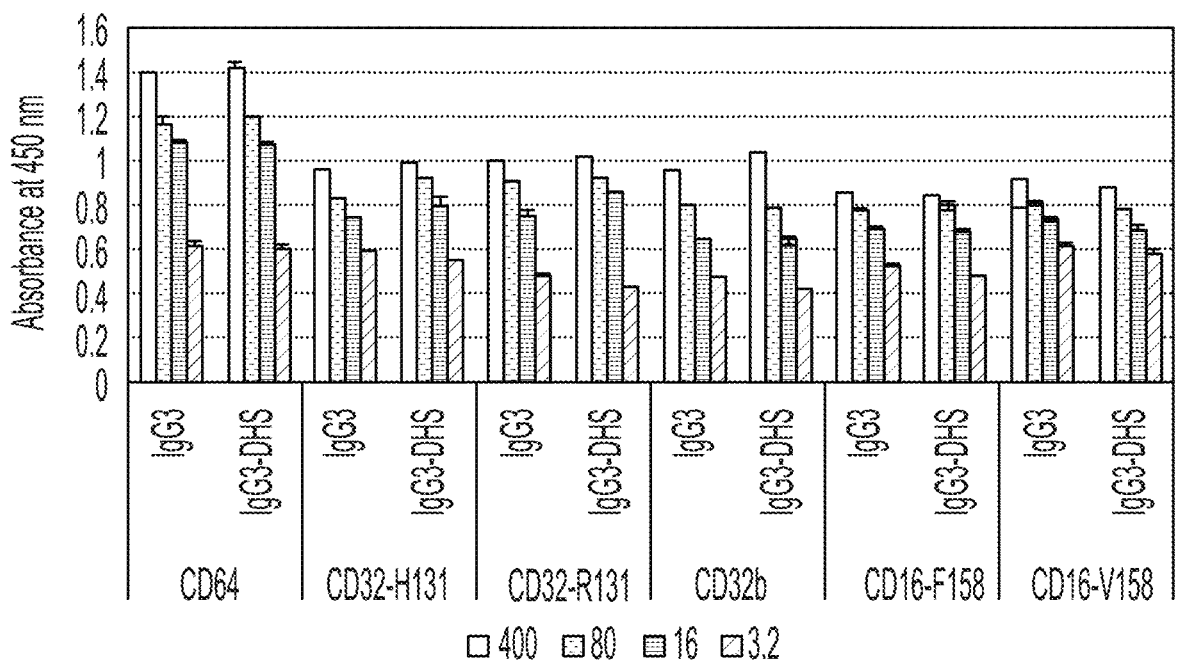

ELISA measurements of IgG variants with hFcγR: The binding properties of EDHS to human FcγRs were assayed. The detailed procedures were same with above paragraph. Briefly, 1 μg of each of wild type IgG2, IgG2-DHS, wild type IgG3, IgG3-DHS, wild type IgG4, and IgG4-DHS was coated onto a 96-well EIA/RIA plate (Qiagen) at 4° C. overnight, and the plates were washed three times with PBST. The plates were blocked for 1 h at room temperature with 1% BSA in PBS and washed three times with PBST. The serially diluted monomeric His-FcγRI, dimeric GST-FcγRIIa$_{R131}$, dimeric GST-FcγRIIa$_{H131}$, dimeric GST-FcγRIIb, dimeric GST-FcγRIIIa$_{V158}$, and dimeric GST-FcγRIIIa$_{F158}$ were then added to the plates. After 1 h of incubation at room temperature, the plates were washed with PBST and were incubated with 50 μL of PBS containing 1:5000 goat anti-His or anti-GST HRP (GE Healthcare) for 1 h. After three times of washing with PBST, 50 μL TMB substrate was added per well (Thermo Scientific), 50 μL of 1 M $H_2SO_4$ was added to neutralize, and the absorbance at 450 nm was recorded. The IgG2-DHS showed same binding activities comparing with wild type IgG2 for all FcγRs (FIG. 16A). The IgG3-DHS showed same binding activities comparing with wild type IgG3 for all FcγRs (FIG. 16B). The IgG4-DHS showed same binding activities comparing with wild type IgG4 for all FcγRs (FIG. 16C). In conclusion, three amino acids substitutions not affect FcγR-binding activities of IgG subclasses.

Figure 19:
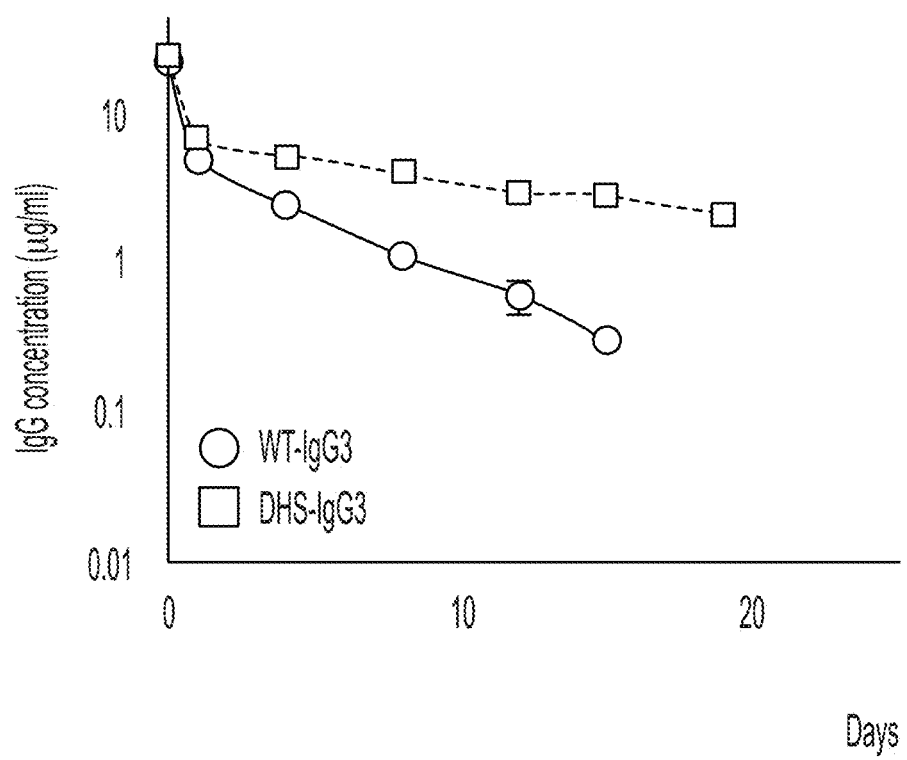
FIG. 19. Pharmacokinetics of antibodies in human FcRn transgenic mice.

PK studies: Using same methods as in EXAMPLE 11, the pharmacokinetics of IgG2-DHS and IgG4-DHS were evaluated. As results, IgG2-DHS showed 2.9-fold increased beta phase serum half-life (β phase $T_{1/2}$=199.8±4.9 hours) than wild type IgG2 (FIG. 17 and Table 9). IgG2-DHS also showed 1.9-fold slow clearance rate (0.067±0.015 ml/day/kg), 1.9-fold enhanced AUCinf (148.3±7.5 μg*days/ml), and 1.5-fold lower tissue distribution (0.57±0.02 ml/kg) than wild type IgG2. And IgG4-DHS showed 3.6-fold increased beta phase serum half-life (β phase $T_{1/2}$=277.4±14.9 hours) than wild type IgG4 (FIG. 16 and Table 9). IgG4-DHS also showed 2.4-fold slow clearance rate (0.067±0.048 ml/day/kg), 2.4-fold enhanced AUCinf (149.2±6.3m*days/ml), and 1.7-fold lower tissue distribution (0.58±0.03 ml/kg) than wild type IgG4. IgG3-DHS showed 4.4-fold increased beta phase serum half-life (β phase $T_{1/2}$=286.3±14.6 hours) than wild type IgG3 (FIG. 19 and Table 13). IgG3-DHS also showed 3.8-fold slow clearance rate (0.076±0.007 ml/day/kg), 3.9-fold enhanced AUCinf (269.0±22.4 μg*days/ml), and 2.1-fold lower tissue distribution (0.41±0.05 ml/kg) than wild type IgG3 (FIG. 19 and Table 13).

TABLE 9

Pharmacokinetic values of DHS-Fc variant

|  | Clearance (ml/days/kg) | β phase $T_{1/2}$ (hrs) | $AUC_{inf.}$ (μg * days/ml) | Vss (ml/kg) |
|---|---|---|---|---|
| Wild type IgG2 | 0.13 ± 0.02 | 68.0 ± 7.5 | 77.5 ± 5.6 | 0.87 ± 0.11 |
| IgG2-DHS | 0.067 ± 0.015 | 199.8 ± 4.9 | 148.3 ± 7.5 | 0.57 ± 0.02 |
| Wild type IgG4 | 0.16 ± 0.03 | 76.8 ± 9.4 | 62.4 ± 8.3 | 1.0 ± 0.1 |
| IgG4-DHS | 0.067 ± 0.048 | 277.4 ± 14.9 | 149.2 ± 6.3 | 0.58 ± 0.03 |

TABLE 13

Pharmacokinetic values of DHS-Fc variant

|  | Clearance (ml/days/kg) | β phase $T_{1/2}$ (hrs) | $AUC_{inf.}$ (μg * days/ml) | Vss (ml/kg) |
|---|---|---|---|---|
| Wild type IgG3 | 0.288 ± 0.01 | 65.6 ± 7.9 | 69.8 ± 2.9 | 0.85 ± 0.06 |
| IgG3-DHS | 0.076 ± 0.007 | 286.3 ± 14.6 | 269.0 ± 22.4 | 0.41 ± 0.05 |

Example 13

Rheumatoid Factor Binding Properties

In patients with autoimmune diseases, including rheumatoid arthritis (RA), rheumatoid factor (RF) is often observed and can weaken the therapeutic efficacy of therapeutic antibodies by removing serum antibodies from the blood (Newkirk 2002, Ingegnoli et al., 2013, Maeda et al., 2017). So, we tested RF-binding ability of antibody variants by ELISA.

Figure 20:
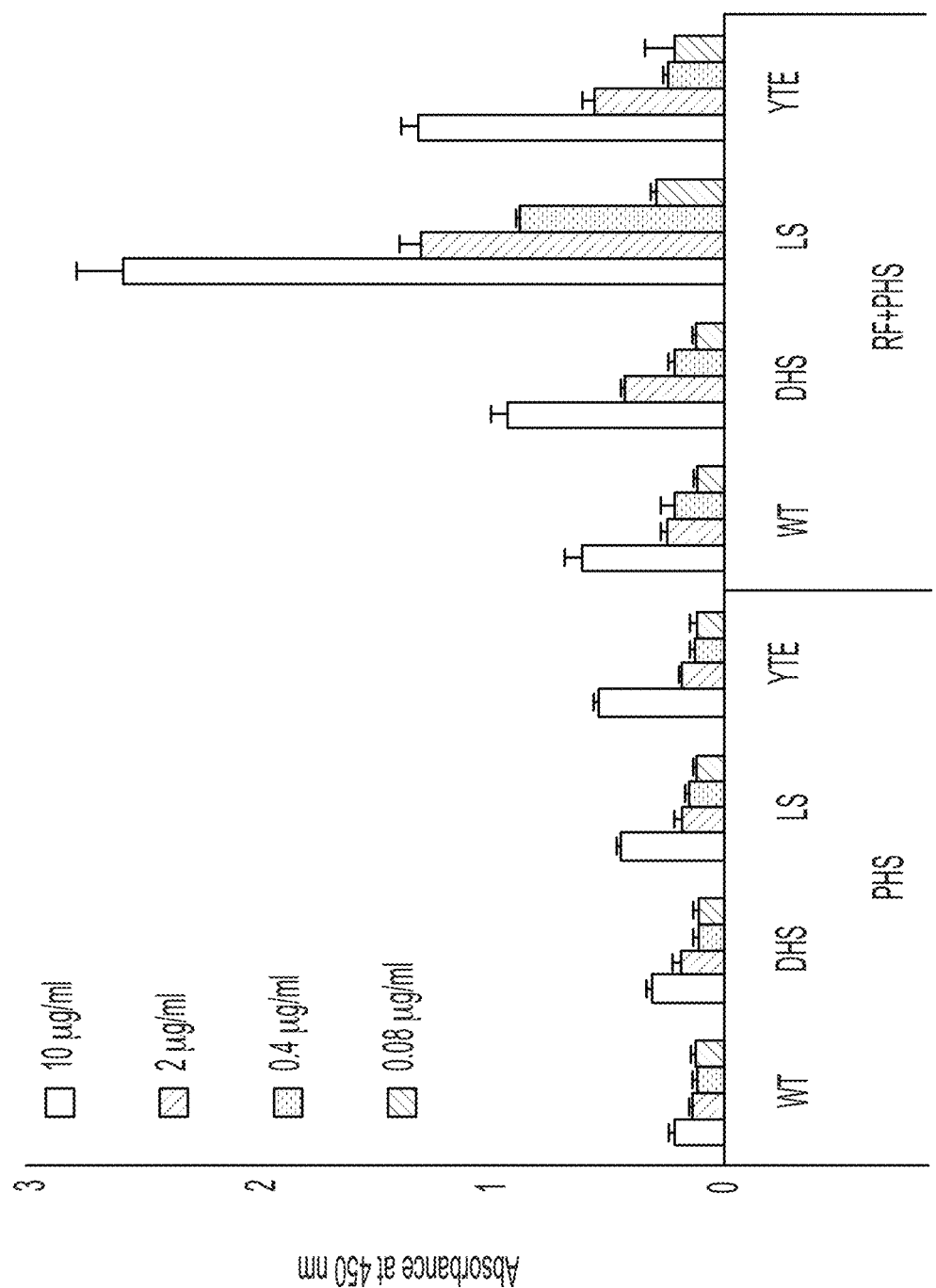
FIG. 20: Rheumatoid factor binding assay for antibody variants.

ELISA measurements of IgG variants with rheumatoid factor: The binding property of DHS to RF was assayed. Briefly, 50 μl of rheumatoid factor positive serum (Lee Biosolutions) was coated onto a 96-well EIA/RIA plate (Qiagen) at 4° C. overnight, and the plates were washed three times with PB ST. The plates were blocked for 1 h at room temperature with 1% BSA in PBS and washed three times with PBST. The serially diluted biotinylated antibody variants were then added to the plates. After 1 h of incubation at room temperature, the plates were washed with PBST and were incubated with 50 μL of PBS containing 1:5000 streptavidin-HRP (Thermo Fisher Scientific) for 1 h. After three times of washing with PBST, 50 μL TMB substrate was added per well (Thermo Scientific), 50 μL of 1 M $H_2SO_4$ was added to neutralize, and the absorbance at 450 nm was recorded. Herceptin-DHS showed the comparative binding response level with wild type Herceptin but Herceptin-YTE and Herceptin-LS showed the stronger binding activities than wild type Herceptin (FIG. 20).

TABLE 10

Primers used in this study (provided as SEQ ID NOs: 12-19)

| SEQ ID NO: | Primer Name | Primer nucleotide sequence (5'→3') |
|---|---|---|
| 12 | PCHT09 | GTT ATT ACT CGC GGC CCA GCC GGC CAT GGC GGA GGT TCA A |
| 13 | PCHT10 | CTT GGG TTT TGG GGG GAA GAG GAA GAC |
| 14 | PCHT11 | GTC TTC CTC TTC CCC CCA AAA CCC AAG VRK VMB CDC VWB VWH VRK VRK ACC CCT GAG GTC ACA TGC GTG GTG |
| 15 | PCHT12 | GAC CTT GCA CTT GTA CTC CTT GCC ATT GHG CCA MYB GHG GTG VWS VWS GGT GAG GAC GCT GAC CAC ACG GTA |
| 16 | PCHT13 | AAT GGC AAG GAG TAC AAG TGC AAG GTC |
| 17 | PCHT14 | CGG GGA CAG GGA GAG GCT CTT MYB CGT GTV GTG MYB GTG GHG AGC MYB ATG CAT CAC GGA GCA TGA GAA GAC GTT |
| 18 | PCHT15 | AAG AGC CTC TCC CTG TCC CCG |
| 19 | PCHT16 | GCG GCC GCG AAT TCG CCC CCG GAG GCC CCT TTA CCC GGG G |
| 20 | TH083 | GTC GAC AAG AAA GTT GAG CCC AAA TCT TGC GAC AAA ACT CAC ACA TGC CCA CCG |
| 21 | TH084 | C TCG AGC GGC CGC TCA TTT ACC CGG GGA CAG GGA GAG G |
| 22 | TH081 | TGA GCG GCC GCT CGA G |
| 23 | TH082 | GCA AGA TTT GGG CTC AAC TTT CTT GTC GAC |

TABLE 11

Plasmids used in this study

| Plasmids | Relevant characteristics | Reference or Source |
|---|---|---|
| pMopac12-pe1B-IgG-VH-CH1-CH2-CH3-FLAG | Bacterial display vector containing IgGVH1-CH1-CH2 and CH3 domains of trastuzumab | Jung et al., 2012 |
| pBAD30-Pe1B-VL-Ck-N1pA-VL-Ck-His-cMyc | Bacterial display vector containing IgGVL-Ck domains of trastuzumab | Jung et al., 2012 |
| pMaz-IgH-FcγRI-His | FcγRI gene in pMaz-IgH for monomeric mammalian expression | Jung et al., 2012 |

TABLE 11-continued

Plasmids used in this study

| Plasmids | Relevant characteristics | Reference or Source |
|---|---|---|
| pMaz-IgH-FcγRIIA$_{H131}$-GST | FcγRIIA$_{H131}$ gene in pMaz-IgH for dimeric mammalian expression | Jung et al., 2012 |
| pMaz-IgH-FcγRIIA$_{R131}$-GST | FcγRIIA$_{R131}$ gene in pMaz-IgH for dimeric mammalian expression | Jung et al., 2012 |
| pMaz-IgH-FcγRIIB-GST | FcγRIIB gene in pMaz-IgH for dimeric mammalian expression | Jung et al., 2012 |
| pMaz-IgH-FcγRIIIA$_{V157}$-GST | FcγRIIIA$_{V157}$ gene in pMaz-IgH for dimeric mammalian expression | Jung et al., 2012 |
| pMaz-IgH-FcγRIIIA$_{F157}$-GST | FcγRIIIA$_{F157}$ gene in pMaz-IgH for dimeric mammalian expression | Jung et al., 2012 |
| pcDNA3.4-IgH-Herceptin | Mammalian expression vector containing Herceptin heavy chain | This study |
| pcDNA3.4-IgH-Herceptin-DHS | Mammalian expression vector containing Herceptin-DHS heavy chain | This study |
| pcDNA3.4-IgH-Herceptin-LS | Mammalian expression vector containing Herceptin-LS heavy chain | This study |
| pcDNA3.4-IgH-Herceptin-YTE | Mammalian expression vector containing Herceptin-YTE heavy chain | This study |
| pcDNA3.4-IgH-Herceptin-IgG2 | Mammalian expression vector containing Herceptin-IgG2 heavy chain | This study |
| pcDNA3.4-IgH-Herceptin-IgG3 | Mammalian expression vector containing Herceptin-IgG3 heavy chain | This study |
| pcDNA3.4-IgH-Herceptin-IgG4 | Mammalian expression vector containing Herceptin-IgG4 heavy chain | This study |
| pcDNA3.4-IgH-Herceptin-IgG2-DHS | Mammalian expression vector containing Herceptin-IgG2-DHS heavy chain | This study |
| pcDNA3.4-IgH-Herceptin-IgG3-DHS | Mammalian expression vector containing Herceptin-IgG3-DHS heavy chain | This study |
| pcDNA3.4-IgH-Herceptin-IgG4-DHS | Mammalian expression vector containing Herceptin-IgG4-DHS heavy chain | This study |
| pcDNA3.4-IgL-Herceptin | Mammalian expression vector containing Herceptin light chain | This study |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,846,945
U.S. Pat. No. 7,094,571
U.S. Pat. No. 7,419,783
U.S. Pat. No. 7,611,866
U.S. Patent Publ. 2003/0219870
PCT Publn. WO 2008/137475
Abbondanzo et al., *Breast Cancer Res. Treat.*, 16:182(151), 1990.
Acqua et al., *J Immunol.* November 1: 169(9):5171-80, 2002.
Austin-Ward and Villaseca, *Revista Medica de Chile*, 126 (7):838-845, 1998.
Berberian et al., *Science*, 261(5128):1588-91, 1993.
Bhattacharya-Chatterjee M, Kohler H., *Adv Exp Med Biol.*, 251:113-27, 1989.
Borrok et al., *ACS Chem. Biol.*, 7:1596-1602, 2012.
Borrok et al., *J Biol Chem.*, 290(7):4282-90, 2015.
Bukowski et al., *Clinical Cancer Res.*, 4(10):2337-2347, 1998.
Challa et al., *Curr Top Microbiol Immunol.*, 382:249-72, 2014.
Chames et al., *Proc. Natl. Acad. Sci. USA*, 97:7969-7974, 2000.
Chaudhury et al., *J Exp Med.* 197(3), 315-322, 2003.
Christodoulides et al., *Microbiology*, 144(Pt 11):3027-3037, 1998.
Cleary et al., *Trends Microbiol.* April; 2(4):131-6, 1994.
Cooper et al., *Front. Pharmacol.* 5, 225, 2014.
Dall'Acqua et al., *J Immunol.* November 1; 169(9):5171-80, 2002.
Datta-Mannan et al., *Drug Metab. Dispos.* 35, 86-94, 2007.
Datta-Mannan et al., *Drug Metab. Dispos.* 40, 1545-1555, 2012.
Davidson et al., *J. Immunother.*, 21(5):389-398, 1998.
De Jager et al., *Semin. Nucl. Med.*, 23(2):165-179, 1993.
Deng et al., *Drug Metab. Dispos.* 38, 600-605, 2010.7
Desai et al., *Cancer Res.*, 58:2417-2425, 1998.

Dickinson et al., *J. Clin. Investig.* 104, 903-911, 1999
Doolittle and Ben-Zeev, *Methods Mol Biol,* 109:215-237, 1999.
Edelman et al., *Proc Natl Acad Sci USA,* 63:78-85, 1969.
Elvin et al., *Int. J. Pharm.,* 440:83-98, 2013.
Firan et al., *Int. Immunol.* 13, 993-1002, 2001.
Gan et al., *Traffic.,* 10(5):600-14, 2009
Ghetie and Ward, *Annu. Rev. Immunol.,* 18:739-766, 2000.
Ghetie and Ward, *Eur.J. Immunol.,* 26:690-696, 1996.
Griffiths and Duncan, *Curr. Opin. Biotechnol.,* 9:102-108, 1998.
Gulbis and Galand, *Hum. Pathol.,* 24(12):1271-1285, 1993.
Hanibuchi et al., *Int. J. Cancer,* 78(4):480-485, 1998.
Harvey et al., *J. Immunol. Methods.* 308:43-52, 2006.
Harvey et al., *Proc. Natl. Acad. Sci. USA,* 101:9193-9198, 2004.
Haymann et al., *J. Am. Soc. Nephrol.* 11, 632-639, 2000.
Hellstrand et al., *Acta Oncologica,* 37(4):347-353, 1998.
Hinton et al., *J. Biol. Chem.* 279, 6213-6216, 2004.
Hinton et al., *J. Immunol.* 176, 346-356, 2006.
Hollander, *Front. Immun.,* 3:3, 2012.
Hoogenboom and Winter, *J. Mol. Biol.,* 227:381-388, 1992.
Hoogenboom et al., *Immunotechnology,* 4:1-20, 1998.
Hui and Hashimoto, *Infection Immun.,* 66(11):5329-5336, 1998.
Ingegnoli et al., *Disease Markers,* 35(6), 727-734, 2013.
Israel et al., *Immunology.* December; 89(4):573-8, 1996.
Israel et al., *Immunology* 92, 69-74, 1997.
Jefferis, *Adv. Exp. Med. Biol.,* 564:143-148, 2005.
Jung et al., *ACS Chem. Biol.,* 8:368-375, 2012.
Jung et al., *Proc. Natl. Acad. Sci. USA,* 107:604-609, 2010.
Kabat et al., In: *Sequences of Proteins of Immunological Interest,* U.S. Dept. of Health and Hum. Serv., Bethesda, 1991.
Kang et al., *Science.* May 20; 240(4855):1034-6, 1988.
Kim et al., 1999. *Eur J Immunol.,* 29(9):2819-25, 1999.
Kjaer et al., *FEBS Lett.,* 431:448-452, 1998.
Ko et al., *Nature.* 514, 642-645, 2014.
Kohler and Milstein, *Nature,* 256, 495-497, 1975.
Kreier et al., *Ann. Rev. Microbiol.* 35:325-38, 1981.
Kyte and Doolittle, *J Mol Biol.,* 157(1):105-32, 1982.
Lee et al., *Nat Immunol.,* 18(8), 889-898, 2017
Lenert et al., 1990. *Immunobiology.,* 161(5):488-93, 1982.
Maeda et al., *mAbs,* 9(5), 844-853, 2017
Martin et al., 2001. *Mol Cell.,* 7(4):867-77, 2001.
Munson and Pollard, *Anal. Biochem.,* 107:220, 1980.
Newkirk, *Clinical Immunology,* 104(1), 1-13, 2002
Ober et al., *J. Immunol.,* 172:2021-2029, 2004b.
Ober et al., *Proc. Natl. Acad. Sci. USA,* 101:11076-11081, 2004a.
Orlandi et al., *Proc. Natl. Acad. Sci. USA,* 86:3833-3837, 1989.
Qin et al., *Proc. Natl. Acad. Sci. USA,* 95(24):14411-14416, 1998.
Robbie et al., *Antimicrob. Agents Chemother.* 57, 6147-6153, 2013.
Roopenian and Akilesh, *Nat Rev Immunol.,* 7(9):715-25, Aug. 17, 2007.
Roopenian et al., *J Immunol.* 170(7), 3528-3533, 2003.
Sambrook et al., In: *Molecular cloning: a laboratory manual,* $2^{nd}$ Ed., Cold Spring Harbor Laboratory Press, Cold Spring Harbor, N.Y., 1989.
Silverman, 1995. *Ann NY Acad Sci.* September 29; 764:342-55, 1995.
Walters et al., *J Biol Chem.,* 291(4):1817-25. 2016.
Wang et al., *Drug Metab. Dispos.* 39, 1469-1477, 2011.
Ward et al., *Mol Immunol.,* 67(2 Pt A):131-41, 2015.
Yeung et al., *Cancer Res.* 70, 3269-3277, 2010.
Yeung et al., *J. Immunol.* 182, 7663-7671, 2009.
Zalevsky et al., *Nat. Biotechnol.* 28, 157-159, 2010.
Zheng et al., *Clin. Pharmacol. Ther.* 89, 283-290, 2011.

What is claimed is:

1. A nucleic acid encoding a polypeptide comprising a variant IgG Fc domain that binds human FcRn at an acidic pH, wherein the Fc domain has the following substitutions: (i) aspartic acid at position 309 (L/V309D); (ii) histidine at position 311 (Q311H); and (iii) a substitution at position 434 of either a serine or tyrosine (N434Y or N434S); with amino acid position numbering being according to the Kabat system.

2. The nucleic acid of claim 1, wherein the substitution at position 434 is serine (N434S).

3. The nucleic acid of claim 1, wherein the substitution at position 434 is tyrosine (N434Y).

4. The nucleic acid of claim 1, wherein the Fc domain is glycosylated.

5. The nucleic acid of claim 1, wherein the Fc domain has substantially equivalent, essentially the same, about the same, or the same binding to FcγR as compared to wild-type.

6. The nucleic acid of claim 1, wherein the Fc domain has a binding capacity that is substantially equivalent, essentially the same, about the same, the same as, or equivalent to 1, 2, or all of FcγRI, FcγRII, and FcγRIII, as compared to wild-type.

7. The nucleic acid of claim 1, wherein the Fc domain binds FcRn at an acidic pH with an affinity higher than a wild-type Fc domain.

8. The nucleic acid of claim 1, wherein the Fc domain does not detectably or selectively bind to FcRn, or exhibits no or essentially no binding to FcRn, at neutral pH.

9. The nucleic acid of claim 1, wherein the Fc domain exhibits: (i) enhanced binding at pH 5.8 and (ii) reduced binding or no detectable binding at pH 7.4 for FcRn, as compared to a wild-type Fc domain.

10. The nucleic acid of claim 1, wherein the Fc domain is aglycosylated.

11. The nucleic acid of claim 1, wherein the Fc domain further comprises a substitution of glutamic acid at position 264 (V264E).

12. The nucleic acid of claim 1, wherein the IgG Fc domain is a IgG1 Fc domain.

13. The nucleic acid of claim 1, wherein the IgG Fc domain is a IgG2 Fc domain.

14. The nucleic acid of claim 1, wherein the IgG Fc domain is a IgG3 Fc domain.

15. The nucleic acid of claim 1, wherein the IgG Fc domain is a IgG4 Fc domain.

16. The nucleic acid of claim 1, wherein the Fc domain comprises substitutions selected from the group consisting of: V264E, L309D, Q311H and N434S; V264E, L309D, Q311H and N434Y; V264E, V309D, Q311H and N434S; V264E, V309D, Q311H and N434Y; L309D, Q311H, and N434S; V309D, Q311H, and N434S; V309D, Q311H, and N434Y; and L309D, Q311H, and N434Y.

17. The nucleic acid of claim 16, wherein the Fc domain comprises: L309D, Q311H, and N434S; or L309D, Q311H, and N434Y.

18. The nucleic acid of claim 1, wherein the Fc domain binds FcRn with a $K_D$ value of less than 550 nM.

19. The nucleic acid of claim 18, wherein the Fc domain binds FcRn with a $K_D$ value of less than 250 nM.

20. The nucleic acid of claim 19, wherein the Fc domain binds FcRn with a $K_D$ value of less than 125 nM.

21. The nucleic acid of claim 1, further comprising a non-Fc receptor (non-FcR) binding domain.

22. The nucleic acid of claim 21, wherein the non-FcR binding domain is an Ig variable domain.

23. The nucleic acid of claim 1, wherein the polypeptide is an antibody.

24. The nucleic acid of claim 23, wherein the antibody is a human antibody.

25. The nucleic acid of claim 23, wherein the antibody is a full-length antibody.

26. The nucleic acid of claim 23, wherein the antibody is an agonistic antibody.

27. The nucleic acid of claim 23, wherein the antibody is an antagonistic antibody.

28. The nucleic acid of claim 23, wherein the antibody selectively binds Her2/neu, CD20, CD40, IL-10, 4-1BB, PD-1, PD-L1, CTLA-40X40, IL-1, IL-6, IL6R, TNFα, RANKL, EGFR, c-Met, CD11a, VEGF-A, VEGFR1, VEGFR2, C5, or Integrin-α4.

29. The nucleic acid of claim 23, wherein the antibody is chemically conjugated to or covalently bound to a toxin.

30. The nucleic acid of claim 21, wherein the non-FcR binding region is not an antigen binding site of an antibody.

31. The nucleic acid of claim 21, wherein the non-FcR binding region binds a cell-surface protein.

32. The nucleic acid of claim 21, wherein the non-FcR binding regions binds a soluble protein.

33. The nucleic acid of claim 16, wherein the Fc domain comprises SEQ ID NO: 5.

34. The nucleic acid of claim 16, wherein the Fc domain comprises V264E, L309D, Q311H, and N434S.

35. The nucleic acid of claim 16, wherein the Fc domain comprises V264E, L309D, Q311H, and N434Y.

36. The nucleic acid of claim 16, wherein the Fc domain comprises L309D, Q311H, and N434S.

37. The nucleic acid of claim 16, wherein the Fc domain comprises L309D, Q311H, and N434Y.

38. The nucleic acid of claim 1, wherein the nucleic acid is a DNA segment.

39. The nucleic acid of claim 38, wherein the nucleic acid is an expression vector.

40. A host cell comprising the nucleic acid of claim 1.

41. The host cell of claim 40, wherein said host cell expresses said nucleic acid.

* * * * *

UNITED STATES PATENT AND TRADEMARK OFFICE
CERTIFICATE OF CORRECTION

PATENT NO. : 11,958,904 B2
APPLICATION NO. : 17/346648
DATED : April 16, 2024
INVENTOR(S) : George Georgiou et al.

Page 1 of 1

It is certified that error appears in the above-identified patent and that said Letters Patent is hereby corrected as shown below:

In the Claims

Claim 5, Column 77, Line 40, "FcyR" should be --Fc$\gamma$R--.

Signed and Sealed this
Twenty-fifth Day of June, 2024

Katherine Kelly Vidal
*Director of the United States Patent and Trademark Office*